US011447573B2

(12) United States Patent
Chou et al.

(10) Patent No.: US 11,447,573 B2
(45) Date of Patent: Sep. 20, 2022

(54) MULTISPECIFIC ANTIGEN BINDING PROTEINS AND METHODS OF USE THEREOF

(71) Applicant: NANJING LEGEND BIOTECH CO., LTD., Jiangsu (CN)

(72) Inventors: Chuan-Chu Chou, Westfield, NJ (US); Yafeng Zhang, Nanjing (CN); Shu Wu, Nanjing (CN); Zhenyu Liu, Nanjing (CN); Zhongdao Li, Nanjing (CN); Fangliang Zhang, Nanjing (CN)

(73) Assignee: NANJING LEGEND BIOTECH CO., LTD., Nanjing (CN)

( * ) Notice: Subject to any disclaimer, the term of this patent is extended or adjusted under 35 U.S.C. 154(b) by 345 days.

(21) Appl. No.: 16/319,224

(22) PCT Filed: Jul. 20, 2017

(86) PCT No.: PCT/CN2017/093644
§ 371 (c)(1),
(2) Date: Jan. 18, 2019

(87) PCT Pub. No.: WO2018/014855
PCT Pub. Date: Jan. 25, 2018

(65) Prior Publication Data
US 2019/0202935 A1    Jul. 4, 2019

(30) Foreign Application Priority Data

Jul. 20, 2016   (WO) ................ PCT/CN2016/090703

(51) Int. Cl.
| | |
|---|---|
| C07K 16/46 | (2006.01) |
| C07K 16/28 | (2006.01) |
| A61P 35/00 | (2006.01) |
| A61P 37/00 | (2006.01) |
| A61P 29/00 | (2006.01) |
| C07K 16/24 | (2006.01) |
| C07K 16/30 | (2006.01) |
| A61K 39/00 | (2006.01) |

(52) U.S. Cl.
CPC .............. *C07K 16/46* (2013.01); *A61P 29/00* (2018.01); *A61P 35/00* (2018.01); *A61P 37/00* (2018.01); *C07K 16/24* (2013.01); *C07K 16/2818* (2013.01); *C07K 16/30* (2013.01); A61K 2039/505 (2013.01); C07K 2317/24 (2013.01); C07K 2317/31 (2013.01)

(58) Field of Classification Search
CPC ........ C07K 16/46; C07K 16/24; C07K 16/30; C07K 2317/24; C07K 2317/31; A61P 37/00; A61P 29/00; A61P 35/00
See application file for complete search history.

(56) References Cited

U.S. PATENT DOCUMENTS

| | | |
|---|---|---|
| 3,773,919 A | 11/1973 | Boswell |
| RE30,985 E | 6/1982 | Cartaya |
| 4,419,446 A | 12/1983 | Howley |
| 4,560,655 A | 12/1985 | Baker |
| 4,601,978 A | 7/1986 | Karin |
| 4,657,866 A | 4/1987 | Kumar |
| 4,676,980 A | 6/1987 | Segal |
| 4,767,704 A | 8/1988 | Cleveland et al. |
| 4,816,567 A | 3/1989 | Cabilly |
| 4,927,762 A | 5/1990 | Darfler |
| 4,965,199 A | 10/1990 | Capon |
| 5,122,469 A | 6/1992 | Mather |
| 5,229,275 A | 7/1993 | Goroff |
| 5,264,365 A | 11/1993 | Georgiou |
| 5,500,362 A | 3/1996 | Robinson |
| 5,508,192 A | 4/1996 | Georgiou |
| 5,545,806 A | 8/1996 | Lonberg et al. |
| 5,545,807 A | 8/1996 | Surani |
| 5,565,332 A | 10/1996 | Hoogenboom et al. |
| 5,567,610 A | 10/1996 | Borrebaeck |
| 5,569,825 A | 10/1996 | Lonberg |
| 5,571,894 A | 11/1996 | Wels |
| 5,573,905 A | 11/1996 | Lerner |
| 5,587,458 A | 12/1996 | King |
| 5,591,669 A | 1/1997 | Krimpenfort et al. |
| 5,591,828 A | 1/1997 | Bosslet |
| 5,624,821 A | 4/1997 | Winter |
| 5,625,126 A | 4/1997 | Lonberg |
| 5,633,425 A | 5/1997 | Lonberg et al. |
| 5,639,635 A | 6/1997 | Joly |

(Continued)

FOREIGN PATENT DOCUMENTS

| | | |
|---|---|---|
| CN | 1388136 A | 1/2003 |
| CN | 101932608 A | 12/2010 |

(Continued)

OTHER PUBLICATIONS

Richard et al, Plos One (2013), vol. 8(7): e69495. (Year: 2013).*
Schaefer et al, PNAS (2011), vol. 108, No. 27, 11187-11192. (Year: 2011).*
Mabry et al, Protein Engineering, Design & Selection (2010), vol. 23, No. 3, p. 115-127. (Year: 2010).*
Almagro, J. et al. (Jan. 1, 2008). "Humanization of Antibodies," Frontiers in Bioscience 13:1619-1633.
Arie, J-P. et al. (Jan. 1, 2001). "Chaperone Function of FkpA, a Heat Shock Prolyl Isomerase, in the Periplasm of *Escherichia coli*," Molecular Micorbiology 39(1):199-210.

(Continued)

*Primary Examiner* — Brad Duffy
*Assistant Examiner* — Cheom-Gil Cheong
(74) *Attorney, Agent, or Firm* — Morrison and Foerster

(57) ABSTRACT

Disclosed herein are multispecific, such as bispecific, antigen binding proteins comprising a first antigen binding domain comprising a heavy chain variable domain and a light chain variable domain, and a second antigen binding domain comprising a single-domain antibody. Pharmaceutical compositions comprising the multispecific antigen binding proteins, kits and methods of use thereof are further provided.

19 Claims, 15 Drawing Sheets

Specification includes a Sequence Listing.

(56) References Cited

U.S. PATENT DOCUMENTS

| | | |
|---|---|---|
| 5,641,870 A | 6/1997 | Rinderknecht |
| 5,648,237 A | 7/1997 | Carter |
| 5,648,260 A | 7/1997 | Winter |
| 5,661,016 A | 8/1997 | Lonberg et al. |
| 5,731,168 A | 3/1998 | Carter |
| 5,739,277 A | 4/1998 | Presta |
| 5,750,373 A | 5/1998 | Garrard |
| 5,770,429 A | 6/1998 | Lonberg et al. |
| 5,821,337 A | 10/1998 | Carter |
| 5,837,234 A | 11/1998 | Gentile |
| 5,840,523 A | 11/1998 | Simmons |
| 5,869,046 A | 2/1999 | Presta |
| 6,013,605 A | 1/2000 | Rees |
| 6,027,888 A | 2/2000 | Georgiou |
| 6,075,181 A | 6/2000 | Kucherlapati |
| 6,083,715 A | 7/2000 | Georgiou |
| 6,150,584 A | 11/2000 | Kucherlapati |
| 6,194,551 B1 | 2/2001 | Idusogie |
| 6,602,684 B1 | 8/2003 | Umana |
| 6,737,056 B1 | 5/2004 | Presta |
| 6,982,321 B2 | 1/2006 | Winter |
| 7,041,870 B2 | 5/2006 | Tomizuka |
| 7,087,409 B2 | 8/2006 | Barbas, III |
| 7,189,826 B2 | 3/2007 | Rodman |
| 7,332,581 B2 | 2/2008 | Presta |
| 7,371,826 B2 | 5/2008 | Presta |
| 7,371,849 B2 | 5/2008 | Honda |
| 7,504,256 B1 | 3/2009 | Ogawa |
| 7,521,541 B2 | 4/2009 | Eigenbrot |
| 7,527,791 B2 | 5/2009 | Adams |
| 8,754,287 B2 | 6/2014 | Macdonald |
| 10,385,137 B2 * | 8/2019 | Baty ................. C07K 16/283 |
| 2002/0164328 A1 | 11/2002 | Shinkawa |
| 2003/0115614 A1 | 6/2003 | Kanda |
| 2003/0157108 A1 | 8/2003 | Presta |
| 2004/0093621 A1 | 5/2004 | Shitara |
| 2004/0109865 A1 | 6/2004 | Niwa |
| 2004/0110282 A1 | 6/2004 | Kanda |
| 2004/0110704 A1 | 6/2004 | Yamane |
| 2004/0132140 A1 | 7/2004 | Satoh |
| 2004/0259150 A1 | 12/2004 | Nakamura |
| 2005/0014934 A1 | 1/2005 | Hinton |
| 2005/0031613 A1 | 2/2005 | Nakamura |
| 2005/0079574 A1 | 4/2005 | Bond |
| 2005/0119455 A1 | 6/2005 | Fuh |
| 2005/0123546 A1 | 6/2005 | Umana |
| 2005/0255115 A1 | 11/2005 | Huang et al. |
| 2005/0266000 A1 | 12/2005 | Bond |
| 2005/0272916 A1 | 12/2005 | Hanai |
| 2006/0025576 A1 | 2/2006 | Miller |
| 2007/0061900 A1 | 3/2007 | Murphy |
| 2007/0071675 A1 * | 3/2007 | Wu .................... A61P 25/06 424/1.49 |
| 2007/0117126 A1 | 5/2007 | Sidhu |
| 2007/0134759 A1 | 6/2007 | Nishiya |
| 2007/0160598 A1 | 7/2007 | Dennis |
| 2007/0178552 A1 | 8/2007 | Arathoon |
| 2007/0237764 A1 | 10/2007 | Birtalan |
| 2007/0292936 A1 | 12/2007 | Barthelemy |
| 2008/0241884 A1 | 10/2008 | Shitara |
| 2009/0002360 A1 | 1/2009 | Chen |
| 2009/0307787 A1 | 12/2009 | Grosveld |
| 2010/0122358 A1 | 5/2010 | Brueggemann |
| 2011/0028695 A1 | 2/2011 | Revets |
| 2011/0287009 A1 | 11/2011 | Scheer |
| 2013/0156769 A1 * | 6/2013 | Kufer ................. A61P 35/00 424/136.1 |
| 2013/0189735 A1 * | 7/2013 | Zardi ................. C07K 16/468 435/69.6 |
| 2014/0127210 A1 * | 5/2014 | Kim ................... A61P 35/00 424/136.1 |
| 2015/0086541 A1 * | 3/2015 | Aguilar-Cordova ..................... C12Y 305/04001 424/133.1 |
| 2015/0202291 A1 * | 7/2015 | Bosch ................ C07K 16/2818 424/156.1 |
| 2015/0232555 A1 | 8/2015 | Carven |
| 2015/0289489 A1 | 10/2015 | Macdonald |
| 2016/0000842 A1 * | 1/2016 | Song .................. A61K 45/06 424/93.2 |
| 2016/0083476 A1 | 3/2016 | Baty et al. |
| 2016/0145355 A1 * | 5/2016 | Saha .................. C07K 16/2818 424/136.1 |
| 2016/0166685 A1 * | 6/2016 | Cheung ............... A61P 37/04 424/133.1 |
| 2016/0272960 A1 | 9/2016 | Thanos et al. |
| 2019/0233519 A1 | 8/2019 | Zhang |
| 2020/0369770 A1 * | 11/2020 | Zhang ................ C07K 16/2803 |

FOREIGN PATENT DOCUMENTS

| | | |
|---|---|---|
| CN | 102369215 A | 3/2012 |
| CN | 105754990 A | 7/2016 |
| EP | 0308936 A2 | 3/1989 |
| EP | 0308936 A3 | 2/1990 |
| EP | 0368684 A1 | 5/1990 |
| EP | 0404097 A2 | 12/1990 |
| EP | 0404097 A3 | 12/1990 |
| EP | 1792991 A1 | 6/2007 |
| EP | 3263702 A1 | 1/2018 |
| EP | 3459597 A1 | 3/2019 |
| WO | 1987000195 A1 | 1/1987 |
| WO | 1990003430 A1 | 4/1990 |
| WO | 1991000360 A1 | 1/1991 |
| WO | 199110741 A1 | 7/1991 |
| WO | 1993001161 A1 | 1/1993 |
| WO | 1993008829 A1 | 5/1993 |
| WO | 1993011161 A1 | 6/1993 |
| WO | 1993016185 A2 | 8/1993 |
| WO | 1993016185 A3 | 9/1993 |
| WO | 1994004678 A1 | 3/1994 |
| WO | 1994004690 A1 | 3/1994 |
| WO | 1994011026 A2 | 5/1994 |
| WO | 1994029351 A2 | 12/1994 |
| WO | 1994029351 A3 | 2/1995 |
| WO | 1996016673 A1 | 6/1996 |
| WO | 1996027011 A1 | 9/1996 |
| WO | 1996033735 A1 | 10/1996 |
| WO | 1996034096 A1 | 10/1996 |
| WO | 1996034103 A1 | 10/1996 |
| WO | 1997017852 A1 | 5/1997 |
| WO | 1997030087 A1 | 8/1997 |
| WO | 1997049805 A2 | 12/1997 |
| WO | 1997049805 A3 | 2/1998 |
| WO | 1998022141 A2 | 5/1998 |
| WO | 1998024893 A2 | 6/1998 |
| WO | 1998024893 A3 | 8/1998 |
| WO | 1998050431 A2 | 11/1998 |
| WO | 1998058964 A1 | 12/1998 |
| WO | 1998022141 A3 | 1/1999 |
| WO | 1999022764 A1 | 5/1999 |
| WO | 1999037681 A2 | 7/1999 |
| WO | 1999037681 A3 | 10/1999 |
| WO | 1999051642 A1 | 10/1999 |
| WO | 2000027435 A1 | 5/2000 |
| WO | 2000043507 A1 | 7/2000 |
| WO | 2000061739 A1 | 10/2000 |
| WO | 2001014424 A2 | 3/2001 |
| WO | 2001029246 A1 | 4/2001 |
| WO | 2001077137 A1 | 10/2001 |
| WO | 2001090190 A2 | 11/2001 |
| WO | 2002031140 A1 | 4/2002 |
| WO | 2001077137 A9 | 5/2002 |
| WO | 2001090190 A3 | 8/2002 |
| WO | 2002085945 A2 | 10/2002 |
| WO | 2003011878 A2 | 2/2003 |
| WO | 2003014161 A2 | 2/2003 |
| WO | 2002085945 A3 | 3/2003 |
| WO | 2003025020 A1 | 3/2003 |
| WO | 2003035694 A2 | 5/2003 |
| WO | 2003014161 A3 | 8/2003 |
| WO | 2003035694 A3 | 10/2003 |

(56) References Cited

FOREIGN PATENT DOCUMENTS

| | | | |
|---|---|---|---|
| WO | 2003084570 A1 | 10/2003 |
| WO | 2003085107 A1 | 10/2003 |
| WO | 2003011878 A3 | 11/2003 |
| WO | 2003014161 A9 | 4/2004 |
| WO | 2004042072 A2 | 5/2004 |
| WO | 2004049794 A2 | 6/2004 |
| WO | 2004056312 A2 | 7/2004 |
| WO | 2004092219 A2 | 10/2004 |
| WO | 2004042072 A3 | 12/2004 |
| WO | 2004049794 A3 | 12/2004 |
| WO | 2004092219 A3 | 2/2005 |
| WO | 2005035586 A1 | 4/2005 |
| WO | 2005035778 A1 | 4/2005 |
| WO | 2004056312 A3 | 5/2005 |
| WO | 2005053742 A1 | 6/2005 |
| WO | 2003085119 A1 | 8/2005 |
| WO | 2005100402 A1 | 10/2005 |
| WO | 2006003388 A2 | 1/2006 |
| WO | 2006008548 A2 | 1/2006 |
| WO | 2006029879 A2 | 3/2006 |
| WO | 2006030220 A1 | 3/2006 |
| WO | 2006003388 A3 | 4/2006 |
| WO | 2006008548 A3 | 6/2006 |
| WO | 2006029879 A3 | 9/2006 |
| WO | 2006138670 A2 | 12/2006 |
| WO | 2007112940 A2 | 10/2007 |
| WO | 2007112940 A3 | 1/2008 |
| WO | 2008077546 A1 | 7/2008 |
| WO | 2009068649 A2 | 6/2009 |
| WO | 2009089004 A1 | 7/2009 |
| WO | 2010097597 A1 | 9/2010 |
| WO | 2010112193 A1 | 10/2010 |
| WO | 2011036460 A1 | 3/2011 |
| WO | 2012155019 A1 | 11/2012 |
| WO | 2012158818 A2 | 11/2012 |
| WO | 2013019906 A1 | 2/2013 |
| WO | 2014209804 A1 | 12/2014 |
| WO | 2016024231 A1 | 2/2016 |
| WO | 2016061142 A1 | 4/2016 |
| WO | 2016187594 A1 | 11/2016 |
| WO | 2017143406 A1 | 8/2017 |
| WO | 2017165681 A1 | 9/2017 |
| WO | 2018014260 A1 | 1/2018 |
| WO | 2018014855 A1 | 1/2018 |
| WO | 2018068201 A1 | 4/2018 |
| WO | 2018068695 A1 | 4/2018 |

OTHER PUBLICATIONS

Armour, K.L. et al. (1999). "Recombinant Human IgG Molecules Lacking Fcγ Receptor I Binding and Monocyte Triggering Activities," Eur. J. Immunol. 29:2613-2624.
Baca, M. et al. (Apr. 18, 1997). "Antibody Humanization Using Monovalent Phage Display," J. Biol. Chem. 272 (16):10678-10684.
Bachmann, B.J. (1987). "Section G. Strains and Useful Strain Constructions. Derivations and Genotypes of Some Mutant Derivatives of Escherichia coli K-12," Cellular and Molecular Biology, vol. 2, Neidhardt, F. C. et al., Washington, D.C., American Society for Microbiology, pp. 1190-1219.
Balzano, C. et al. (1992). "CTLA-4 and CD28: Similar Proteins, Neighbouring Genes," Int. J. Cancer Suppl. 7:28-32. (Abstract Only).
Barbas III, C.F. et al. (Apr. 1994). "In Vitro Evolution of a Neutralizing Human Antibody to Human Immunodeficiency Virus Type 1 To Enhance Affinity and Broaden Strain Cross-Reactivity," Proc Nat. Acad. Sci. USA 91:3809-3813.
Barnes, D. et al. (Mar. 1, 1980). "Methods for Growth of Cultured Cells in Serum-Free Medium," Anal. Biochem. 102(2):255-270.
Bass, S. et al. (1990). "Hormone Phage: An Enrichment Method for Variant Proteins With Altered Binding Properties," Proteins 8:309-314.

Boerner, P. et al. (Jul. 1, 1991). "Production of a Antigen-Specific Human Monoclonal Antibodies from in Vitro-Primed Human Splenocytes," J. Immunol. 147(1):86-95.
Bothmann, H. et al., (Jun. 2, 2000). "The Periplasmic Escherichia coli Peptidylprolyl cis,trans-Isomerase FkpA," The Journal of Biological Chemistry 275(22):17100-17105.
Brennan, M. et al. (Jul. 5, 1985). "Preparation of Bispecific Antibodies by Chemical Recombination of Monoclonal Immunoglobulin G1 Fragments," Science 229:81-83.
Brüggemann, M. et al. (1993). "Designer Mice: The Production of Human Antibody Repertoires in Transgenic Animals," Year in Immuno. 7:33-40.
Brüggemann, M. et al. (Nov. 1, 1987). "Comparison of the Effector Functions of Human Immunoglobulins Using a Matched Set of Chimeric Antibodies," J. Exp. Med. 166:1351-1361.
Capel, P.J. et al. (Feb. 1994). "Heterogeneity of Human IgG Fc receptors," Immunomethods 4(1):25-34.
Caron, P.C. et al. (Oct. 1, 1992). "Engineering Humanized Dimeric Forms of IgG Are More Effective Antibodies," J. Exp Med. 176:1191-1195.
Carter, P. et al. (Feb. 1992). "High Level Escherichia coli Expression and Production of a Bivalent Humanized Antibody Fragment," Bio/Technology 10:163-167.
Carter, P. et al. (May 1992). "Humanization of an Anti-p185HER2 Antibody for Human Cancer Therapy," Proc. Natl. Acad. Sci. USA 89:4285-4289.
Chen, J. et al. (Jul. 9, 1999). "Chaperone Activity of DsbC*," The Journal of Biological Chemistry 274(28):19601-19605.
Chen, Y. et al. (1999). "Selection and Analysis of an Optimized Anti-VEGF Antibody: Crystal Structure of an Affinity-Matured Fab in Complex With Antigen," J. Mol. Biol 293:865-881.
Chothia, C. et al. (Aug. 20, 1987). "Canonical Structures for the Hypervariable Regions of Immunoglobulins," J. Mol. Biol. 196(4):901-917.
Chowdhury, P.S. (2008). "Engineering Hot Spots for Affinity Enhancement of Antibodies," Methods Mol. Biol. 207:179-196.
Clackson, T. et al. (Aug. 15, 1991). "Making Antibody Fragments Using Phage Display Libraries," Nature 352:624-628.
Clynes, R. et al. (Jan. 1998). "Fc Receptors are Required in Passive and Active Immunity to Melanoma," Proc. Natl. Acad. Sci. U.S.A. 95:652-656.
Cole, S.P.C. et al. (1985). "The EBV-Hybridoma Technique and its Applicaton to Human Lung Cancer," in Monoclonal Antibodies and Cancer Therapy, Alan R. Liss, p. 77-96.
Conrath, K.E. et al. (Mar. 9, 2001). "Camel Single-domain Antibodies as Modular Building Units in Bispecific and Bivalent Antibody Constructs" J. Biol. Chem. 276(10):7346-7350.
Cragg, M.S. et al. (Apr. 1, 2004). "Antibody Specificity Controls In Vivo Effector Mechanisms of Anti-CD20 Reagents," Blood 103(7):2738-2743.
Cragg, M.S., et al. (2003). "Complement-Mediated Lysis by Anti-CD20 Mab Correlates With Segregation Into Lipid Rafts," Blood 101(3):1045-1052.
Cunningham, B.C. et al. (Jun. 2, 1989). "High-Resolution Epitope Mapping of hGH-Receptor Interactions by Alanine-Scanning Mutagenesis," Science 244:1081-1085.
Dall'Acqua, W.F. et al. (2005). "Antibody Humanization by Framework Shuffling," Methods 36:43-60.
Davies, J. et al. (1996). "Single Antibody Domains as Small Recognition Units: Design and In Vitro Antigen Selection of Camelized, Human VH Domains with Improved Protein Stability," Protein Engineering 9(6):531-537.
Davies, J. et al. (Feb. 21, 1994). "'Camelising' Human Antibody Fragments: NMR Studies on VH Domains," FEBS Letters 339(3):285-290.
Daëron, M. (1997). "Fc Receptor Biology," Ann. Rev. Immunol. 15:203-234.
De Haas, M. et al. (Oct. 1995). "Fc Gamma receptors of Phagocytes," J. Lab. Clin. Med. 126:330-341.
Duncan, A.R. et al. (Apr. 21, 1988). "The Binding Site for C1q on IgG," Nature 322:738-740.
Fan, G. et al. (2015). "Bispecific Antibodies and their Applications," J. Hematol & Oncol. 8(130):1-14.

(56) References Cited

OTHER PUBLICATIONS

Fellouse, F.A. et al. (Aug. 24, 2004). "Synthetic Antibodies from a Four-Amino-Acid Code: A Dominant Role for Tyrosine in Antigen Recognition," Proc. Natl. Acad. Sci. USA 101(34):12467-12472.
Fishwild, D.M. et al. (Jul. 1996). "High-Avidity Human IgGK Monoclonal Antibodies from a Novel Strain of Minilocus Transgenic Mice," Nature Biotechnol. 14:845-851.
Fulkerson, P.C. et al. (2013, e-pub. Jan. 21, 2013). "Targeting Eosinophils in Allergy, Inflammation and Beyond," Nat Rev Drug Discov 12(2):117-129, 23 pages.
Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.
Geering, B. et al. (Feb. 2015). "Synthetic Immunology: Modulating the Human Immune System," Trends Biotechnol. 33(2):65-79.
Ghetie, V. et al. (1997). "Increasing the Serum Persistence of an IgG Fragment by Random Mutagenesis," Nat Biotech 15:637-640.
Ghetie, V. et al. (Dec. 1997). "FcRn: the MHC Class I-related Receptor That is More Than an IgG Transporter," Immunol. Today 18(12):592-598.
Goding, J.W. (1986). "Production of Monoclonal Antibodies," Chapter 3 in Monoclonal Antibodies: Principles and Practice, Academic Press, New York, pp. 59-103.
Graham, F.L. et al. (1977). "Characteristics of a Human Cell Line Transformed By DNA From Human Adenovirus Type 5," Journal General Virology 36(1):59-74.
Greenberg, A.S. et al. (Mar. 9, 1995). "A New Antigen Receptor Gene Family That Undergoes Rearrangement and Extensive Somatic Diversification in Sharks" Nature 374(6518):168-173.
Griffith, A.D. et al. (1993). "Human Anti-Self Antibodies with High Specificity from Phage Display Libraries," EMBO J. 12(2):;;;;;;;;;;;725-734.
Gruber, M. et al. (1994). "Efficient Tumor Cell Lysis Mediated by a Bispecific Single Chain Antibody Expressed in *Escherichia coli*," J. Immunol. 152:5368-5374.
Guss, B. et al. (Jul. 1986). "Structure of the IgG-Binding Regions of Streptococcal Protein G," EMBO J. 5(7):1567-1575.
Guyer, R.L. et al. (Aug. 1976). "Immunoglobulin Binding by Mouse Intestinal Epithelial Cell Receptors," J. Immunol. 117(2):587-593.
Ham, R.G. et al. (1979). "Media and Growth Requirements," Meth. Enzymol. 58:44-93.
Hamers-Casterman, C. et al. (Jun. 3, 1993). "Naturally Occurring Antibodies Devoid of Light Chains," Nature 363(6428):446-448.
Hammerling, G. et al. (1981). "Monoclonal Antibodies and T-Cell Hybridomas," in Monoclonal Antibodies and T-Cell Hybridomas, Elsevier/North Holland Biomedical Press, New York, pp. 563-586.
Hara, H. et al. (1996) "Overproduction of Penicillin-Binding Protein 7 Suppresses Thermosensitive Grovvth Defect at Low Osmolarity Due to an Spr Mutation of *Escherichia coli*," Microhial Drug Resistance 2(1):63-72.
Harris, W.J. (1995). "Production of Humanized Monoclonal and Antibodies for in vivo Imaging and Therapy," Biochem. Soc. Transactions 23:1035-1038.
Hassanzadeh-Ghassabeh, G. et al. (2013, e-pub. Jun. 4, 2013). "Nanobodies and their Potential Applications," Nanomedicine (Lond) 8(6):1013-1026.
Hawkins, R.E. et al. (1992). "Selection of Phage Antibodies by Binding Affinity: Mimicking Affinity Maturations," J. Mol. Biol. 226:889-896.
Hellstrom, I. et al. (Mar. 1985). "Strong Antitumor Activities of IgG3 Antibodies to a Human Melanoma-associated Ganglioside," Proc. Natl. Acad. Sci. USA 82:1499-1502.
Hellstrom, I. et al. (Sep. 1986). "Antitumor Effects of L6, an IgG2a Antibody That Reacts With Most Human Carcinomas," Proc. Natl. Acad. Sci. USA 83:7059-7063.
Hinton, P.R. et al. (Feb. 20, 2004). "Engineered Human IgG Antibodies with Longer Serum Half-lives in Primates," J. Biol. Chem. 279(8):6213-6216.

Hmila, I. et al. (Aug. 2008, e-pub. Jul. 9, 2008). "VHH Bivalent Domains and Chimeric Heavy Chain-Only Antibodies With High Neutralizing Efficacy for Scorpion Toxin Aahi," Molecular Immunology 45(14):3847-3856.
Holliger, P. et al. (Jul. 1993). "Diabodies: Small Bivalent and Bispecific Antibody Fragments," Proc. Natl. Acad. Sci. Usa 90:6444-6448.
Holt, L. et al. (Nov. 2003) "Domain Antibodies: Proteins for Therapy," Trends in Biotechnology 21(11):484-490.
Hongo, J.A.S. et al. (1995). "Development and Characterization of Murine Monoclonal Antibodies to the Latency-Associated Peptide of Transforming Growth Factor Beta1," Hybridoma, 14(3):253-260.
Hoogenboom, H.R. (2002). "Overview of Antibody Phage-Display Technology and its Applications," in Chapter 1 of Methods in Molecular Biology, O'Brien, P.M. (ed.) et al., Humana Press Inc., Totowa, NJ, 178:1-37.
Hoogenboom, H.R. et al. (Sep. 20, 1992). "By-Passing Immunisation Human Antibodies From Synthetic Repertoires of Germline VH Gene Segments Rearranged In Vitro," J. Mol. Biol. 227(2):381-388.
Hudson, P.J. et al. (Jan. 2003). "Engineered Antibodies," Nature Medicine 9(1):129-134.
Hurle, M.R. et al. (1994). "Protein Engineering Techniques for Antibody Humanization," Curr. Op. Biotech. 5(4):428-433.
Idusogie, E.E. et al. (2000). "Mapping of the C1q Binding Site on Rituxan, a Chimeric Antibody With a Human IgG1 Fc," J. Immunol. 164:4178-4184.
International Preliminary Report on Patentability dated Apr. 16, 2019, for PCT Patent Application No. PCT/CN2017/105506, filed Oct. 10, 2017, 7 pages.
International Preliminary Report on Patentability dated Apr. 25, 2019, for PCT Patent Application No. PCT/CN2016/101777, filed Oct. 11, 2016, 9 pages.
International Preliminary Report on Patentability dated Jan. 22, 2019, for PCT Patent Application No. PCT/CN2016/090703, filed Jul. 20, 2016, 6 pages.
International Preliminary Report on Patentability dated Jan. 22, 2019, for PCT Patent Application No. PCT/CN2017/093644, filed Jul. 20, 2017, 6 pages.
International Search Report dated Apr. 12, 2017, for PCT Patent Application No. PCT/CN2016/090703, filed Jul. 20, 2016, 7 pages.
International Search Report dated Jan. 19, 2018, for PCT Patent Application No. PCT/CN2017/105506, filed Oct. 10, 2017, 6 pages.
International Search Report dated Jul. 11, 2017, for PCT Patent Application No. PCT/CN2016/101777, filed Oct. 11, 2016, 7 pages.
International Search Report dated Oct. 11, 2017, for PCT Patent Application No. PCT/CN2017/093644, filed Jul. 20, 2017, 7 pages.
Iwai, Y. et al. (Feb. 2005, e-pub. Dec. 20, 2004). "PD-1 Blockade Inhibits Hematogenous Spread of Poorly Immunogenic Tumor Cells by Enhanced Recruitment of Effector T Cells," International Immunology 17(2):133-144.
Jackson, J.R. et al. (Apr. 1, 1995). "In Vitro Antibody Maturation. Improvement of A High Affinity, Neutralizing Antibody Against IL-1 Beta," J. Immunol. 154(7):3310-3319.
Jakobovits, A. et al. (Mar. 18, 1993). "Germ-Line Transmission and Expression of a Human-Derived Yeast Artificial Chromosome," Nature 362:255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90:2551-2555.
Janssens, R. et al. (Oct. 10, 2006). "Generation of Heavy-Chain-Only Antibodies in Mice," Proc. Natl. Acad. Sci. USA 103(41):15130-15135.
Jin, H. (Dec. 31, 2013, e-pub. Apr. 23, 2015). "Construction and Characterization of a CTLA-4-Targeted scFv-Melittin Fusion Protein as a Potential Immunosuppressive Agent for Organ Transplant," Cell Biochemistry and Biophysics 3(67):1067-1074.
Johnson, G. et al. (2003). "The Kabat Database and a Bioinformatics Example," Methods in Molecular Biology 248:11-25, 15 pages.
Johnson, K.S. et al. (1993). "Human Antibody Engineering," Current Opinion in Structural Biology 3:564-571.

(56) References Cited

OTHER PUBLICATIONS

Jones, A.J.S. (1993). "Analysis of Polypeptides and Proteins," Adv. Drug Delivery Rev. 10:29-90.

Jones, P. et al. (May 29, 1986). "Replacing the Complementarity-Determining Regions in a Human Antibody With Those From a Mouse," Nature 321:522-525.

Kam, N.W.S. et al. (Aug. 16, 2005). "Carbon Nanotubes as Multifunctional Biological Transporters and Near-Infrared Agents for Selective Cancer Cell Destruction," PNAS 102(33):11600-11605, 6 pages.

Kanda, Y. et al. (Jul. 5, 2006, e-pub. Apr. 11, 2006). "Comparison of Cell Line for Stable Production of Fucose-Negative Antibodies with Enhanced ADCC," Biotechnol. Bioeng. 94(4):680-688.

Kashmiri, S.V. et al. (2005). "SDR grafting—A New Approach to Antibody Humanization," Methods 36:25-34.

Kim, J-K. et al. (1994). "Localization of the Site of the Murine IgGI Molecule That is Involved in Binding to the Murine Intestinal Fc Receptor," Eur. J. Immunol. 24:2429-2434.

Klimka, A. et al. (2000). "Human Anti-CD30 Recombinant Antibodies by Guided Phage Antibody Selection Using Cell Panning," Br. J. Cancer 83(2):252-260.

Kohler, G. et al. (Aug. 7, 1975) "Continuous Cultures of Fused Cells Secreting Antibody of Predefined Specificity," Nature 256:495-497.

Kostelny, S.A. et al. (Mar. 1, 1992). "Formation of a Bispecific Antibody by the Use of Leucine Zippers," J. Immunol. 148(5):1547-1553.

Kozbor, D. (Dec. 1984). "A Human Hybrid Myeloma for Production of Human Monoclonal Antibodies," J. Immunol. 133(6):3001-3005.

Lauwereys, M. et al. (Jul. 1, 1998). "Potent Enzyme Inhibitors Derived From Dromedary Heavy-Chain Antibodies," The EMBO Journal 17(13):3512-3520.

Lee, C.V. et al. (2004). "Bivalent Antibody Phage Display Mimics Natural Immunoglobulin," .J. Immunol. Methods 284(1-2):119-132.

Lee, C.V. et al. (2004). "High-Affinity Human Antibodies From Phage-Displayed Synthetic Fab Libraries With a Single Framework Scaffold," J. Mol. Biol. 340:1073-1093.

Li, L. et al. (Nov./Dec. 2015). "A Novel Bispecific Antibody, S-Fab, Induces Potent Cancer Cell Killing", J. of Immunotherapy 38(9):350-356.

Li, A. et al. (Apr. 26, 2016). "A Single-Domain Antibody-Linked Fab Bispecific Antibody Her2-S-Fab Has Potent Cytotoxicity Against Her2-Expressing Tumor Cells," AMB Express 6(32):1-8.

Li, J. et al. (Mar. 7, 2006). "Human Antibodies for Immunotherapy Development Generated via a Human B Cell Hybridoma Technology," Proc. Natl. Acad. Sci. USA 103:3557-3562, 6 pages.

Lindmark, R. et al. (1983). "Binding of Immunoglobulins to Protein A and Immunoglobulin Levels in Mammalian Sera," J. Immunol. Meth. 62:1-13.

Lonberg, N. (Sep. 2005). "Human Antibodies From Transgenic Animals," Nat. Biotech. 23(9):1117-1125.

Lonberg, N. et al. (1995, e-pub. Jul. 10, 2009). "Human Antibodies From Transgenic Mice," Int. Rev. Immunol. 13(1):65-93.

Lonberg, N. et al. (2008, e-pub. Jul. 21, 2008). "Fully Human Antibodies From Transgenic Mouse and Phage Display Platforms," Curr. Opin. Immunol. 20:450-459.

Lonberg, N. et al. (Apr. 28, 1994). "Antigen-Specific Human Antibodies From Mice Comprising Four Distinct Genetic Modifications," Nature 368(6474):856-859.

Marks, J.D. et al. (1991). "By-Passing Immunization Human Antibodies from V-gene Libraries Displayed on Phage," J. Mol. Biol. 222:581-597.

Marks, J.D. et al. (2004) "Selection of Human Antibodies from Phage Display Libraries," Chapter 8 in Methods in Molecular Biology, LO, B.K.C. (ed.), Humana Press Inc., Totowa, NJ, 248:161-176, 29 pages.

Marks, J.D. et al. (Jul. 1992). "By-Passing Immunization: Building High Affinity Human Antibodies by Chain Shuffling," Bio/Technology 10:779-783.

Mather, J.P. (1980). "Establishment and Characterization of Two Distinct Mouse Testicular Epithelial Cell Lines," Biol. Reprod. 23:243-251.

Mather, J.P. et al. (1982). "Culture of Testicular Cells in Hormone-Supplemented Serum-Free Medium," Annals N.Y. Acad. Sci. 383:44-68.

McCafferty, J. et al. (Dec. 6, 1990). "Phage Antibodies: Filamentous Phage Displaying Antibody Variable Domains," Nature 348:552-554.

Milstein. C. et al. (Oct. 6, 1983). "Hybrid Hybridomas and Their Use in Immunohistochemistry," Nature 305:537-539.

Molhoj, M. (Sep. 2011). "Ang2A/EGF CrossMAbCH1-CL, a novel bispecific monovalent human IgG1 format aiming at neutralizing Ang2 and VEGF-A to treat solid tumors", Presentations Outline in CrossMAB Technology, 35 pages.

Mordenti, J. et al. (1989). "The Use of Interspecies Scaling in Toxicokinetics," Chapter 4 in Toxicokinetics and New Drug Development, Yacobi A. ed et al.; Pergamon Press, New York, pp. 42-96.

Morimoto, K. et al. (1992). "Single-Step Purification of F(AB')2 Fragments of Mouse Monoclonal Antibodies (Immunoglobulins G1) by Hydrophobic Interaction High Performance Liquid Chromatography Using TSKgel Phenyl-5PW," J. Biochem. Biophys. Method 24:107-117.

Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.

Morrison, S.L. (Apr. 28, 1994). "Success in Specification," Nature 368:812-813.

Munson, P.J. et al. (1980). "Ligand: A Versatile Computerize Approach for Characterization of Ligand-Binding Systems," Anal. Biochem. 107:220-239.

Murata, K.Y. (Aug. 1999). "Expression of the Costimulatory Molecule BB-1, the Ligands CTLA-4 and CD28, and their mRNA in Inflammatory Myopathies," Am. J. Pathol. 155(2):453-460.

Neuberger, M. (Jul. 1996) "Generating High-Avidity Human Mabs in Mice," Nature Biotechnology 14:826, 1 page.

Ni, J. (Oct. 23, 2006). "Research Progress and Future Perspectives in Antibodmics and Antibodomic Drugs," J. General Review 26(4):265-268, 3 pages.

Okazaki, A. et al. (Mar. 5, 2004). "Fucose Depletion From Human IgG1 Oligosaccharide Enhances Binding Enthalpy and Association Rate Between IgG1 and FcγRIIIa," J. Mol. Biol. 336(5):1239-1249.

Osbourn, J. et al. (2005). "From Rodent Regents to Human Therapeutics Using Antibody Guided Selection," Methods 36:61-68.

Padlan, E.D. (1991). "A Possible Procedure for Reducing the Immunogenicity of Antibody Variable Domains While Preserving Their Ligand-Binding Properties," Mol. Immunol. 28(4/5):489-498.

Pardon, E. et al. (Mar. 2014, e-pub. Feb. 27, 2014). "A General Protocol for the Generation of Nanobodies for Structural Biology," Nature Protocol 9(3):674-693, 40 pages.

Perrin, P.J. et al. (Aug. 15, 1996). "CTLA-4 Blockade Enhances Clinical Disease and Cytokine Production During Experimental Allergic Encephalomyelitis," The Journal of Immunology 157(4):1333-1336.

Petkova, S.B. et al. (Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18(12):1759-1769.

Plückthun, A. (1992). "Mono- and Bivalent Antibody Fragments Producted in *Escherichia coli*: Engineering, Folding and Antigen Binding," Immunol. Revs. 130:151-188.

Plückthun, A. (1994) "Antibodies from *Escherichia coli*," Chapter 11 in Handbook of Experimental Pharmacology 113:269-315.

Presta, L.G. (1992). "Antibody Engineering," Current Opinion in Structural Biology 2:593-596.

Presta, L.G. et al. (Oct. 15, 1997). "Humanization of an Anti-Vascular Endothelial Growth Factor Monoclonal Antibody for the Therapy of Solid Tumors and Other Disorders," Cancer Res. 57:4593-4599.

Presta, L.G. et al. (Sep. 1, 1993). "Humanization of an Antibody Directed Against IgE," J. Immunol. 151(5):2623-2632.

(56) References Cited

OTHER PUBLICATIONS

Proba, K. et al. (1995). "Functional Antibody Single-chain Fragments From the Cytoplasm of *Escherichia coli* Influence of Thioredoxin Reductase (trxb)," Gene 159(2):203-207.

Queen, C. et al. (Dec. 1989). "A Humanized Antibody That Binds to the Interleukin 2 Receptor," Proc. Natl Acad. Sci. USA 86:10029-10033.

Ramm, K. et al. (Jun. 2, 2000). "The Periplasmic *Escherichia coli* Peptidylprolyl cis,Trans-Isomerase FkpA," The Journal of Biological Chemistry 275(22):17106-17113.

Ravetch, J.V. et al. (1991). "Fc Receptors," Annu. Rev. Immunol. 9:457-492.

Reyes, G.R. et al. (Jun. 17, 1982) "Expression of Human β-interferon cDNA Under the Control of a Thymidine Kinase Promoter from Herpes Simplex Virus," Nature 297:598-601.

Riechmann, L. (Jun. 28, 1996). "Rearrangement of the Former VL Interface in the Solution Structure of a Camelised, Single Antibody VH Domain," Journal of Molecular Biology 259(5):957-969.

Riechmann, L. et al. (Dec. 10, 1999). "Single Domain Antibodies: Comparison of Camel VH and Camelised Human VH Domains," Journal of Immunological Methods 231(1-2):25-38.

Riechmann, L. et al. (Mar. 1988). "Reshaping Human Antibodies for Therapy," Nature 332:323-329.

Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.

Rosenberg, S.A. et al. (Dec. 22, 1988). "Use of Tumor-Infiltrating Lymphocytes and Interleukin-2 in the Immunotherapy of Patients With Metastatic Melanoma. A Preliminary Report," N Engl J Med. 319(25):1676-1680.

Rosok, M.J. et al. (Sep. 13, 1996). "A Combinatorial Library Strategy for the Rapid Humanization of Anticarcinoma BR96 Fab," J. Biol. Chem. 271(37):22611-22618.

Schier, R. et al. (1995). "Identification of Functional and Structural Amino-Acid Residues by Parsimonious Mutagenesis," Gene 169:147-155.

Shalaby, M.R. et al. (Jan. 1, 1992). "Development of Humanized Bispecific Antibodies Reactive With Cytotoxic Lymphocytes and Tumor Cells Overexpressing the HER2 Protooncogene," J. Exp. Med. 175:217-225.

Sheriff, S. et al. (Sep. 1996). "Redefining the Minimal Antigen-Binding Fragment," Nature Struct. Biol. 3(9):733-736.

Shields, R.L. et al. (Mar. 2, 2001). "High Resolution Mapping of the Binding Site on Human IgG1 for FcγRI, FcγRII, FcγRIII, and FcRn and Design of IgG1 Variants With Improved Binding to the FcγR," J. Biol.Chem. 276(9):6591-6604.

Shinkawa, T. et al. (Jan. 31, 2003). "The Absence of Fucose but Not the Presence of Galactose or Bisecting N-Acetylglucosamine of Human IgG1 Complex-Type Oligosaccharides Shows the Critical Role of Enhancing Antibody-Dependent Cellular Cytotoxicity," Journal of Biological Chemistry 278(5):3466-3473.

Shopes, B. et al. (May 1, 1992). "A Genetically Engineered Human IgG Mutant With Enhanced Cytolytic Activity," J. Imniunol. 148:2918-2922.

Sidhu, S.S. et al. (2004). "Phage-Displayed Antibody Libraries of Synthetic Heavy Chain Complementarity Determining Regions," J. Mol. Biol. 338(2):299-310.

Siebenlist, U. et al. (Jun. 1980). "*E. coli* RNA Polymerase Interacts Homologously With Two Different Promoters," Cell 20(2):269-281.

Simmons, L.C. et al. (May 1, 2002). "Expression of Full-Length Immunoglobulins in *Escherichia coli*: Rapid and Efficient Production of Aglycosylaled Antibodies," J. Immunol. Meth. 263(1-2):133-147.

Sims, M.J. et al. (Aug. 15, 1993). "A Humanized CD18 Antibody Can Block Function Without Cell Destruction," J. Immunol. 151:2296-2308.

Skerra, A. (1993) "Bacterial Expression of Immunoglobulin Fragments," Current Opinion in Immunology 5:256-262.

Stamova, S. et al. (Jul. 18, 2012). "Cancer Immunotherapy by Retargeting of Immune Effector Cells via Recombinant Bispecific Antibody Constructs," Antibodies 1(2):172-198.

Stevenson, G.T. et al. (Mar. 1989). "A Chimeric Antibody With Dual Fc Regions (bisFabFc) Prepared by Manipulations at the IgG Hinge," Anti-cancer Drug Des.3(4):219-230.

Streltsov, V.A. (Nov. 2005). "Structure of a Shark Ignar Antibody Variable Domain and Modeling of an Early-Developmental Isotype," Protein Sci. 14:2901-2909.

Suresh, M.R. et al. (1986). "Bispecific Monoclonal Antibodies From Hybrid Hybridomas," Methods in Enzymology 121:210-228, 19 pages.

Transue, T.R. et al. (1998). "Camel Single-Domain Antibody Inhibits Enzyme by Mimicking Carbohydrate Substrate," Proteins 32(4):515-522.

Traunecker, A. et al. (1991). "Bispecific Single Chain Molecules (Janusins) Target Cytotoxic Lymphocytes on HIV Infected Cells," EMBO J. 10(12):3655-3659.

Turnis, M.E. (2012, e-pub. Oct. 1, 2012). "Combinatorial Immunotherapy PD-1 May Not Be LAG-ing Behind Any More, Combinatorial Immunotherapy", OncoImmunology 1(7):1172-1174.

Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.

Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.

Van Der Linden, R. (Jun. 23, 2000, e-pub. Jun. 13, 2000). "Induction of Immune Responses and Molecular Cloning of the Heavy Chain Antibody Repertoire of Lama Glama," J. Immunol. Methods 240(1-2):185-195.

Van Dijk, M.A. et al. (Aug. 2001). "Human Antibodies as Next Generation Therapeutics," Curr. Opin. Chem. Biology 5(4):368-374.

Vaswani, S.K. et al. (Aug. 1998) "Humanized Antibodies as Potential Therapeutic Drugs," Annals of Allergy, Asthma, & Immunology 81:105-115.

Verhoeyen, M. et al. (Mar. 25, 1988). "Reshaping Human Antibodies: Grafting an Antilysozyme Activity," Science 239(4857):1534-1536.

Vollmers, H.P. et al. (2005) "Death by Stress: Natural IgM-induced Apoptosis," Methods Find Exp Clin Pharmacol. 27(3):1-7.

Vollmers, H.P. et al. (2005). "The 'Early Birds': Natural IgM Antibodies and Immune Surveillance," Histology and Histopathology, 20(3):927-937.

Walunas, T.L. et al. (Jun. 1996). "CTLA-4 Ligation Blocks CD28-Dependent T Cell Activation," The Journal of Experimental Medicine 183(6):2541-2550.

Ward, E.S. et al. (Oct. 12, 1989). "Binding Activities of a Repertoire of Single Immunoglobulin Variable Domains Secreted From *Escherichia coli*," Nature 341(6242): 544-546.

Waterhouse, P. et al. (1993). "Combinatorial Infection and In Vivo Recombination: A Strategy for Making Large Phage Antibody Repertoires," Nucleic Acids Research 21(9):2265-2266.

Weidle, U.H. et al. (Jan.-Feb. 2013). "The Intriguing Options of Multispecific Antibody Formats for Treatment of Cancer," Cancer Genomics Proteomics 10(1):1-18.

Weidner K. M. et al. (Nov. 1, 2010). "Anti-Angiogenic Activity of a Tetravalent Bispecific Antibody (TAvi6) Targeting VEGF and Angiopoietin-211," Blood 116(21):1746 (abstract 4303), 2 pages.

Wesolowski, J. et al. (Aug. 2009, e-pub. Jun. 16, 2009). "Single Domain Antibodies: Promising Experimental and Therapeutic Tools in Infection and Immunity," Med Microbiol Immunol 198:157-174.

Winter, G. el al. (1994). "Making Antibodies by Phage Display Technology," Ann. Rev. Immunol. 12:433-455.

Wolff, E.A. et al. (Jun. 1, 1993). "Monoclonal Antibody Homodimers: Enhanced Antitumor Activity in Nude Mice," Can Res 53:2560-2565.

Wright, A. et al. (Jan. 1997). "Effect of Glycosylation on Antibody Function: Implications for Genetics Engineering," Trends Biotechnol. 15:26-32.

(56) References Cited

OTHER PUBLICATIONS

Written Opinion of the International Searching Authority dated Apr. 12, 2017, for PCT Patent Application No. PCT/CN2016/090703, filed Jul. 20, 2016, 5 pages.
Written Opinion of the International Searching Authority dated Jan. 19, 2018, for PCT Patent Application No. PCT/CN2017/105506, filed Oct. 10, 2017, 6 pages.
Written Opinion of the International Searching Authority dated Jul. 11, 2017, for PCT Patent Application No. PCT/CN2016/101777, filed Oct. 11, 2016, 7 pages.
Written Opinion of the International Searching Authority dated Oct. 11, 2017, for PCT Patent Application No. PCT/CN2017/093644, filed Jul. 20, 2017, 5 pages.
Xu, J.L. et al. (Jul. 2000). "Diversity in the CDR3 Region of VH is Sufficient for Most Antibody Specificities," Immunity 13:37-45.
Yamane-Ohnuki, N. et al. (2004, e-pub. Aug. 6, 2004). "Establishment of FUT8 Knockout Chinese hamster Ovary Cells: An Ideal Host Cell Line for Producing Completely Defucosylated Antibodies With Enhances Antibody-Dependent Cellular Cytotoxicity," Biotech. Bioeng. 87:614-622.
Yaniv, M. (May 6, 1982). "Enhancing Elements for Activation of Eukaryotic Promoters," Nature 297:17-18.
Yansura, D.G. et al. (1992). "Nucleotide Sequence Selection for Increased Expression of Heterologous Genes in *Escherichia coli*," Methods: A Companion to Methods in Enzymol 4:151-158.
Yelton, D.E. et al. (1995). "Affinity Maturation of the BR96 Anti-Carcinoma Antibody by Codon-Based Mutagenesis," J. Immunol. 155:1994-2004.
Zapata, G. et al. (1995). "Engineering Linear F(ab')2 Fragments for Efficient Production in *Escherichia coli* and Enhanced Antiproliferative Activity," Protein Engineering 8(10):1057-1062.
Zhu, Z. et al. (1997). "Remodeling Domain Interfaces to Enhance Heterodimer Formation," Protein Science 6:781-788.
Fromentin, R. et al. (Jul. 14, 2016). "CD4+ T Cells Expressing PD-1, TIGIT and LAG-3 Contribute to HIV Persistence during Art," PLoS Athogens 12(7):1-19.
International Preliminary Report on Patentability dated Jul. 14, 2020, for PCT Patent Application No. PCT/CN2019/070873, filed Jan. 8, 2019, 7 pages.
International Search Report and Written Opinion dated Apr. 11, 2019, for PCT Patent Application No. PCT/CN2019/070873, filed Jan. 8, 2019, 15 pages.
U.S. Appl. No. 16/960,521, filed Jul. 7, 2020, by Zhang et al.(U.S. Patent Application document is not submitted herewith pursuant to the waiver of 37 C.F.R. § 1.98(a)(2)(iii) issued by the Office on Sep. 21, 2004.).
Anderson, A. C. et al. (May 17, 2016). "Lag-3, Tim-3, and TIGIT: Co-Inhibitory Receptors with Specialized Functions in Immune Regulation," Immunity 44(5):989-1004.
Brown, M. et al. (1996) "Tolerance to Single, but Not Multiple, Amino Acid Replacements in Antibody VH CDR2," J. Immunol. 156:3285-3291.
Vajdos, F. et al. (2002) "Comprehensive Functional Maps of the Antigen Binding Site of an Anti-ErbB2 Antibody Obtained with Shotgun Scanning Mutagenesis," J. Mol. Biol. 320:415-428.

* cited by examiner

```
                            SEQUENCE LISTING

<160> NUMBER OF SEQ ID NOS: 13

<210> SEQ ID NO 1
<211> LENGTH: 9
<212> TYPE: PRT
<213> ORGANISM: Artificial Sequence
<220> FEATURE:
<223> OTHER INFORMATION: Synthetic Construct

<400> SEQUENCE: 1

Gly Gly Gly Gly Ser Gly Gly Gly Ser
1               5

<210> SEQ ID NO 2
<211> LENGTH: 120
<212> TYPE: PRT
<213> ORGANISM: Artificial Sequence
<220> FEATURE:
<223> OTHER INFORMATION: Synthetic Construct

<400> SEQUENCE: 2

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 3
<211> LENGTH: 111
<212> TYPE: PRT
<213> ORGANISM: Artificial Sequence
<220> FEATURE:
<223> OTHER INFORMATION: Synthetic Construct

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
```

-continued

```
                 65                  70                  75                  80

Ser Leu Glu Pro Glu Asp Phe Ala Val Tyr Tyr Cys Gln His Ser Arg
                 85                  90                  95

Asp Leu Pro Leu Thr Phe Gly Gly Gly Thr Lys Val Glu Ile Lys
                100                 105                 110

<210> SEQ ID NO 4
<211> LENGTH: 447
<212> TYPE: PRT
<213> ORGANISM: Artificial Sequence
<220> FEATURE:
<223> OTHER INFORMATION: Synthetic Construct

<400> SEQUENCE: 4

Gln Val Gln Leu Val Gln Ser Gly Val Glu Val Lys Lys Pro Gly Ala
1               5                  10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
```

```
            325                 330                 335
Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
            435                 440                 445
```

<210> SEQ ID NO 5
<211> LENGTH: 218
<212> TYPE: PRT
<213> ORGANISM: Artificial Sequence
<220> FEATURE:
<223> OTHER INFORMATION: Synthetic Construct

<400> SEQUENCE: 5

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 6
<211> LENGTH: 107
<212> TYPE: PRT

```
<213> ORGANISM: Artificial Sequence
<220> FEATURE:
<223> OTHER INFORMATION: Synthetic Construct

<400> SEQUENCE: 6

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 7
<211> LENGTH: 327
<212> TYPE: PRT
<213> ORGANISM: Artificial Sequence
<220> FEATURE:
<223> OTHER INFORMATION: Synthetic Construct

<400> SEQUENCE: 7

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220
```

-continued

```
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 8
<211> LENGTH: 15
<212> TYPE: PRT
<213> ORGANISM: Artificial Sequence
<220> FEATURE:
<223> OTHER INFORMATION: Synthetic Construct

<400> SEQUENCE: 8

Glu Pro Lys Ser Cys Asp Lys Thr His Thr Cys Pro Pro Cys Pro
1               5                   10                  15

<210> SEQ ID NO 9
<211> LENGTH: 2
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(2)
<223> OTHER INFORMATION: Can be present in repeats of one or more

<400> SEQUENCE: 9

Gly Ser
1

<210> SEQ ID NO 10
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(5)
<223> OTHER INFORMATION: Can be present in repeats of one or more

<400> SEQUENCE: 10

Gly Ser Gly Gly Ser
1               5

<210> SEQ ID NO 11
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(4)
<223> OTHER INFORMATION: Can be present in repeats of one or more
```

```
<400> SEQUENCE: 11

Gly Gly Gly Ser
1

<210> SEQ ID NO 12
<211> LENGTH: 15
<212> TYPE: PRT
<213> ORGANISM: Artificial Sequence
<220> FEATURE:
<223> OTHER INFORMATION: Synthetic Construct

<400> SEQUENCE: 12

Gly Gly Gly Gly Ser Gly Gly Gly Gly Ser Gly Gly Gly Gly Ser
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic Construct

<400> SEQUENCE: 13

Glu Pro Lys Ser Ser Asp Lys Thr His Thr Ser Pro Pro Ser Pro
1               5                   10                  15
```

MULTISPECIFIC ANTIGEN BINDING PROTEINS AND METHODS OF USE THEREOF

CROSS REFERENCE TO RELATED APPLICATIONS

This application is a national phase application under 35 U.S.C. § 371 of International Application No. PCT/CN2017/093644, filed Jul. 20, 2017, which claims priority benefit of International Patent Application No. PCT/CN2016/090703 filed Jul. 20, 2016, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 761422000200SEQLIST.txt, date recorded: Dec. 28, 2018, size: 14 KB).

FIELD OF THE INVENTION

The present invention relates to multispecific antigen binding proteins (MABPs) comprising at least one single-domain antibody and methods of use thereof.

BACKGROUND OF THE INVENTION

Monoclonal antibodies (mAbs) have been widely used as therapeutic agents to treat a variety of human diseases, such as cancer and autoimmune diseases. Currently, there are more than 30 monoclonal antibodies including murine, fully humanized, and chimeric antibodies that have been approved by the FDA for therapeutic use. Rituximab and trastuzumab are among the top-selling protein therapeutics against cancer. Recently, monoclonal antibodies targeting immune checkpoint molecules, such as ipilimumab (e.g., YERVOY®) and nivolumab (e.g., OPDIVO®), have shown encouraging clinical results by inducing T cell immunity against tumors. As many patients do not respond well to monotherapy approaches, monoclonal antibodies are often combined with other immunomodulatory approaches, such as monoclonal antibodies against other targets, to enhance their efficacy. For example, clinical studies have demonstrated that combination of nivolumab and ipilimumab results in improved rates of objective response among melanoma patients.

With the development of molecular cloning technology and growing knowledge of antibody engineering, many formats have evolved to increase the targeting capacity of therapeutic antibodies. Multispecific (such as bispecific) antibodies are designed to simultaneously modulate two or more therapeutic targets in order to provide enhanced therapeutic efficacy and broadened potential utility. It has been reported that bispecific antibodies can be more effective than simple combination of two monoclonal antibodies. A variety of multispecific antibody formats have been developed. For example, bispecific antibodies have been made by fusing antigen binding (Fab) fragments or single chain variable fragments (scFvs) to monoclonal antibodies (see, for example, Weidle et al. *Cancer Genomics & Proteomics* 2013; 10: 1-18). Bispecific T-cell engagers (BiTEs) have been developed using scFvs to bridge tumor cells with immune cells and form an immunological synapse by taking advantage of their relatively small size. Bispecific antibodies in the IgG format include asymmetric bispecific antibodies and homodimerized bispecific antibodies, all of which have an extended blood half-life and their own crystalline fragment (Fc)-mediated functions. Multispecific antibodies of different formats differ in size, are frequently produced by different technologies, and have different in vivo distribution, tissue penetration, and pharmacokinetic properties.

Despite their conceptual advantages, current bispecific antibodies are challenging to manufacture and develop as biologic drugs. As artificial constructs, bispecific antibodies cannot be produced by normal B-cells. Initial attempts to produce bispecific antibodies involved chemical conjugation of monospecific antibodies and fusion of mAb-expressing cells, but these approaches suffer from low efficiency and the necessity of purification from abundant side products. Advanced methods in protein engineering and molecular biology have enabled recombinant construction of a variety of new bispecific antibody formats. However, once adopted in these known engineered bispecific antibody formats, the individual components, such as scFvs and mAbs, lose their favorable biochemical and/or biophysical properties, serum half-life, and/or stability, resulting in poor efficacy, instability and high immunogenicity. See, for example, Fan G. et al. *J. Hematol & Oncol*, 2015; 8:130. Furthermore, many known bispecific antibody formats are associated with low expression levels that are impractical for industrial production. Thus, there remains a need for bispecific antibody platforms for practical production and development into biologic drugs.

Single-domain antibodies (sdAbs) are antibody fragments each having a single monomeric antibody variable domain. Despite their much smaller sizes than common monoclonal antibodies having two heavy chains and two light chains, sdAbs can bind antigens with similar affinity and specificity as mAbs. Used as building blocks, the sdAbs can be fused to IgG Fc domains to create IgG-like antibodies, including bivalent and bispecific antibodies (see, for example, Hmila I. et al. *Mol. Immunol*. 2008; 45: 3847-3856).

The disclosures of all publications, patents, patent applications and published patent applications referred to herein are hereby incorporated herein by reference in their entirety.

BRIEF SUMMARY OF THE INVENTION

The present application provides a multispecific antigen binding protein (MABP) comprising one or more single-domain antibodies (sdAbs) fused to a full-length four-chain antibody or an antigen binding fragment derived therefrom.

Accordingly, one aspect of the present application provides a MABP comprising: (a) a first antigen binding portion comprising a heavy chain variable domain ($V_H$) and a light chain variable domain ($V_L$), wherein the $V_H$ and $V_L$ together form an antigen-binding site that specifically binds a first epitope, and (b) a second antigen binding portion comprising a single-domain antibody (sdAb) that specifically binds a second epitope, wherein the first antigen binding portion and the second antigen binding portion are fused to each other. In some embodiments, the first epitope and the second epitope are from the same antigen. In some embodiments, the first epitope and the second epitope are from different antigens. In some embodiments, the MABP is bispecific.

In some embodiments according to any one of the MABPs described above, the first antigen binding portion is a full-length antibody consisting of two heavy chains and two light chains. In some embodiments, the first antigen binding portion is an antibody fragment comprising a heavy chain comprising the $V_H$ and a light chain comprising the $V_L$. In some embodiments, the second antigen binding portion comprises a single polypeptide chain. In some embodiments, the C terminus of the second antigen binding portion is fused to the N-terminus of at least one heavy chain of the first antigen binding portion. In some embodiments, the C terminus of the second antigen binding portion is fused to the N-terminus of at least one light chain of the first antigen binding portion. In some embodiments, the N terminus of the second antigen binding portion is fused to the C-terminus of at least one heavy chain of the first antigen binding portion. In some embodiments, the N terminus of the second antigen binding portion is fused to the C-terminus of at least one light chain of the first antigen binding portion. In some embodiments, the second antigen binding portion is a Fab-like domain comprising a first polypeptide chain comprising a first sdAb fused to a $C_H1$ domain, and a second polypeptide chain comprising a second sdAb fused to a $C_L$ domain.

In some embodiments according to any one of the MABPs described above, the first antigen binding portion comprises a human, humanized or chimeric antibody or antigen binding fragment thereof.

In some embodiments according to any one of the MABPs described above, the first antigen binding portion comprises an Fc region. In some embodiments, the second antigen binding portion is fused to the N-terminus of the Fc region. In some embodiments, the Fc region is an IgG1 Fc. In some embodiments, the Fc region is an IgG4 Fc, such as an IgG4 Fc having an S228P mutation.

In some embodiments according to any one of the MABPs described above, the first antigen binding portion and the second antigen binding portion are fused to each other via a peptide bond or a peptide linker. In some embodiments, the peptide linker is no more than about 30 (such as no more than about any one of 25, 20 or 15) amino acids long. In some embodiments, the peptide linker comprises the amino acid sequence of SEQ ID NO: 1, 8 or 13. In some embodiments, the first antigen binding portion and the second antigen binding portion are fused to each other chemically.

In some embodiments according to any one of the MABPs described above, the sdAb is a camelid, humanized, or human sdAb.

In some embodiments according to any one of the MABPs described above, the first epitope is from an immune checkpoint molecule. In some embodiments, the immune checkpoint molecule is selected from the group consisting of PD-1, PD-L1, PD-L2, CTLA-4, B7-H3, TIM-3, LAG-3, VISTA, ICOS, 4-1BB, OX40, GITR, and CD40. In some embodiments, the first antigen binding portion is an anti-PD-1 antibody or antigen binding fragment thereof. In some embodiments, the anti-PD-1 antibody is selected from the group consisting of pembrolizumab (e.g., KEYTRUDA®) and nivolumab (e.g., OPVIDO®). In some embodiments, the first antigen binding portion is an anti-PD-L1 antibody or antigen binding fragment thereof. In some embodiments, the anti-PD-L1 antibody is duravalumab or atezolizumab. In some embodiments, the sdAb specifically binds an immune checkpoint molecule, such as an immune checkpoint molecule selected from the group consisting of PD-1, PD-L1, PD-L2, CTLA-4, B7-H3, TIM-3, LAG-3, VISTA, ICOS, 4-1BB, OX40, GITR, and CD40. In some embodiments, the second antigen binding portion comprises an anti-CTLA-4 sdAb.

In some embodiments according to any one of the MABPs described above, the first epitope is from a tumor antigen. In some embodiments, the tumor antigen is selected from the group consisting of HER2, BRAF, EGFR, VEGFR2, CD20, RANKL, CD38, and CD52. In some embodiments, the first antigen binding portion is an anti-HER2 antibody or antigen binding fragment thereof. In some embodiments, the anti-HER2 antibody is trastuzumab. In some embodiments, the second antigen binding portion comprises an anti-CD3 sdAb.

In some embodiments according to any one of the MABPs described above, the first epitope is from an angiogenic factor. In some embodiments, the first antigen binding portion is an anti-Ang2 antibody or antigen binding fragment thereof, such as LC10. In some embodiments, the second epitope is from a second angiogenic factor. In some embodiments, the second antigen binding portion is an anti-VEGF sdAb.

In some embodiments according to any one of the MABPs described above, the first epitope is from a pro-inflammatory molecule. In some embodiments, the pro-inflammatory molecule is selected from the group consisting of IL-1β, TNF-α, IL-5, IL-6, IL-6R, and eotaxin-1. In some embodiments, the first antigen binding portion is an anti-TNF-α antibody or antigen binding fragment thereof. In some embodiments, the anti-TNF-α antibody is adalimumab. In some embodiments, the second antigen binding portion comprises an anti-IL-1β sdAb. In some embodiments, the first antigen binding portion is an anti-IL-5 antibody or antigen binding fragment thereof. In some embodiments, the anti-IL-5 antibody is mepolizumab. In some embodiments, the second antigen binding portion comprises an anti-eotaxin-1 sdAb.

In some embodiments according to any one of the MABPs described above, the MABP can be produced recombinantly, such as in mammalian cells (e.g., CHO cells), at an expression level of at least about 10 mg/L, such as at least about 10 mg/L, 15 mg/L, 50 mg/mL, or higher. In some embodiments, the MABP has a solubility of at least about 100 mg/mL, such as at least about 150 mg/mL, 200 mg/mL or higher. In some embodiments, the MABP has an aggregation onset temperature ($T_{agg}$) of at least about 65° C., such as about 65° C. to about 75° C. In some embodiments, the MABP has an unfolding midpoint temperature ($T_m$) of at least about 65° C., such as about 65° C. to about 75° C. In some embodiments, the MABP is stable for at least about one week at 25° C. at a concentration of at least about 50 mg/mL. In some embodiments, the MABP is stable for at least about one week at 37° C. at a concentration of at least about 50 mg/mL. In some embodiments, the MABP is stable after at least about 5 freeze-thaw cycles at a concentration of at least 50 mg/mL.

Another aspect of the present application provides a pharmaceutical composition comprising any one of the MABPs described above and a pharmaceutically acceptable carrier. In some embodiments, the concentration of the MABP is at least about 100 mg/mL, such as at least about 150 mg/mL, 200 mg/mL or higher.

Further provided in one aspect of the present application is a method of treating a disease in an individual, comprising administering to the individual an effective amount of any one of the pharmaceutical compositions described above. In some embodiments, the disease is a cancer. In some embodiments, the cancer is selected from the group consisting of breast cancer, renal cancer, melanoma, lung cancer, glioblastoma, head and neck cancer, prostate cancer, ovarian carcinoma, bladder carcinoma, and lymphoma. In some embodiments, the disease is an inflammatory or autoimmune disease. In some embodiments, the inflammatory or autoimmune disease is selected from the group consisting of arthritis (such as rheumatoid arthritis, juvenile idiopathic arthritis, psoriatic arthritis, ankylosing spondylitis, and arthritic ulcerative colitis), colitis, psoriasis, severe asthma, and moderate to severe Crohn's disease.

$V_L$-$C_L$; (2) $V_H$-$C_H1$-$C_H2$-$C_H3$-$V_H$H1; (3) $V_H$-$C_H1$-$C_H2$-$C_H3$-$V_H$H2; and (4) $V_L$-$C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, $V_H$H1 specifically binds the second epitope, and $V_H$H2 specifically binds the third epitope. In alternative formats, each sdAb may be omitted, or replaced with two identical or different sdAbs fused to each other. The monospecific full-length antibody may be replaced with a bispecific full-length antibody to further expand binding specificity.

Figure 8:
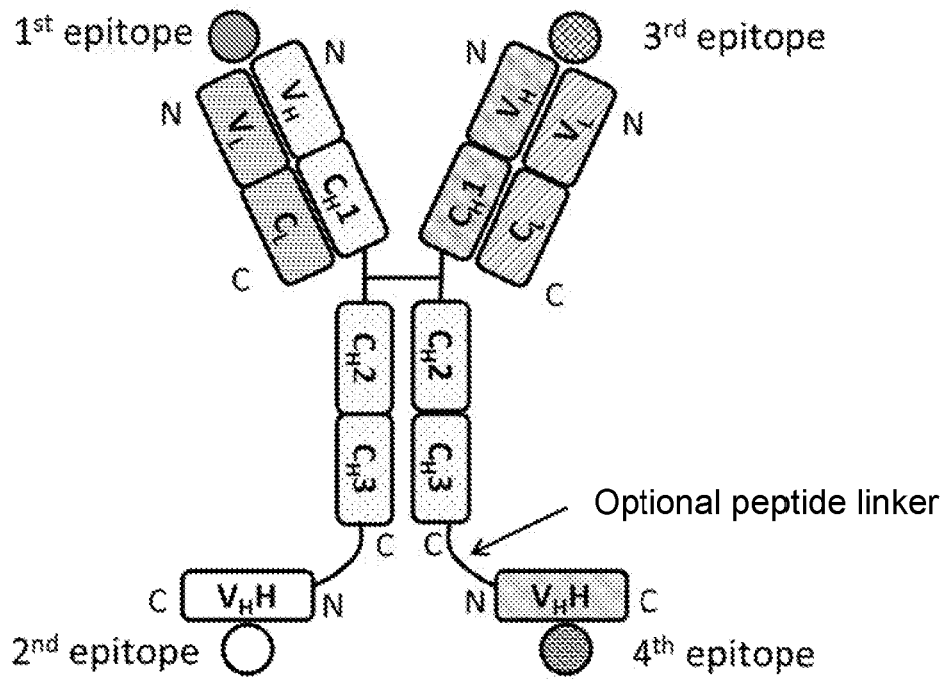

FIG. 8 depicts a schematic structure of an exemplary tetraspecific antigen binding protein comprising a bispecific full-length antibody having two heavy chains and two light chains, a first sdAb, and a second sdAb, wherein the N-terminus of each sdAb is fused to one heavy chain via an optional peptide linker. The full-length antibody has a first antigen binding site that specifically binds the first epitope, and a second antigen binding site that specifically binds the third epitope. The first sdAb specifically binds the second epitope. The second sdAb specifically binds the fourth epitope. For example, the tetraspecific antigen binding protein can consist of four polypeptide chains with structures from the N-terminus to the C-terminus as follows: (1) $V_L1$-$C_L$; (2) $V_H1$-$C_H1$-$C_H2$-$C_H3$-$V_H$H1; (3) $V_H2$-$C_H1$-$C_H2$-$C_H3$-$V_H$H2; and (4) $V_L2$-$C_L$, wherein $V_H1$ and $V_L1$ of polypeptide chains (1) and (2) forms an antigen binding site that specifically binds the first epitope, $V_H2$ and $V_L2$ of polypeptide chains (3) and (4) forms an antigen binding site that specifically binds the third epitope, $V_H$H1 specifically binds the second epitope, and $V_H$H2 specifically binds the fourth epitope. In alternative formats, each sdAb may be omitted, or replaced with two identical or different sdAbs fused to each other.

Figure 9:
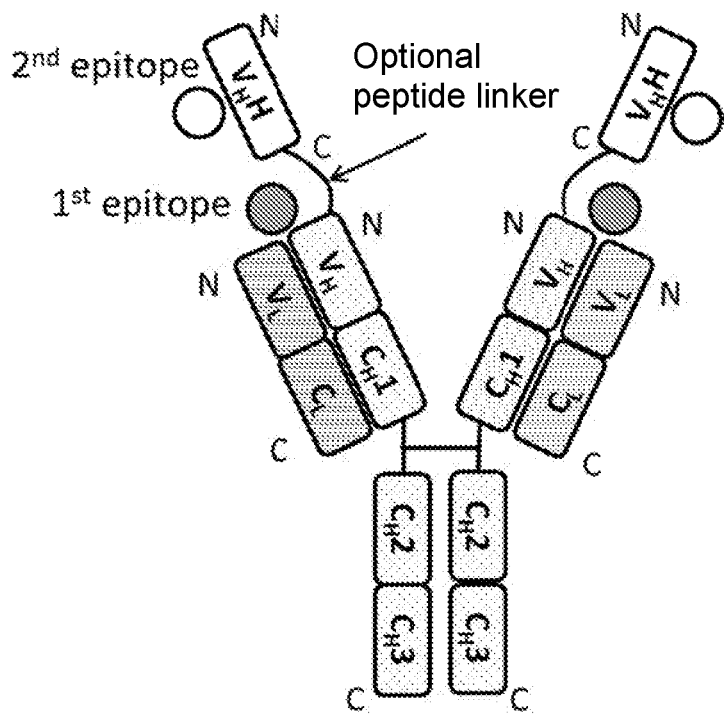

FIG. 9 depicts a schematic structure of an exemplary BABP comprising a monospecific full-length antibody having two identical heavy chains and two identical light chains, and two identical sdAbs, wherein the C-terminus of each sdAb is fused to the N-terminus of one heavy chain. The full-length antibody has two antigen binding sites that specifically bind a first epitope. The two sdAbs specifically bind the second epitope. For example, the BABP can consist of four polypeptide chains with structures from the N-terminus to the C-terminus as follows: (1) $V_L$-$C_L$; (2) $V_H$H-$V_H$-$C_H1$-$C_H2$-$C_H3$; (3) $V_H$H-$V_H$-$C_H1$-$C_H2$-$C_H3$; and (4) $V_L$-$C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, and each $V_H$H specifically binds a copy of the second epitope. In alternative formats, each sdAb may be omitted, or replaced with two identical or different sdAbs fused to each other. The monospecific full-length antibody may be replaced with a bispecific full-length antibody to further expand binding specificity.

Figure 10:
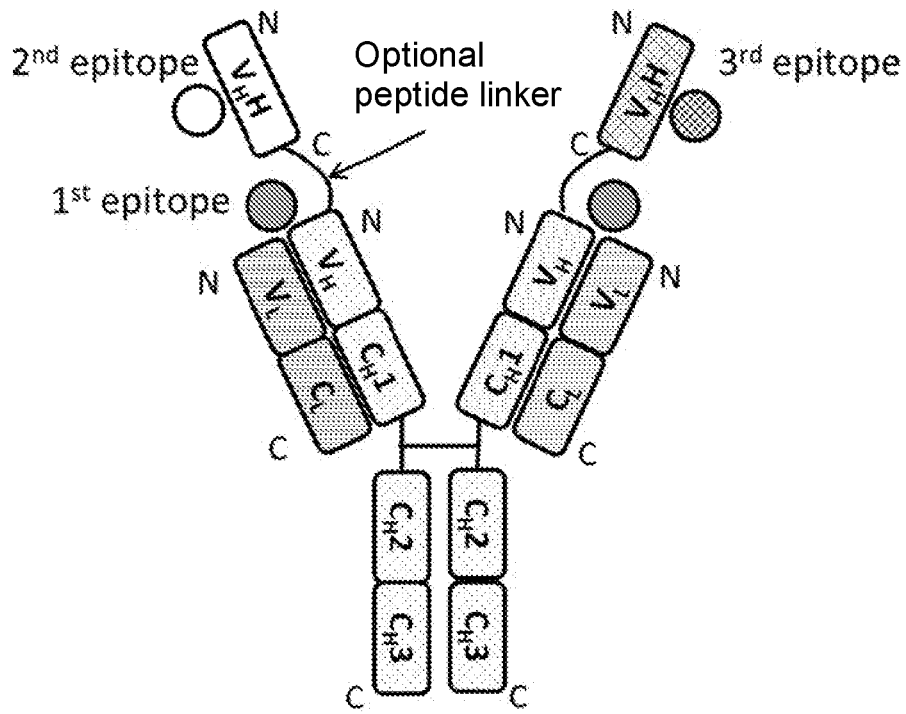

FIG. 10 depicts a schematic structure of an exemplary TABP comprising a monospecific full-length antibody having two identical heavy chains and two identical light chains, a first sdAb, and a second sdAb, wherein the C-terminus of each sdAb is fused to the N-terminus of one heavy chain. The full-length antibody has two antigen binding sites that specifically bind the first epitope. The first sdAb specifically binds the second epitope. The second sdAb specifically binds the third epitope. For example, the TABP can consist of four polypeptide chains with structures from the N-terminus to the C-terminus as follows: (1) $V_L$-$C_L$; (2) $V_H$H1-$V_H$-$C_H1$-$C_H2$-$C_H3$; (3) $V_H$H2-$V_H$-$C_H1$-$C_H2$-$C_H3$; and (4) $V_L$-$C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, $V_H$H1 specifically binds the second epitope, and $V_H$H2 specifically binds the third epitope. In alternative formats, each sdAb may be omitted, or replaced with two identical or different sdAbs fused to each other. The monospecific full-length antibody may be replaced with a bispecific full-length antibody to further expand binding specificity.

Figure 11:
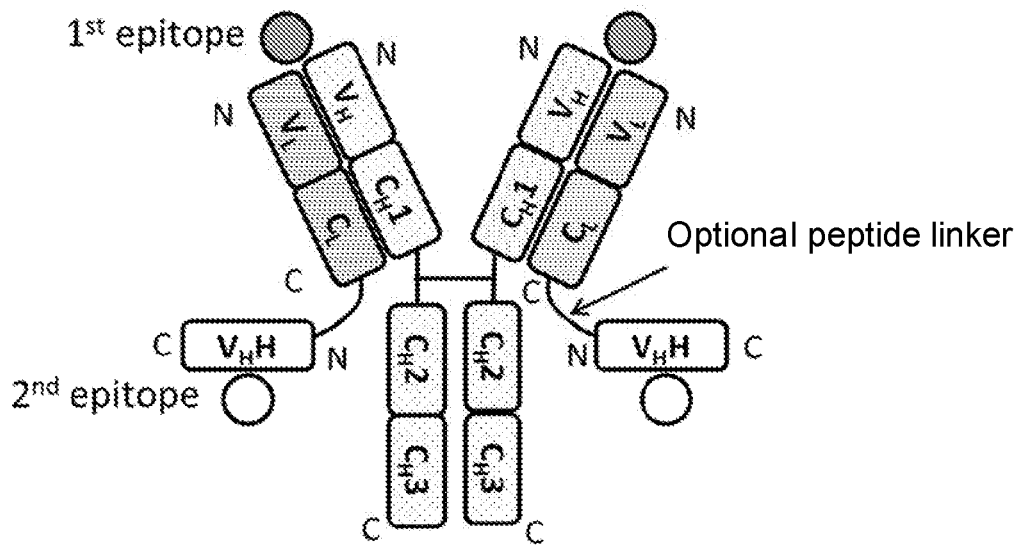

FIG. 11 depicts a schematic structure of an exemplary BABP comprising a monospecific full-length antibody having two identical heavy chains and two identical light chains, and two identical sdAbs, wherein the N-terminus of each sdAb is fused to the C-terminus of one light chain via an optional peptide linker. The full-length antibody has two antigen binding sites that specifically bind a first epitope. The two sdAbs specifically bind the second epitope. For example, the BABP can consist of four polypeptide chains with structures from the N-terminus to the C-terminus as follows: (1) $V_L$-$C_L$-$V_H$H; (2) $V_H$-$C_H1$-$C_H2$-$C_H3$; (3) $V_H$-$C_H1$-$C_H2$-$C_H3$; and (4) $V_L$-$C_L$-$V_H$H, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, and each $V_H$H specifically binds a copy of the second epitope. In alternative formats, each sdAb may be omitted, or replaced with two identical or different sdAbs fused to each other. The monospecific full-length antibody may be replaced with a bispecific full-length antibody to further expand binding specificity.

Figure 12:
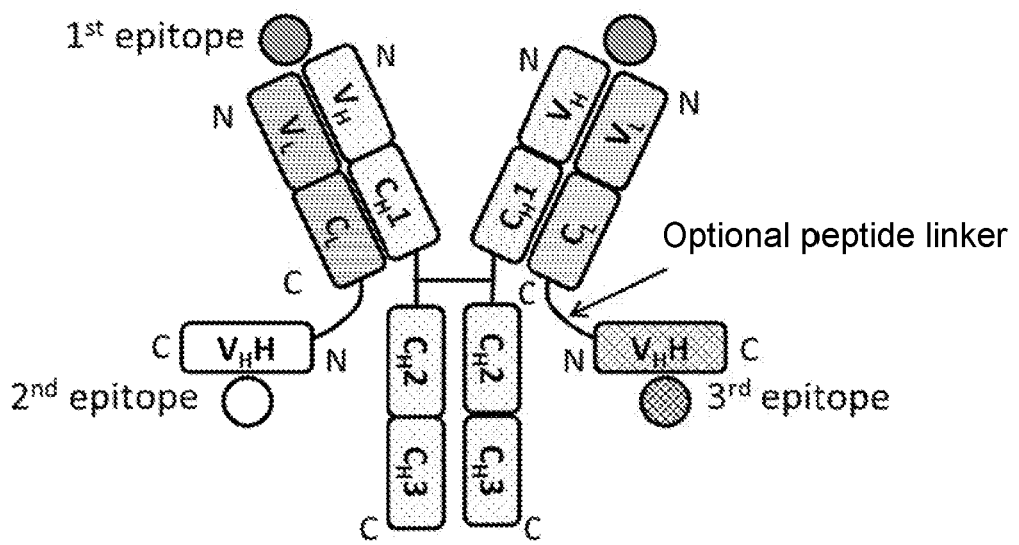

FIG. 12 depicts a schematic structure of an exemplary TABP comprising a monospecific full-length antibody having two identical heavy chains and two identical light chains, a first sdAb, and a second sdAb, wherein the N-terminus of each sdAb is fused to the C-terminus of one light chain via an optional peptide linker. The full-length antibody has two antigen binding sites that specifically bind a first epitope. The first sdAb specifically binds the second epitope. The second sdAb specifically binds the third epitope. For example, the TABP can consist of four polypeptide chains with structures from the N-terminus to the C-terminus as follows: (1) $V_L$-$C_L$-$V_H$H1; (2) $V_H$-$C_H1$-$C_H2$-$C_H3$; (3) $V_H$-$C_H1$-$C_H2$-$C_H3$; and (4) $V_L$-$C_L$-$V_H$H2, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, $V_H$H1 specifically binds the second epitope, and $V_H$H2 specifically binds the third epitope. In alternative formats, each sdAb may be omitted, or replaced with two identical or different sdAbs fused to each other. The monospecific full-length antibody may be replaced with a bispecific full-length antibody to further expand binding specificity.

Figure 13:
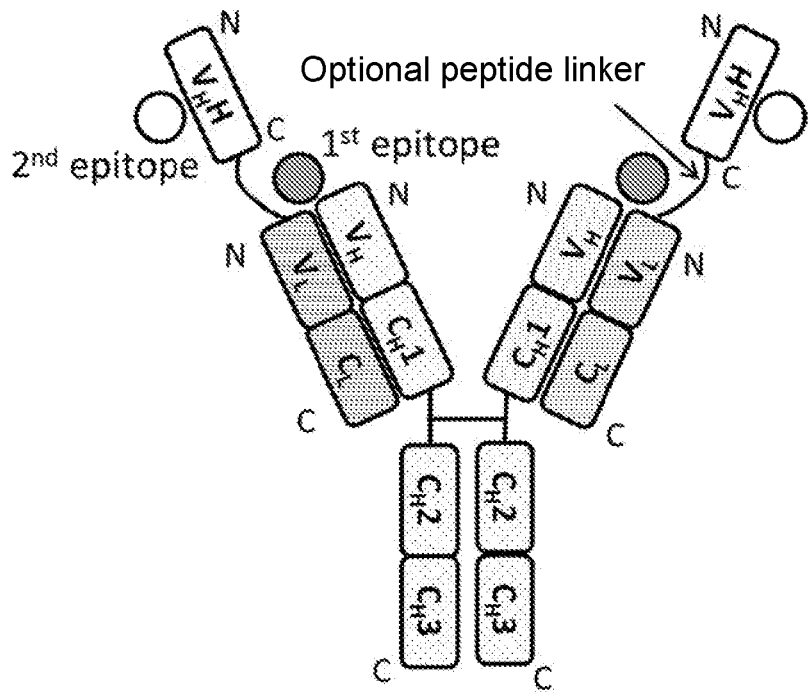

FIG. 13 depicts a schematic structure of an exemplary BABP comprising a monospecific full-length antibody having two identical heavy chains and two identical light chains, and two identical sdAbs, wherein the C-terminus of each sdAb is fused to the N-terminus of one light chain via an optional peptide linker. The full-length antibody has two antigen binding sites that specifically bind a first epitope. The two sdAbs specifically bind the second epitope. For example, the BABP can consist of four polypeptide chains with structures from the N-terminus to the C-terminus as follows: (1) $V_HH\text{-}V_L\text{-}C_L$; (2) $V_H\text{-}C_H1\text{-}C_H2\text{-}C_H3$; (3) $V_H\text{-}C_H1\text{-}C_H2\text{-}C_H3$; and (4) $V_HH\text{-}V_L\text{-}C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, and each $V_HH$ specifically binds a copy of the second epitope. In alternative formats, each sdAb may be omitted, or replaced with two identical or different sdAbs fused to each other. The monospecific full-length antibody may be replaced with a bispecific full-length antibody to further expand binding specificity.

Figure 14:
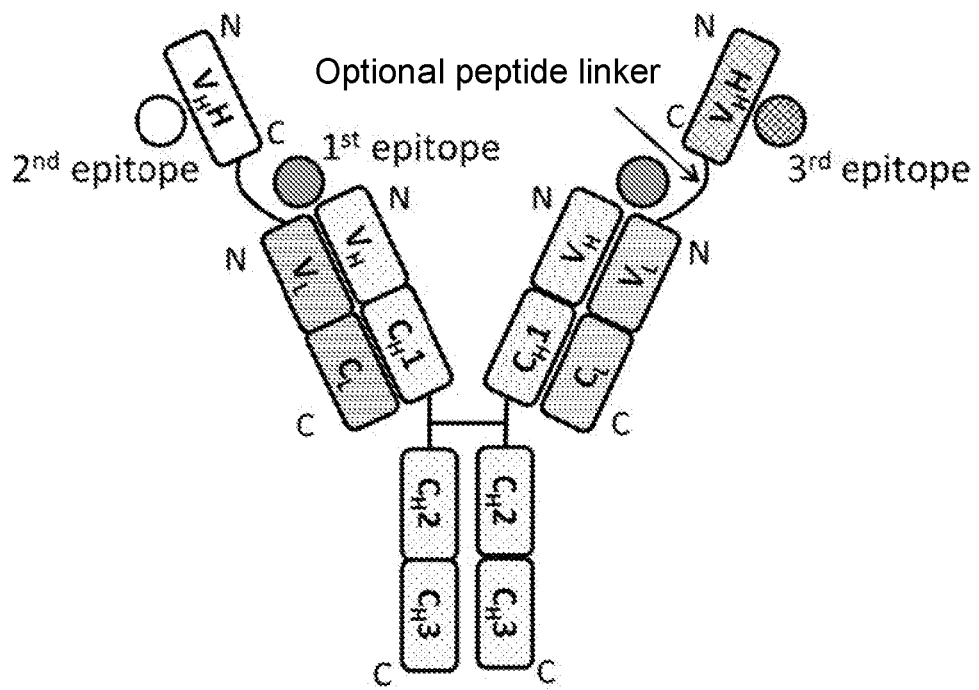

FIG. 14 depicts a schematic structure of an exemplary TABP comprising a monospecific full-length antibody having two identical heavy chains and two identical light chains, a first sdAb, and a second sdAb, wherein the C-terminus of each sdAb is fused to the N-terminus of one light chain via an optional peptide linker. The full-length antibody has two antigen binding sites that specifically bind a first epitope. The first sdAb specifically binds the second epitope. The second sdAb specifically binds the third epitope. For example, the TABP can consist of four polypeptide chains with structures from the N-terminus to the C-terminus as follows: (1) $V_HH1\text{-}V_L\text{-}C_L$; (2) $V_H\text{-}C_H1\text{-}C_H2\text{-}C_H3$; (3) $V_H\text{-}C_H1\text{-}C_H2\text{-}C_H3$; and (4) $V_HH2\text{-}V_L\text{-}C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, $V_HH1$ specifically binds the second epitope, and $V_HH2$ specifically binds the third epitope. In alternative formats, each sdAb may be omitted, or replaced with two identical or different sdAbs fused to each other. The monospecific full-length antibody may be replaced with a bispecific full-length antibody to further expand binding specificity.

Figure 15:
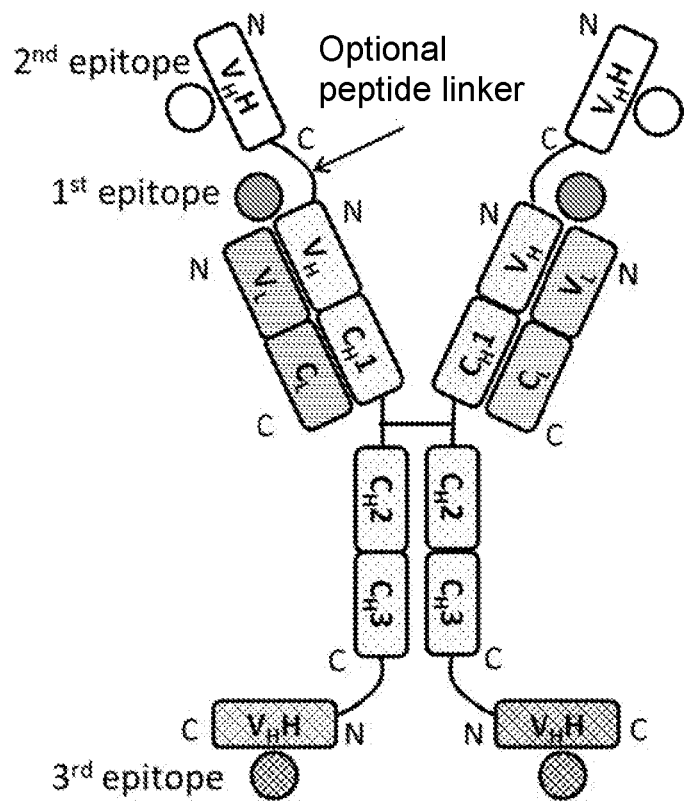

FIG. 15 depicts a schematic structure of an exemplary TABP comprising a monospecific full-length antibody having two identical heavy chains and two identical light chains, two identical first sdAbs, and two identical second sdAbs, wherein the C-terminus of each first sdAb is fused to the N-terminus of one heavy chain via an optional peptide linker, and the N-terminus of each second sdAb is fused to the C-terminus of one heavy chain via an optional peptide linker. The full-length antibody has two antigen binding sites that specifically bind a first epitope. The first sdAb specifically binds the second epitope. The second sdAb specifically binds the third epitope. For example, the TABP can consist of four polypeptide chains with structures from the N-terminus to the C-terminus as follows: (1) $V_L\text{-}C_L$; (2) $V_HH1\text{-}V_H\text{-}C_H1\text{-}C_H2\text{-}C_H3\text{-}V_HH2$; (3) $V_HH1\text{-}V_H\text{-}C_H1\text{-}C_H2\text{-}C_H3\text{-}V_HH2$; and (4) $V_L\text{-}C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, each $V_HH1$ specifically binds a copy of the second epitope, and each $V_HH2$ specifically binds a copy of the third epitope. In alternative formats, each sdAb may be omitted, or replaced with two identical or different sdAbs fused to each other. The monospecific full-length antibody may be replaced with a bispecific full-length antibody to further expand binding specificity.

Figure 16:
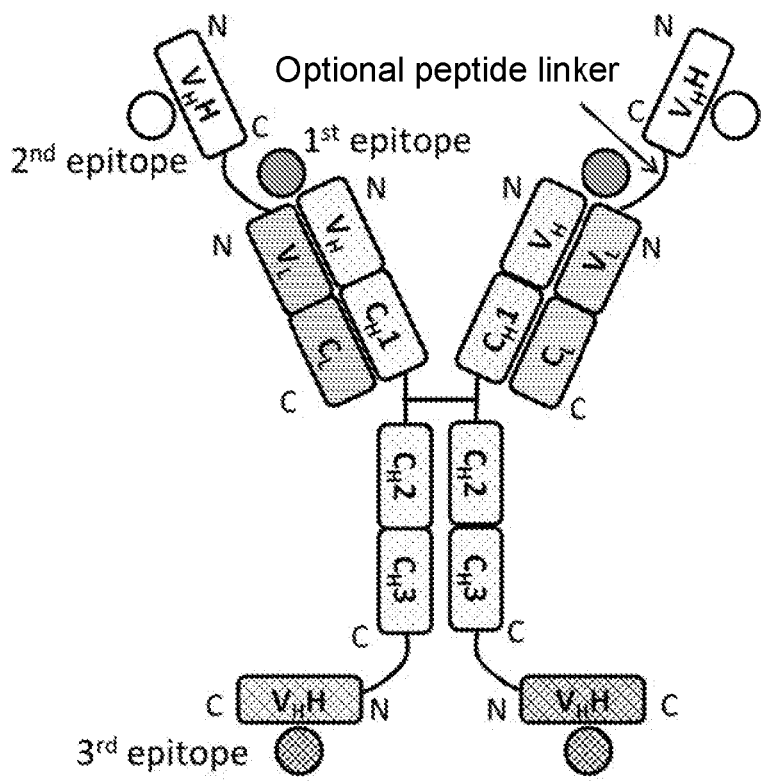

FIG. 16 depicts a schematic structure of an exemplary TABP comprising a monospecific full-length antibody having two identical heavy chains and two identical light chains, two identical first sdAbs, and two identical second sdAbs, wherein the C-terminus of each first sdAb is fused to the N-terminus of one light chain via an optional peptide linker, and the N-terminus of each second sdAb is fused to the C-terminus of one heavy chain via an optional peptide linker. The full-length antibody has two antigen binding sites that each specifically binds a first epitope. The first sdAb specifically binds a second epitope. The second sdAb specifically binds a third epitope. For example, the TABP can consist of four polypeptide chains with structures from the N-terminus to the C-terminus as follows: (1) $V_HH1\text{-}V_L\text{-}C_L$; (2) $V_H\text{-}C_H1\text{-}C_H2\text{-}C_H3\text{-}V_HH2$; (3) $V_H\text{-}C_H1\text{-}C_H2\text{-}C_H3\text{-}V_HH2$; and (4) $V_HH1\text{-}V_L\text{-}C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, each $V_HH1$ specifically binds a copy of the second epitope, and each $V_HH2$ specifically binds a copy of the third epitope. In alternative formats, each sdAb may be omitted, or replaced with two identical or different sdAbs fused to each other. The monospecific full-length antibody may be replaced with a bispecific full-length antibody to further expand binding specificity.

Figure 17:
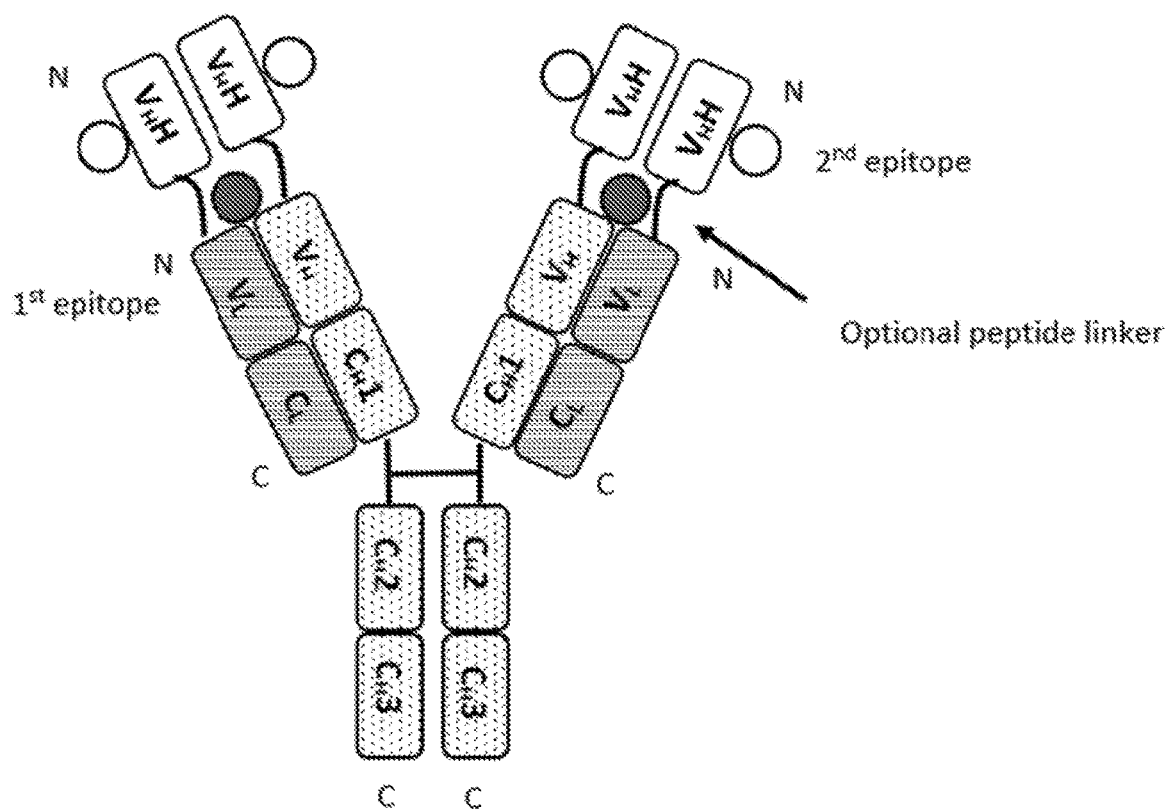

FIG. 17 depicts a schematic structure of an exemplary BABP comprising a monospecific full-length antibody having two identical heavy chains and two identical light chains, and four identical sdAbs, wherein the C-terminus of each sdAb is fused to the N-terminus of heavy chain or light chain of the monospecific full-length antibody via an optional peptide linker. The full-length antibody has two antigen binding sites that each specifically binds a first epitope. Each sdAb specifically binds to a second epitope. For example, the BABP can consist of four polypeptide chains with structures from the N-terminus to the C-terminus as follows: (1) $V_HH\text{-}V_L\text{-}C_L$; (2) $V_HH\text{-}V_H\text{-}C_H1\text{-}C_H2\text{-}C_H3$; (3) $V_HH\text{-}V_H\text{-}C_H1\text{-}C_H2\text{-}C_H3$; and (4) $V_HH\text{-}V_L\text{-}C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, and each $V_HH$ specifically binds a copy of the second epitope. In alternative formats, each sdAb may be omitted, or replaced with two identical or different sdAbs fused to each other. The monospecific full-length antibody may be replaced with a bispecific full-length antibody to further expand binding specificity.

Figure 18:
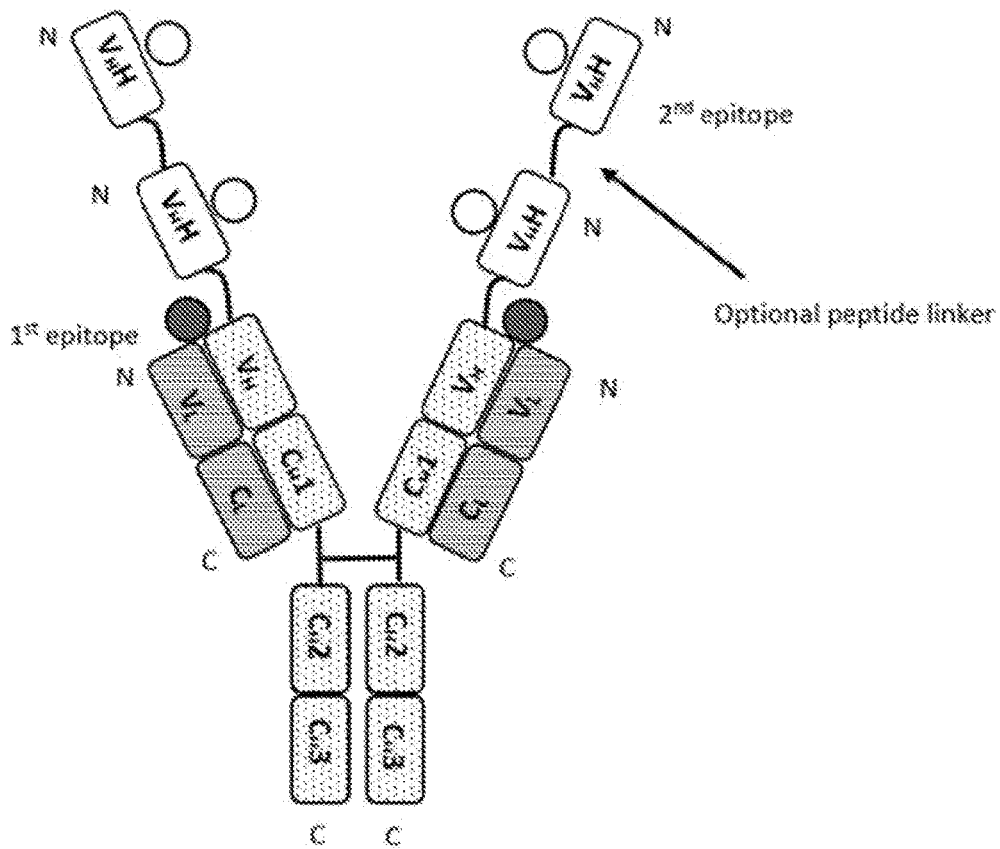

FIG. 18 depicts a schematic structure of an exemplary BABP comprising a monospecific full-length antibody having two identical heavy chains and two identical light chains, and four identical sdAbs, wherein fused to the N-terminus of each heavy chain are two identical sdAbs, and the two sdAbs are fused to each other via an optional peptide linker. The full-length antibody has two antigen binding sites that each specifically binds a first epitope.

Each sdAb specifically binds a second epitope. For example, the BABP can consist of four polypeptide chains with structures from the N-terminus to the C-terminus as follows: (1) $V_L\text{-}C_L$; (2) $V_HH\text{-}V_HH\text{-}V_H\text{-}C_H1\text{-}C_H2\text{-}C_H3$; (3) $V_HH\text{-}V_HH\text{-}V_H\text{-}C_H1\text{-}C_H2\text{-}C_H3$; and (4) $V_L\text{-}C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, and each $V_HH$ specifically binds a copy of the second epitope. In alternative formats, each sdAb may be omitted, or replaced with two identical or different sdAbs fused to each other. The monospecific full-length antibody may be replaced with a bispecific full-length antibody to further expand binding specificity.

Figure 19:
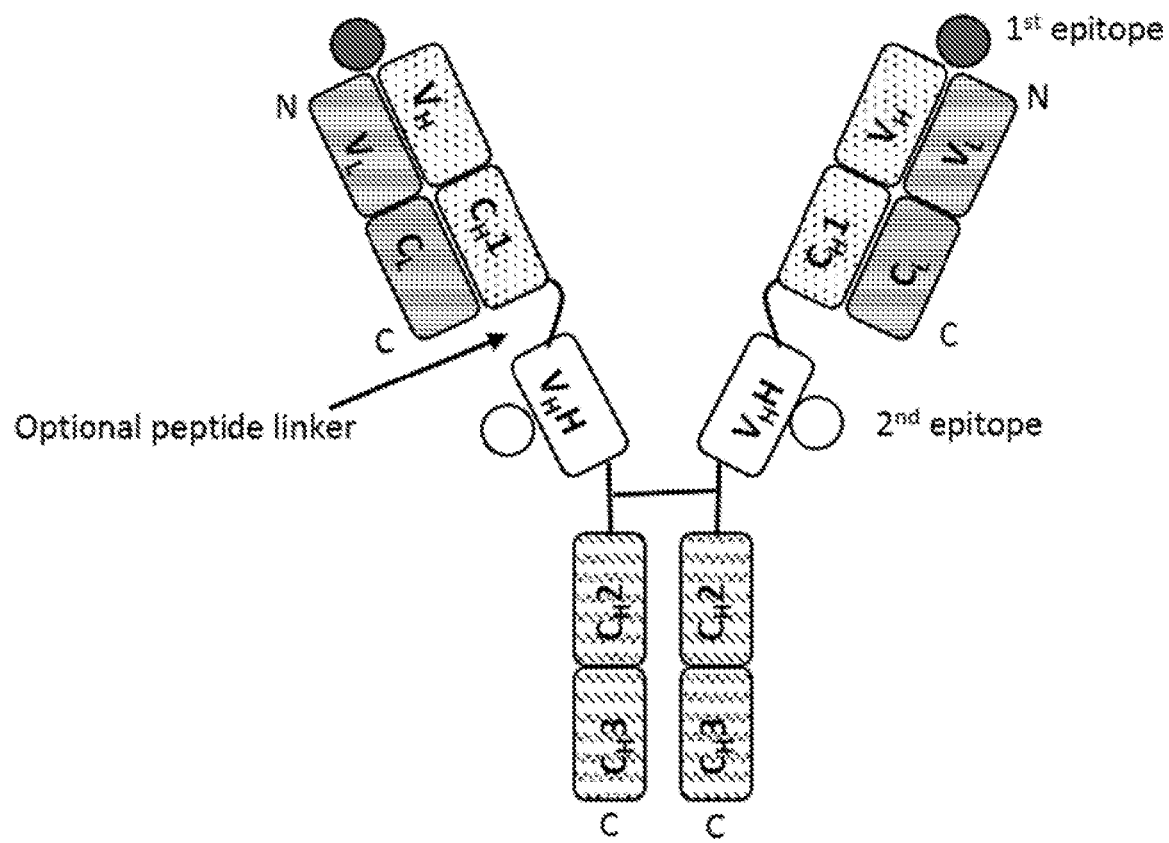

FIG. 19 depicts a schematic structure of an exemplary BABP comprising a monospecific full-length antibody having two identical heavy chains and two identical light chains, and two identical sdAbs, wherein the N-terminus of each sdAb is fused to the C-terminus of the $C_H1$ region via an optional peptide linker and C-terminus of each sdAb is fused to the N-terminus of the $C_H2$ region of the monospecific full-length antibody. The full-length antibody has two antigen binding sites that each specifically binds a first epitope. Each sdAb specifically binds a second epitope. For example, the BABP can consist of four polypeptide chains with structures from the N-terminus to the C-terminus as follows: (1) $V_L$-$C_L$; (2) $V_H$-$C_H1$-$V_HH$-$C_H2$-$C_H3$; (3) $V_H$-$C_H1$-$V_HH$-$C_H2$-$C_H3$; and (4) $V_L$-$C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, and each $V_HH$ specifically binds a copy of the second epitope. In alternative formats, each sdAb may be omitted, or replaced with two identical or different sdAbs fused to each other. The monospecific full-length antibody may be replaced with a bispecific full-length antibody to further expand binding specificity. In alternative formats, to expand specificity, the two Fab fragments can specifically bind different epitopes, and/or the $V_HH$ fragments can specifically bind different epitopes.

Figure 20:
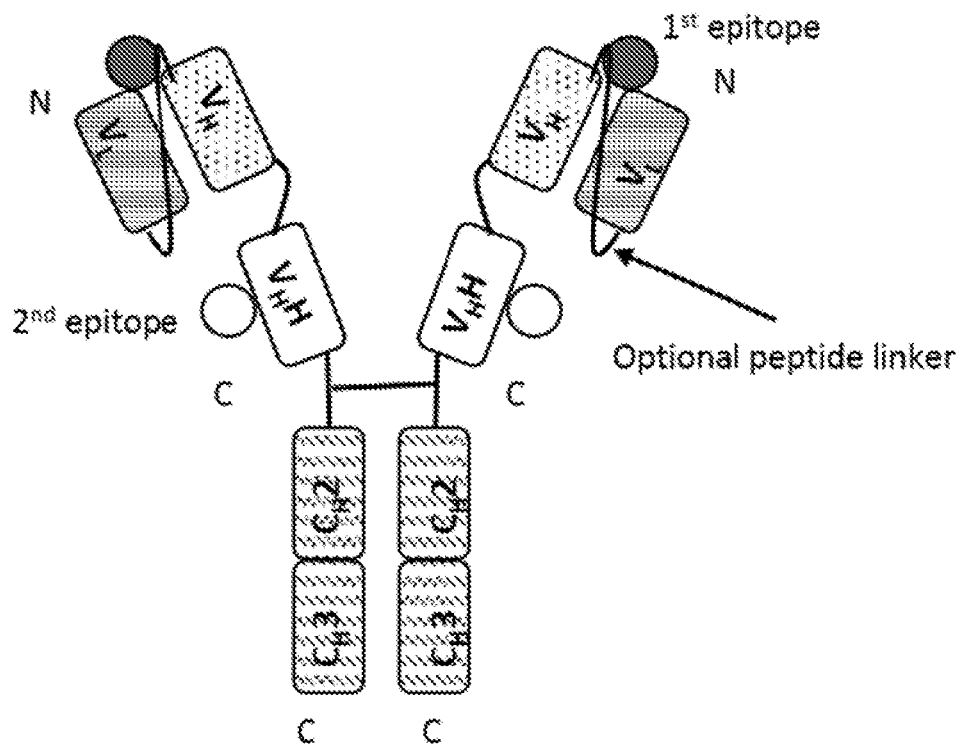

FIG. 20 depicts a schematic structure of an exemplary BABP comprising two identical single chain variable fragments (scFvs), two identical sdAbs and a fragment crystallizable (Fc) region, wherein the N-terminus of each sdAb is fused to the C-terminus of an scFv via an optional peptide linker and the C-terminus of each sdAb is fused to the N-terminus of the Fc region. Each scFv specifically binds a first epitope. Each sdAb specifically binds a second epitope. For example, the BABP can consist of two polypeptide chains each with a structure from the N-terminus to the C-terminus as follows: $V_L$—$V_H$-$V_HH$-$C_H2$-$C_H3$, wherein $V_H$ and $V_L$ of each polypeptide chain forms a scFv domain that specifically binds a copy of the first epitope, and each $V_HH$ specifically binds a copy of the second epitope. In alternative formats, the scFv domain can comprise from the N-terminus to the C-termins: $V_H$—$V_L$. Additionally, to expand specificity, the two scFvs can specifically bind different epitopes, and/or the $V_HH$ fragments can specifically bind different epitopes.

Figure 21:
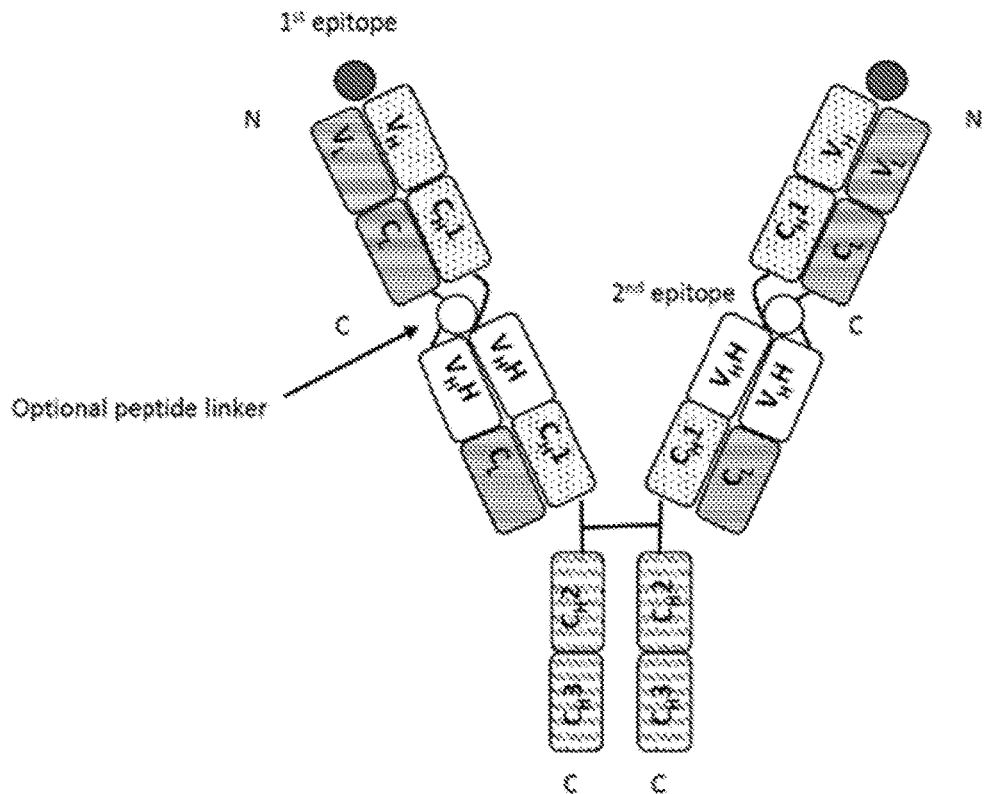

FIG. 21 depicts a schematic structure of an exemplary BABP comprising two identical antigen-binding (Fab) fragments, two identical Fab-like fragments each comprising two $V_HH$ fragments, and an Fc region. In each Fab-like domain, the $V_H$ and $V_L$ regions are each replaced by an sdAb. Each Fab fragment specifically binds a first epitope, and each Fab-like fragment specifically binds a second epitope. For example, the BABP can consist of four polypeptide chains with structures from the N-terminus to the C-terminus as follows: (1) $V_L$-$C_L$-$V_HH$-$C_L$; (2) $V_H$-$C_H1$-$V_HH$-$C_H1$-$C_H2$-$C_H3$; (3) $V_H$-$C_H1$-$V_HH$-$C_H1$-$C_H2$-$C_H3$; and (4) $V_L$-$C_L$-$V_HH$-$C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, and each $V_HH$ specifically binds a copy of the second epitope. In alternative formats, to expand specificity, the two Fab fragments can specifically bind different epitopes, and/or the Fab-like fragments can specifically bind different epitopes.

Figure 22:
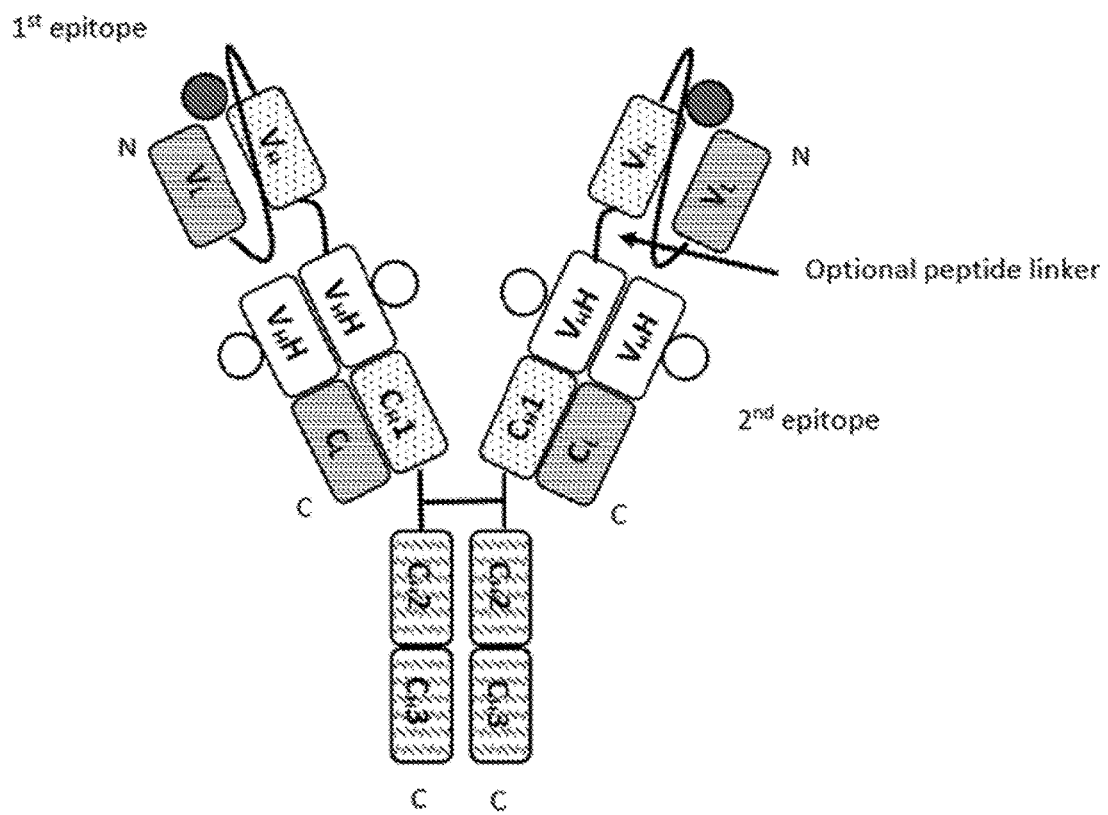

FIG. 22 depicts a schematic structure of an exemplary BABP comprising two identical scFvs, two identical Fab-like fragments each comprising two $V_HH$ fragments, and an Fc region. In each Fab-like domain, the $V_H$ and $V_L$ regions are each replaced by an sdAb. For example, the BABP can consist of four polypeptide chains with structures from the N-terminus to the C-terminus as follows: (1) $V_HH$-$C_L$; (2) $V_L$-$V_H$-$V_HH$-$C_H1$-$C_H2$-$C_H3$; (3) $V_L$-$V_H$-$V_HH$-$C_H1$-$C_H2$-$C_H3$; and (4) $V_HH$-$C_L$, wherein $V_H$ and $V_L$ of polypeptide chains (2) and (3) each forms an scFv that specifically binds a copy of the first epitope, and each $V_HH$ specifically binds a copy of the second epitope. In alternative formats, the C-terminus of the scFv may be fused to the N-terminus of the chain in the Fab-like fragment comprising $V_HH$-$C_L$; and/or the scFv domain can comprise from the N-terminus to the C-termins: $V_H$—$V_L$. Additionally, to expand specificity, the two scFvs can specifically bind different epitopes, and/or the $V_HH$ fragments can specifically bind different epitopes.

Figure 23:
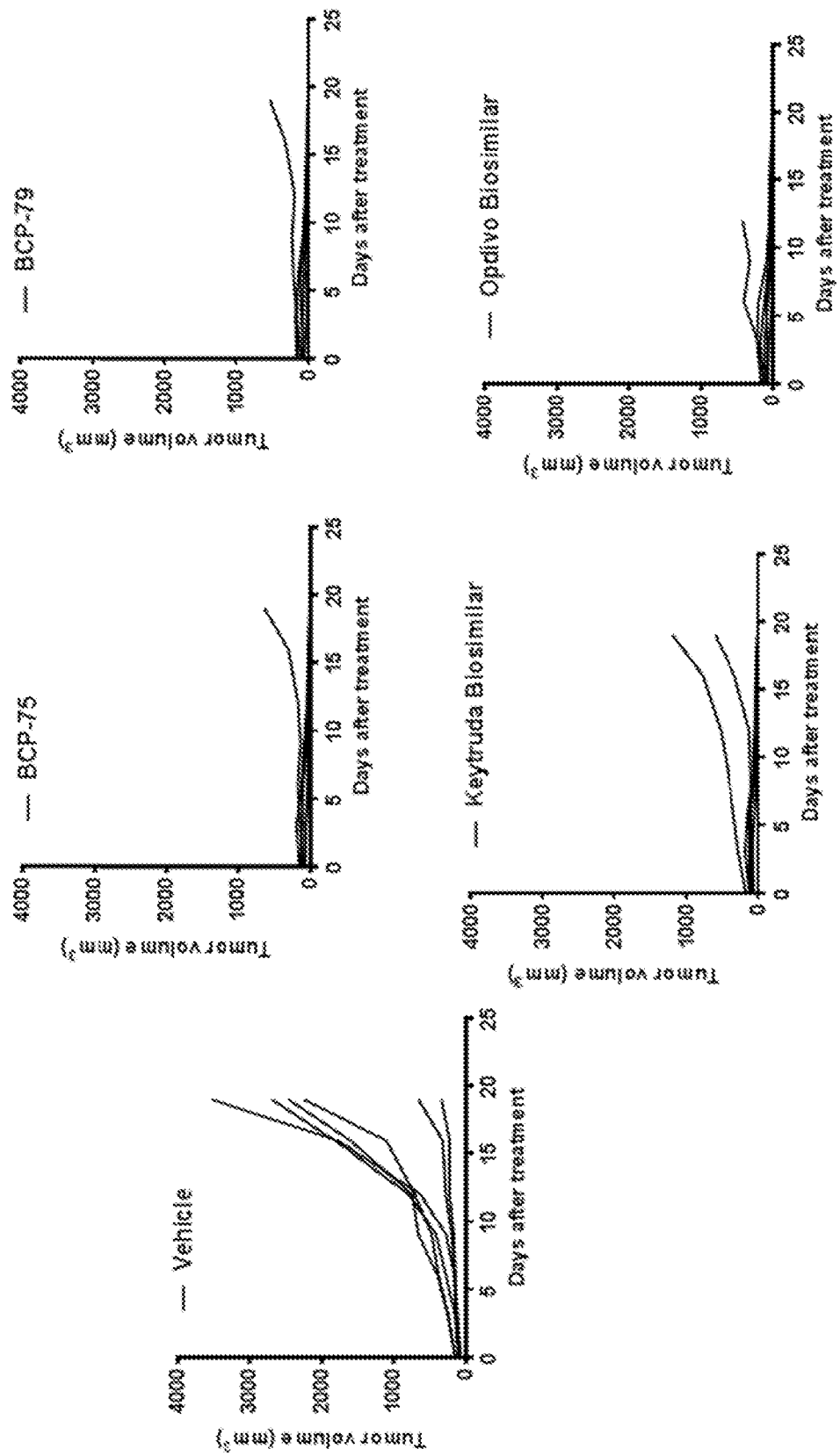

FIG. 23 shows the results from an in vivo efficacy experiment of BABPs BCP-75 and BCP-79 in MC38 syngeneic model in C56BL/6 PD-1 KI mice. The results of the BABPs are compared to those of the two backbone 4-chain antibodies, in-house expressed biosimilar antibodies pembrolizumab and nivolumab.

Figure 24:
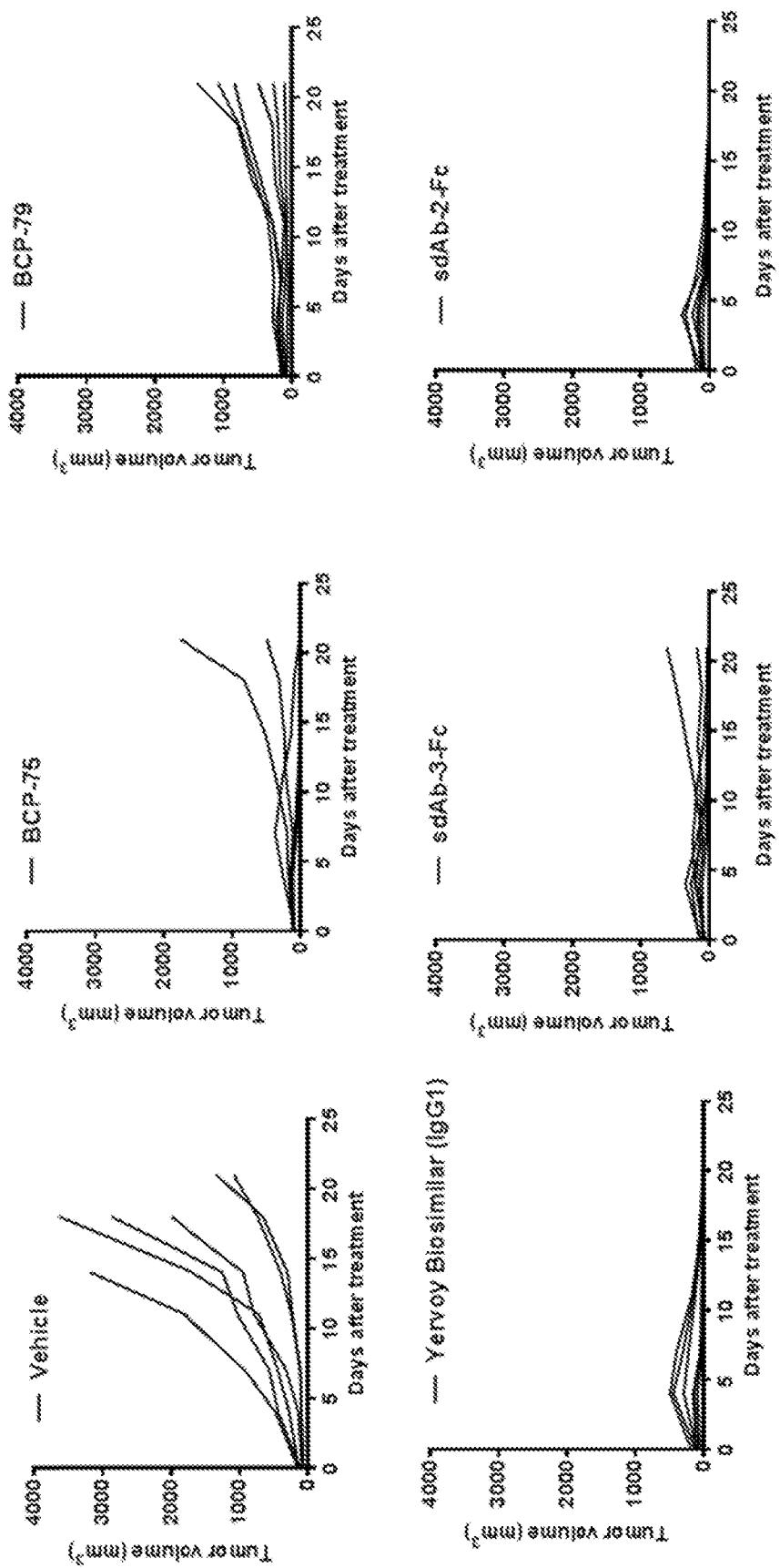

FIG. 24 shows the results from an in vivo efficacy experiment of BABPs BCP-75 and BCP-79 in MC38 syngeneic model in C56BL/6 CTLA-4 KI mice. The results of the BABPs are compared to those of Fc fusion proteins comprising sdAb-2 or sdAb-3, wherein the Fc fragment is the same as the in-house expressed biosimilar antibodies pembrolizumab and nivolumab. In-house expressed ipilimumab of the IgG1 isotype serves as the positive control for this experiment.

Figure 25:
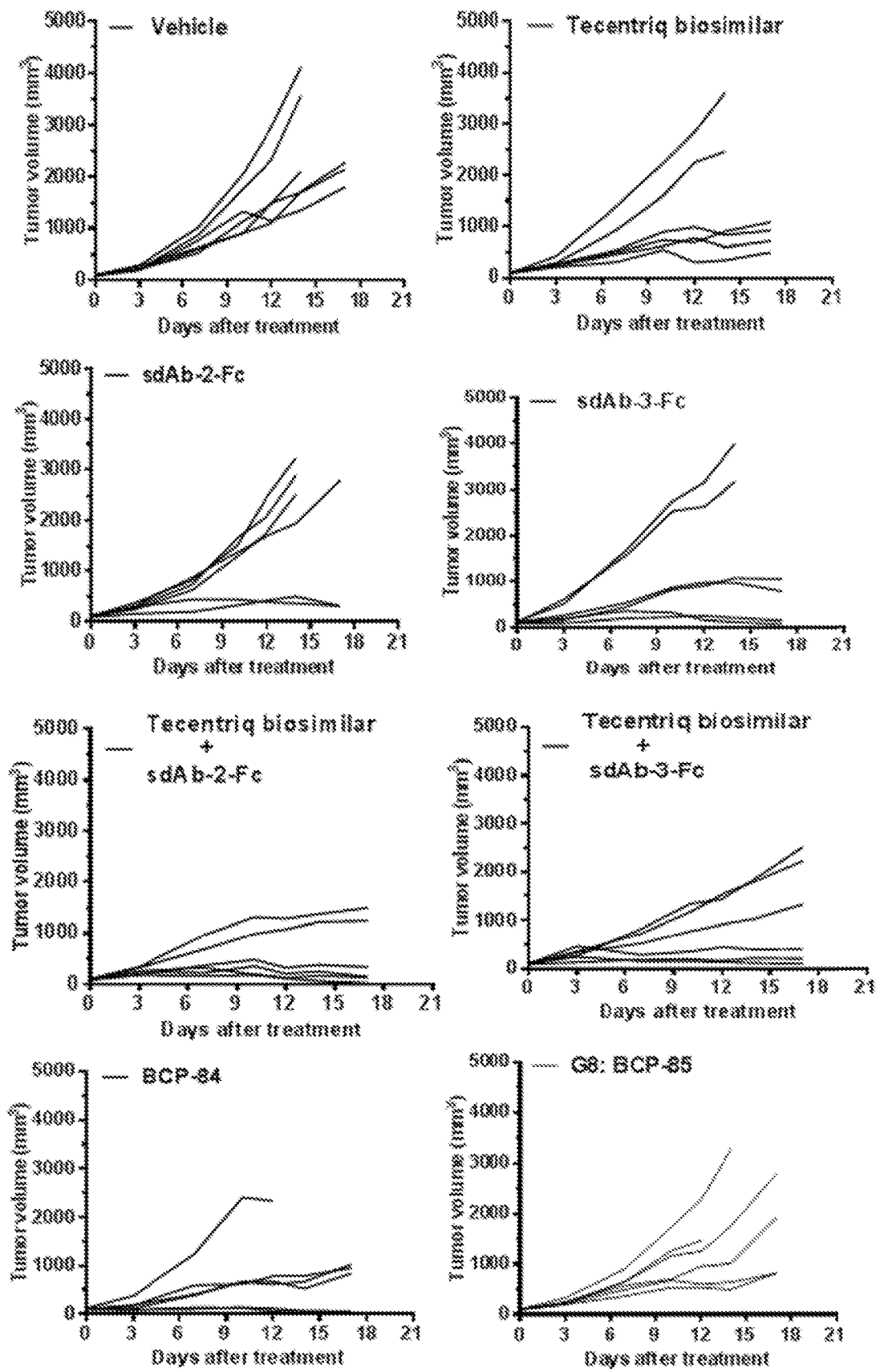

FIG. 25 shows the results from an in vivo efficacy experiment of BABPs BCP-84 and BCP-85 compared to combination therapy in human PD-L1 KI MC38 syngeneic model in C56BL/6 CTLA-4 KI mice.

Figure 26A:
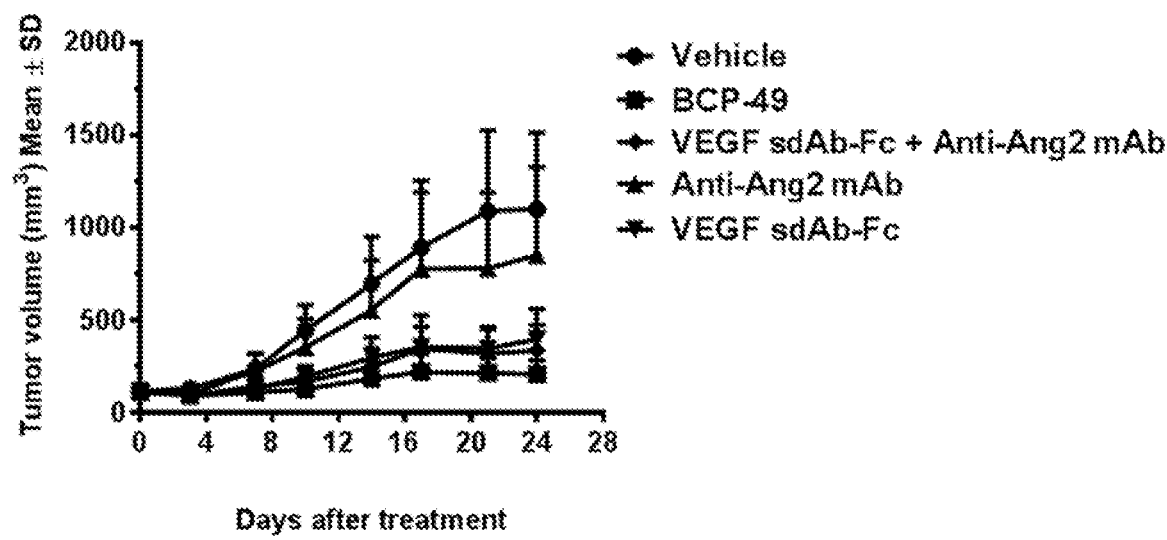
Figure 26B:
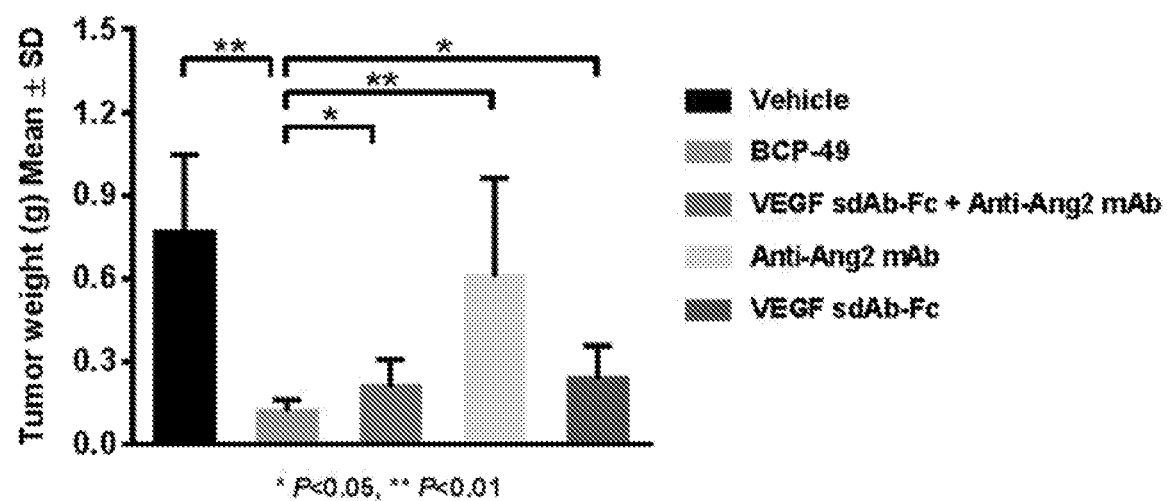

FIG. 26A and FIG. 26B show the results from an in vivo efficacy experiment of BABP BCP-49 compared to combination therapy in A431 xenograft model in BALB/c nude mice.

DETAILED DESCRIPTION OF THE INVENTION

The present application provides a MABP comprising a single-domain antibody (sdAb) fused to a full-length antibody or antigen binding fragment that comprise a heavy chain variable domain ($V_H$) and a light chain variable domain ($V_L$). The sdAb specifically binds a target (such as an epitope or antigen) that is distinct from the target(s) recognized by the full-length antibody or antigen binding fragment, thereby conferring a broadened targeting capability. As a building block in a MABP, sdAb has several advantages over other antigen binding fragments such as Fab and scFv used in currently known multispecific antibody formats, including, but not limited to, small size, high solubility and stability, weak immunogenicity in human, and ability to target a variety of epitopes. Thus, the MABPs described herein can have similar molecular weight and pharmacokinetic properties compared to those of the full-length antibody or antigen binding fragment component. For example, a MABP can be designed by fusing one or more sdAbs to a monoclonal antibody with proven clinical efficacy and safety to provide increased clinical benefits and desirable pharmacokinetic properties without impeding the expressibility of the multispecific construct. In some embodiments, the MABP comprises two naturally produced components or derivatives thereof, e.g., a naturally produced or humanized Camelid $V_HH$ fragment, and a naturally produced monoclonal antibody, fused to each other by polypeptide linkers. Unlike the majority of known bispecific antibody formats, the MABP of the present application has excellent productivity, stability and solubility. In vitro efficacy data further indicates that the MABP retains anti-tumor activity of the parental antibodies. Synergistic activity are also found or expected in in vivo tumor animal models. The MABP format of the present application can be adopted to target a variety of disease-related epitope or antigen combinations, such as a combination of immune checkpoint molecules, a combination of cell surface antigens (such as tumor antigens), or a combination of pro-inflammatory molecules, thereby providing agents that are useful for treating a variety of diseases and conditions, such as cancer, inflammation, and autoimmune diseases.

Accordingly, one aspect of the present application provides a MABP comprising: (a) a first antigen binding portion comprising a heavy chain variable domain ($V_H$) and a light chain variable domain ($V_L$), wherein the $V_H$ and $V_L$ together form an antigen-binding site that specifically binds a first epitope, and (b) a second antigen binding portion comprising an sdAb that specifically binds a second epitope, wherein the first antigen binding portion and the second antigen binding portion are fused to each other.

One aspect of the present application provides a MABP comprising: (a) a first antigen binding portion comprising a heavy chain variable domain ($V_H$) and a light chain variable domain ($V_L$), wherein the $V_H$ and $V_L$ together form an antigen-binding site that specifically binds a first immune checkpoint molecule, and (b) a second antigen binding portion comprising an sdAb that specifically binds a second immune checkpoint molecule, wherein the first antigen binding portion and the second antigen binding portion are fused to each other.

One aspect of the present application provides a MABP comprising: (a) a first antigen binding portion comprising a heavy chain variable domain ($V_H$) and a light chain variable domain ($V_L$), wherein the $V_H$ and $V_L$ together form an antigen-binding site that specifically binds a first pro-inflammatory molecule, and (b) a second antigen binding portion comprising an sdAb that specifically binds a second pro-inflammatory molecule, wherein the first antigen binding portion and the second antigen binding portion are fused to each other.

One aspect of the present application provides a MABP comprising: (a) a first antigen binding portion comprising a heavy chain variable domain ($V_H$) and a light chain variable domain ($V_L$), wherein the $V_H$ and $V_L$ together form an antigen-binding site that specifically binds a first tumor antigen, and (b) a second antigen binding portion comprising an sdAb that specifically binds a cell surface antigen (such as tumor antigen, or a cell surface antigen on an immune effector cell), wherein the first antigen binding portion and the second antigen binding portion are fused to each other.

Also provided are pharmaceutical compositions, kits and articles manufacture comprising the MABPs, and methods of treating a disease using the MABPs described herein.

I. Definitions

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Current Protocols in Molecular Biology or Current Protocols in Immunology, John Wiley & Sons, New York, N.Y. (2009); Ausubel et al, Short Protocols in Molecular Biology, $3^{rd}$ ed., Wiley & Sons, 1995; Sambrook and Russell, Molecular Cloning: A Laboratory Manual (3rd Edition, 2001); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984) and other like references.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" by the MABP of the present application if one or more symptoms associated with the disease or condition being treated (such as cancer, inflammatory or autoimmune disease) are mitigated or eliminated.

As used herein, an "effective amount" refers to an amount of an agent or drug effective to treat a disease or condition in a subject. In the case of cancer, the effective amount of the MABP of the present application may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, an "individual" or a "subject" refers to a mammal, including, but not limited to, human, bovine, horse, feline, canine, rodent, or primate. In some embodiments, the individual is a human.

The term "antibody" includes monoclonal antibodies (including full length 4-chain antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')$_2$, and Fv). The term "immunoglobulin" (Ig) is used interchangeably with "antibody" herein. Antibodies contemplated herein include heavy-chain only antibodies and sdAbs.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the $C_H$ sequence and function, e.g., humans express the following subclasses: IgG1, IgG2A, IgG2B, IgG3, IgG4, IgA1 and IgA2.

An "isolated" antibody is one that has been identified, separated and/or recovered from a component of its production environment (E.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites. Heavy-chain only antibodies from the *Camelidae* species have a single heavy chain variable region, which is referred to as "$V_HH$". $V_HH$ is thus a special type of $V_H$.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present application may be made by a variety of techniques, including, for example, the hybridoma method (e.g., Kohler and Milstein., *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806;

5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically full-length 4-chain antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10): 1057-1062 [1995]); single-chain antibody molecules and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies described herein comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include PRIMATTZFD® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, for example, Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227: 381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, 4-chain antibodies comprise six HVRs; three in the $V_H$ (H1, H2, H3), and three in the $V_L$ (L1, L2, L3). Single-domain antibodies comprise three HVRs, such as three in the $V_H$H (H1, H2, H3). In native 4-chain antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996).

The term "Complementarity Determining Region" or "CDR" are used to refer to hypervariable regions as defined by the Kabat system. See Kabat et al., Sequences of Proteins of Immunological Interest, 5th Ed. Public Health Service, National Institutes of Health, Bethesda, Md. (1991)

A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below in Table I.

TABLE I

HVR delineations.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
|  |  | (Kabat Numbering) |  |  |
| H1 | H31-H35 | H26-H35 | H26-H32 | H30-H35 |
|  |  | (Chothia Numbering) |  |  |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the $V_L$ and 26-35 (H1), 50-65 or 49-65 (H2) and 93-102, 94-102, or 95-102 (H3) in the $V_H$. The variable domain residues are numbered according to Kabat et al., supra, for each of these definitions.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., Sequences of Proteins of Immunological Interest, 5$^{th}$ Ed. Public Health Service, National Institutes of Health, Bethesda, Md. (1991). Examples include for the $V_L$, the subgroup may be subgroup kappa I, kappa II, kappa III or kappa IV as in Kabat et al., supra. Additionally, for the $V_H$, the subgroup may be subgroup I, subgroup II, or subgroup III as in Kabat et al. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

An "amino-acid modification" at a specified position, e.g. of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by $V_H$- and $V_L$-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically binds" or is "specific for" refers to measurable and reproducible interactions such as binding between a target and an antibody, which is determinative of the presence of the target in the presence of a heterogeneous population of molecules including biological molecules. For example, an antibody that specifically binds a target (which can be an epitope) is an antibody that binds this target with greater affinity, avidity, more readily, and/or with greater duration than it binds other targets. In one embodiment, the extent of binding of an antibody to an unrelated target is less than about 10% of the binding of the antibody to the target as measured, e.g., by a radioimmunoassay (RIA). In certain embodiments, an antibody that specifically binds a target has a dissociation constant (Kd) of ≤1 μM, ≤100 nM, ≤10 nM, ≤1 nM, or ≤0.1 nM. In certain embodiments, an antibody specifically binds an epitope on a protein that is conserved among the protein from different species. In another embodiment, specific binding can include, but does not require exclusive binding.

The term "specificity" refers to selective recognition of an antigen binding protein or antibody for a particular epitope of an antigen. Natural antibodies, for example, are monospecific. The term "multispecific" as used herein denotes that an antigen binding protein or an antibody has two or more antigen-binding sites of which at least two bind a different antigen or a different epitope of the same antigen. "Bispecific" as used herein denotes that an antigen binding protein or an antibody has two different antigen-binding specificities. The term "monospecific" antibody as used herein denotes an antibody that has one or more binding sites each of which bind the same epitope of the same antigen.

The term "valent" as used herein denotes the presence of a specified number of binding sites in an antigen binding protein or antibody molecule. A natural antibody for example or a full length antibody has two binding sites and is bivalent. As such, the terms "trivalent", "tetravalent", "pentavalent" and "hexavalent" denote the presence of two binding site, three binding sites, four binding sites, five binding sites, and six binding sites, respectively, in an antigen binding protein or antibody molecule. The MABPs of the present application are at least "bivalent," for example, the MABPs can be "trivalent," or "tetravalent."

A "blocking" antibody or an "antagonist" antibody is one that inhibits or reduces a biological activity of the antigen it binds. In some embodiments, blocking antibodies or antagonist antibodies substantially or completely inhibit the biological activity of the antigen.

An "agonist" or activating antibody is one that enhances or initiates signaling by the antigen to which it binds. In some embodiments, agonist antibodies cause or activate signaling without the presence of the natural ligand.

"Antibody effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptors); and B cell activation. "Reduced or minimized" antibody effector function means that which is reduced by at least 50% (alternatively 60%, 65%, 70%, 75%, 80%, 85%, 90%, 95%, 96%, 97%, 98%, 99%) from the wild type or unmodified antibody. The determination of antibody effector function is readily determinable and measurable by one of ordinary skill in the art. In a preferred embodiment, the antibody effector functions of complement binding, complement dependent cytotoxicity and antibody dependent cytotoxicity are affected. In some embodiments, effector function is eliminated through a mutation in the constant region that eliminated glycosylation, e.g., "effector-less mutation." In one aspect, the effector-less mutation is an N297A or DANA mutation (D265A+N297A) in the $C_H2$ region. Shields et al., *J. Biol. Chem.* 276 (9): 6591-6604 (2001). Alternatively, additional mutations resulting in reduced or eliminated effector function include: K322A and L234A/L235A (LALA). Alternatively, effector function can be reduced or eliminated through production techniques, such as expression in host cells that do not glycosylate (e.g., *E. coli.*) or in which result in an altered glycosylation pattern that is ineffective or less effective at promoting effector function (e.g., Shinkawa et al., *J. Biol. Chem.* 278(5): 3466-3473 (2003).

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol.* 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., *PNAS USA* 95:652-656 (1998).

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Fc receptor" or "FcR" describes a receptor that binds the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994). Methods of measuring binding to FcRn are known (see, e.g., Ghetie and Ward, *Immunol. Today* 18: (12): 592-8 (1997); Ghetie et al., *Nature Biotechnology* 15 (7): 637-40 (1997); Hinton et al., *J. Biol. Chem.* 279 (8): 6213-6 (2004); WO 2004/92219 (Hinton et al.). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., *J. Biol. Chem.* 9(2): 6591-6604 (2001).

"Effector cells" are leukocytes which express one or more FcRs and perform effector functions. In one aspect, the effector cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils. The effector cells may be isolated from a native source, e.g., blood. Effector cells generally are lymphocytes associated with the effector phase, and function to produce cytokines (helper T cells), killing cells in infected with pathogens (cytotoxic T cells) or secreting antibodies (differentiated B cells).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202: 163 (1996), may be performed. Antibody variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

The term "heavy chain-only antibody" or "HCAb" refers to a functional antibody, which comprises heavy chains, but lacks the light chains usually found in antibodies. Camelid animals (such as camels, llamas, or alpacas) are known to produce HCAbs.

The term "single-domain antibody" or "sdAb" refers to a single antigen-binding polypeptide having three complementary determining regions (CDRs). The sdAb alone is capable of binding to the antigen without pairing with a corresponding CDR-containing polypeptide. In some cases, sdAbs are engineered from camelid HCAbs, and their heavy chain variable domains are referred herein as "$V_H$Hs". Camelid sdAb is one of the smallest known antigen-binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)).

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present application. Specific illustrative and exemplary embodiments for measuring binding affinity are described in the following.

The "Kd" or "Kd value" as used herein is in one embodiment measured by a radiolabeled antigen binding assay (RIA) performed with the Fab version of the antibody and antigen molecule as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) *J. Mol.*

*Biol* 293:865-881). To establish conditions for the assay, microtiter plates (Dynex) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM [$^{125}$I]-antigen are mixed with serial dilutions of a Fab of interest (consistent with assessment of an anti-VEGF antibody, Fab-12, in Presta et al., (1997) *Cancer Res.* 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature for one hour. The solution is then removed and the plate washed eight times with 0.1% Tween-20 in PBS. When the plates have dried, 150 µl/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays.

According to another embodiment, the Kd is measured by using surface-plasmon resonance assays using a BIA-CORE®-2000 or a BIACORE®-3000 instrument (BIAcore, Inc., Piscataway, N.J.) at 25° C. with immobilized antigen CM5 chips at 10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (0.2 µM) before injection at a flow rate of 5 µL/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN 20™ surfactant (PBST) at 25° C. at a flow rate of approximately 25 L/min. Association rates ($k_{on}$) and dissociation rates ($k_{off}$) are calculated using a simple one-to-one *Langmuir* binding model (BIAcore® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6 M^{-1} s^{-1}$ by the surface-plasmon resonance assay above, then the on-rate can be determined by using a fluorescent quenching technique that measures the increase or decrease in fluorescence-emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow-equipped spectrophotometer (Aviv Instruments) or a 8000-series SLM-AMINCO™ spectrophotometer (ThermoSpectronic) with a stirred cuvette.

An "on-rate," "rate of association," "association rate," or "$k_{on}$" as used herein can also be determined as described above using a BIACORE®-2000 or a BIACORE®-3000 system (BIAcore, Inc., Piscataway, N.J.) at 25° C. with immobilized antigen CM5 chips at about 10 response units (RU). Briefly, carboxymethylated dextran biosensor ships (CM5, BIAcore Inc.) are activated with N-ethyl-N'-(3-dimethylamino propyl)-carbodiimide hydrochloride (ECD) and N-hydroxysuccinimide (NHS) according to the supplier's instructions. Antigen is diluted with 10 mM sodium acetate, pH 4.8, into 5 mg/ml 0.2 mM) before injection at a flow rate of 5 ml/min. to achieve approximately 10 response units (RU) of coupled protein. Following the injection of antigen, 1M ethanolamine is added to block unreacted groups. For kinetics measurements, two-fold serial dilutions of Fab (0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) was calculated as the ratio $k_{off}/k_{on}$. See, e.g., Chen, Y., et al., (1999) *J. Mol. Biol* 293:865-881. However, if the on-rate exceeds $10^6 M^{-1} S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An "isolated" nucleic acid molecule encoding the MABP or sdAb herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugars such as sucrose, mannitol, trehalose or sorbitol; salt-forming counterions such as sodium; metal complexes (e.g. Zn-protein complexes); and/or nonionic surfactants such as TWEEN™, polyethylene glycol (PEG), and PLURONICS™ or polyethylene glycol (PEG).

The "diluent" of interest herein is one which is pharmaceutically acceptable (safe and non-toxic for administration to a human) and is useful for the preparation of a liquid formulation, such as a formulation reconstituted after lyophilization. Exemplary diluents include sterile water, bacteriostatic water for injection (BWFI), a pH buffered solution (e.g. phosphate-buffered saline), sterile saline solution, Ringer's solution or dextrose solution. In an alternative embodiment, diluents can include aqueous solutions of salts and/or buffers.

A "preservative" is a compound which can be added to the formulations herein to reduce bacterial activity. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile. A "sterile" formulation is aseptic or free from all living microorganisms and their spores.

A "stable" formulation is one in which the protein therein essentially retains its physical and chemical stability and integrity upon storage. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month and/or stable at 2-8° C. for at least 2 years. Where the formulation is to be stored at 30° C., generally the formulation should be stable for at least 2 years at 30° C. and/or stable at 40° C. for at least 6 months. For example, the extent of aggregation during storage can be used as an indicator of protein stability. Thus, a "stable" formulation may be one wherein less than about 10% and preferably less than about 5% of the protein are present as an aggregate in the formulation. In other embodiments, any increase in aggregate formation during storage of the formulation can be determined.

A "reconstituted" formulation is one which has been prepared by dissolving a lyophilized protein or antibody formulation in a diluent such that the protein is dispersed throughout. The reconstituted formulation is suitable for administration (e.g. subcutaneous administration) to a patient to be treated with the protein of interest and, in certain embodiments, may be one which is suitable for parenteral or intravenous administration.

An "isotonic" formulation is one which has essentially the same osmotic pressure as human blood. Isotonic formulations will generally have an osmotic pressure from about 250 to 350 mOsm. The term "hypotonic" describes a formulation with an osmotic pressure below that of human blood. Correspondingly, the term "hypertonic" is used to describe a formulation with an osmotic pressure above that of human blood. Isotonicity can be measured using a vapor pressure or ice-freezing type osmometer, for example. The formulations of the present application can be hypertonic as a result of the addition of salt and/or buffer.

"Immune checkpoint molecules" refers to molecules in the immune system that either turn up a signal or turn down a signal. "Stimulatory immune checkpoint molecules" or "co-stimulatory molecules" are immune checkpoint molecules that turn up a signal in the immune system. "Inhibitory immune checkpoint molecules" are immune checkpoint molecules that turn down a signal in the immune system.

It is understood that embodiments described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. Multispecific Antigen Binding Proteins (MABPs)

One aspect of the present application provides a multispecific antigen binding protein (MABP) comprising: (a) a first antigen binding portion comprising a heavy chain variable domain ($V_H$) and a light chain variable domain ($V_L$), wherein the $V_H$ and $V_L$ together form an antigen-binding site that specifically binds a first epitope, and (b) a second antigen binding portion comprising an sdAb that specifically binds a second epitope, wherein the first antigen binding portion and the second antigen binding portion are fused to each other. In some embodiments, the first epitope is from a first immune checkpoint molecule, and the second epitope is from a second immune checkpoint molecule. In some embodiments, the first epitope is from a first tumor antigen, and the second epitope is from a second tumor antigen. In some embodiments, the first epitope is from a tumor antigen, and the second epitope is from a cell surface molecule, such as CD3. In some embodiments, the sdAb is a camelid, humanized, or human sdAb. In some embodiments, the first epitope is from a first pro-inflammatory molecule, and the second epitope is from a second pro-inflammatory molecule. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the first antigen binding portion comprises a full-length 4-chain antibody. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc or IgG4 Fc.

The MABPs of the present application have at least two antigen binding portions that can specifically bind at least two different epitopes. Some of the at least two antigen binding portions may be identical, so long as the MABP has binding sites for two different epitopes. The MABPs can be symmetric or asymmetric. For example, the MABP may comprise one or two copies of the first antigen binding portion, and one to eight copies of the second antigen binding portion. In some embodiments, the MABP comprises two different antigen binding portions that each comprise a $V_H$ domain and a $V_L$ domain that together form a different antigen binding site. For example, the first antigen binding portion can be a bispecific antibody. In some embodiments, the first antigen binding portion is a monospecific full-length antibody or antigen binding fragment thereof, such as a Fab.

In some embodiments, the MABP comprises any one of 1, 2, 3, 4, 5, 6, 7, 8, or more different antigen binding portions that each comprises an sdAb. In some embodiments, two identical sdAbs are fused to each other, which is further fused to the first antigen binding portion. In some embodiments, two different sdAbs are fused to each other, which is further fused to the first antigen binding portion.

The MABPs may have any suitable number of valencies for each epitope, and any suitable number of specificity. In some embodiments, the MABP is bivalent, trivalent, tetravalent, pentavalent, hexavalent, or of higher valencies for the first epitope. In some embodiments, the MABP is bivalent, trivalent, tetravalent, pentavalent, hexavalent, or of higher valencies for the second epitope. In some embodiments, the MABP is bispecific. In some embodiments, the MABP is trispecific. In some embodiments, the MABP is tetraspecific. In some embodiments, the MABP has more than four specificities. Exemplary MABPs are depicted in FIGS. 1-22.

Figure 5:
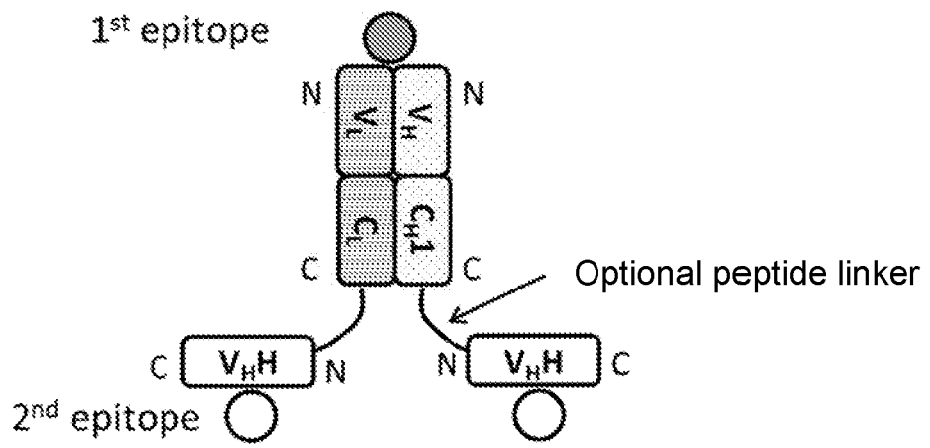
FIG. 5 depicts a schematic structure of an exemplary BABP comprising a monospecific Fab having a heavy chain and a light chain, and two identical sdAbs, wherein the N-terminus of an sdAb is fused to the C-terminus of the heavy chain via an optional peptide linker, and the other sdAb is fused to the C-terminus of the light chain of the Fab via an optional peptide linker. The Fab specifically binds the first epitope. The two sdAbs specifically bind the second epitope. For example, the BABP can consist of two polypeptide chains with structures from the N-terminus to the C-terminus as follows: (1) $V_L$-$C_L$-$V_HH$; and (2) $V_H$-$C_H1$-$V_HH$, wherein $V_H$ and $V_L$ of polypeptide chains (1) and (2) forms an antigen binding site that specifically binds the first epitope, and each $V_HH$ specifically binds a copy of the second epitope. In alternative formats, each sdAb may be omitted, or replaced with two identical or different sdAbs fused to each other.

In some embodiments, there is provided a bispecific antigen binding protein ("BABP") comprising: (a) a single copy of a first antigen binding portion comprising a heavy chain variable domain ($V_H$) and a light chain variable domain ($V_L$), wherein the $V_H$ and $V_L$ together form an antigen-binding site that specifically binds a first epitope, and (b) one or more copies (such as 2) of a second antigen binding portion comprising an sdAb that specifically binds a second epitope, wherein each copy of the second antigen binding portion is fused to the first antigen binding portion. An example is shown in FIG. 5. In some embodiments, one or more of the sdAbs is each further fused to another identical or different sdAb.

In some embodiments, there is provided a MABP comprising: (a) a plurality (such as 2, 3, 4, 5, 6, or more) of a first antigen binding portion comprising a heavy chain variable domain ($V_H$) and a light chain variable domain ($V_L$), wherein the $V_H$ and $V_L$ together form an antigen-binding site that specifically binds a first epitope, and (b) a plurality (such as 2, 3, 4, 5, 6, 7, 8, or more) of identical or different sdAbs that each specifically binds an epitope that is different from the first epitope, wherein the sdAbs are fused to each other, and/or to the first antigen binding portion.

Figure 1:
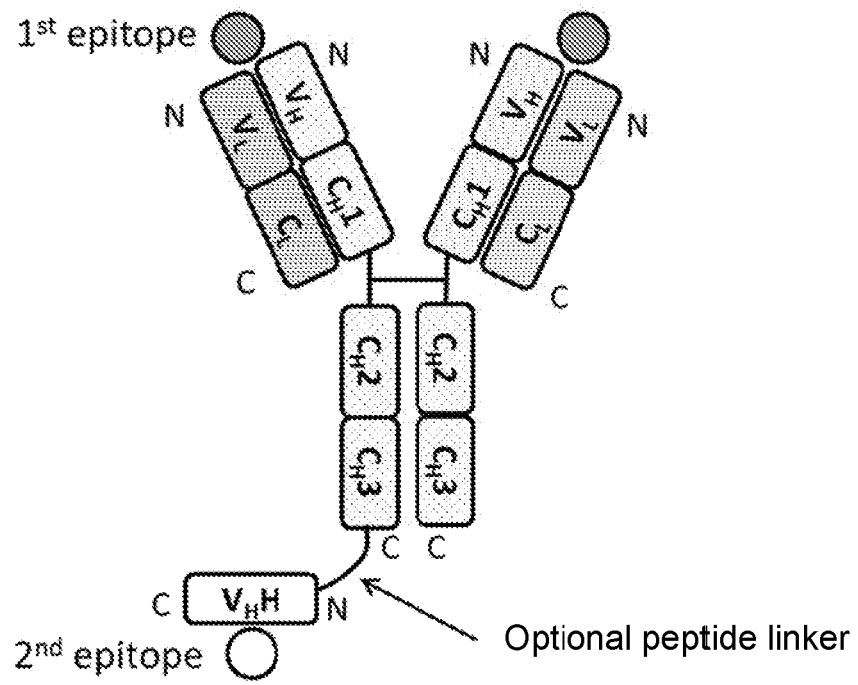
FIG. 1 depicts a schematic structure of an exemplary bispecific antigen binding protein (also referred herein as "BABP") comprising a monospecific full-length antibody having two identical heavy chains and two identical light chains, and an sdAb, wherein the N-terminus of the sdAb is fused to the C-terminus of one heavy chain via an optional peptide linker. The full-length antibody has two antigen binding sites that specifically bind the first epitope. The sdAb specifically binds the second epitope. For example, the BABP can consist of four polypeptide chains with structures from the N-terminus to the C-terminus as follows: (1) $V_L$-$C_L$; (2) $V_H$-$C_H1$-$C_H2$-$C_H3$-$V_HH$; (3) $V_H$-$C_H1$-$C_H2$-$C_H3$; and (4) $V_L$-$C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, and $V_HH$ specifically binds the second epitope.
Figure 2:
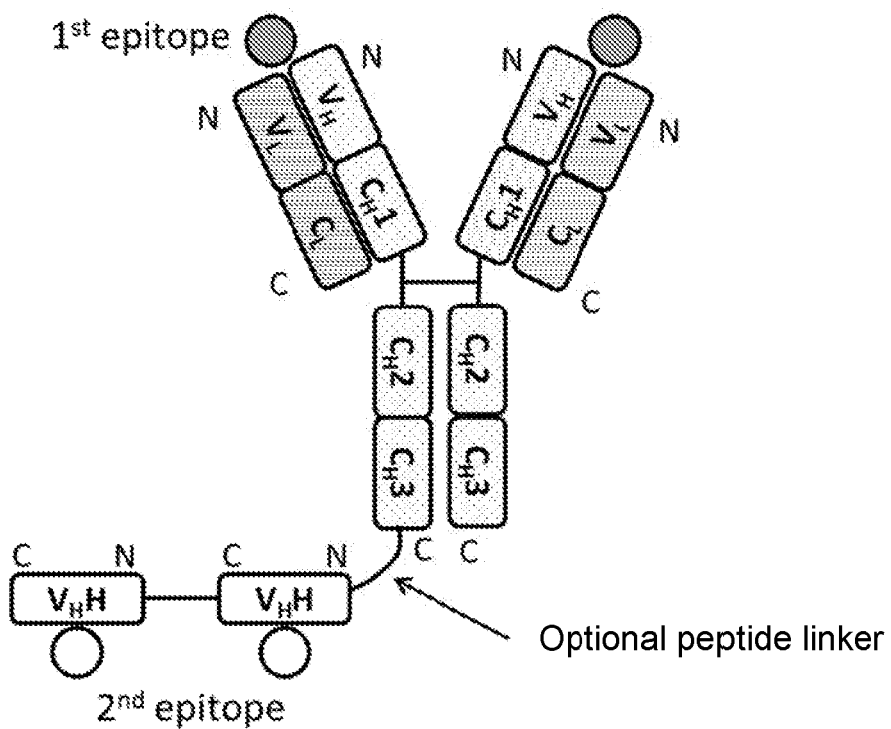
FIG. 2 depicts a schematic structure of an exemplary BABP comprising a monospecific full-length antibody having two identical heavy chains and two identical light chains, and two identical sdAbs, wherein the two sdAbs are fused to each other, and the N-terminus of one sdAb is fused to the C-terminus of a heavy chain via an optional peptide linker. The full-length antibody has two antigen binding sites that specifically bind the first epitope. The two sdAbs specifically bind the second epitope. For example, the BABP can consist of four polypeptide chains with structures from the N-terminus to the C-terminus as follows: (1) $V_L$-$C_L$; (2) $V_H$-$C_H1$-$C_H2$-$C_H3$-$V_HH$-$V_HH$; (3) $V_H$-$C_H1$-$C_H2$-$C_H3$; and (4) $V_L$-$C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, and each $V_HH$ specifically binds a copy of the second epitope.
Figure 3:
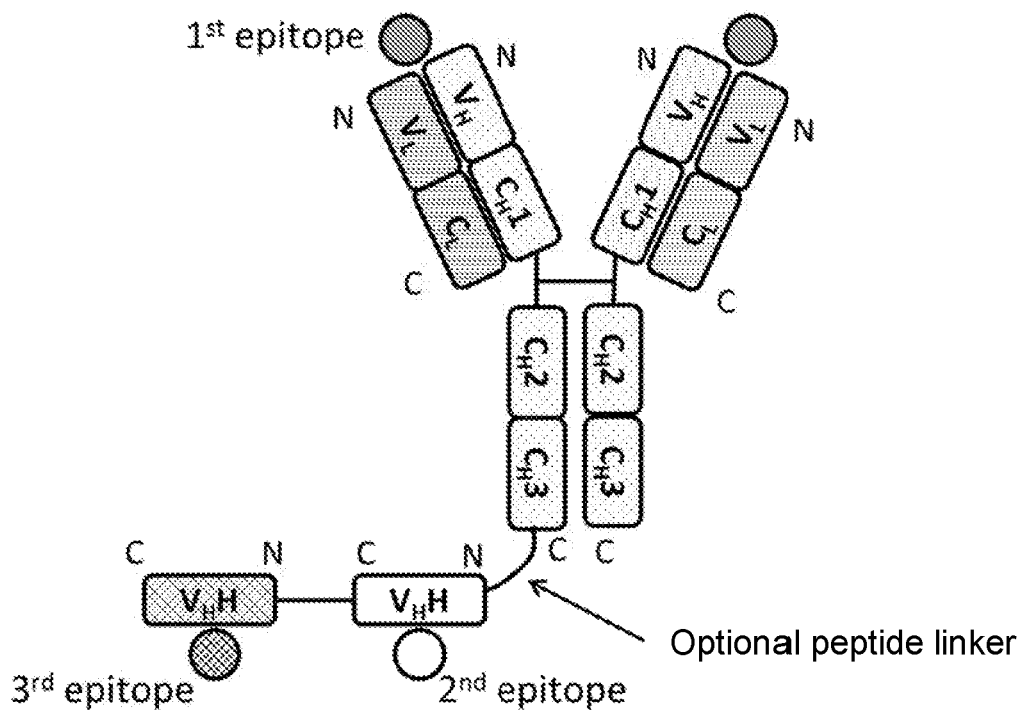
FIG. 3 depicts a schematic structure of an exemplary trispecific antigen binding protein (also referred herein as "TABP") comprising a monospecific full-length antibody having two identical heavy chains and two identical light chains, a first sdAb, and a second sdAb, wherein the first sdAb and the second sdAb are fused to each other via an optional peptide linker, and the N-terminus of the first sdAb is fused to the C-terminus of a heavy chain via an optional peptide linker. The full-length antibody has two antigen binding sites that specifically bind the first epitope. The first sdAb specifically binds the second epitope. The second sdAb specifically binds the third epitope. For example, the TABP can consist of four polypeptide chains with structures from the N-terminus to the C-terminus as follows: (1) $V_L$-$C_L$; (2) $V_H$-$C_H1$-$C_H2$-$C_H3$-$V_HH1$-$V_HH2$; (3) $V_H$-$C_H1$-$C_H2$-$C_H3$; and (4) $V_L$-$C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, $V_HH1$ specifically binds the second epitope, and $V_HH2$ specifically binds the third epitope.

In some embodiments, there is provided a multispecific (such as bispecific) antigen binding protein comprising: (a) two copies of a first antigen binding portion each comprising a heavy chain variable domain ($V_H$) and a light chain variable domain ($V_L$), wherein the $V_H$ and $V_L$ together form an antigen-binding site that specifically binds a first epitope, and (b) a single copy of a second antigen binding portion comprising an sdAb that specifically binds a second epitope, wherein the second antigen binding portion is fused to one of the two copies of the first antigen binding portion. An example is shown in FIG. 1.

In some embodiments, there is provided a multispecific (such as bispecific) antigen binding protein comprising: (a) two copies of a first antigen binding portion each comprising a heavy chain variable domain ($V_H$) and a light chain variable domain ($V_L$), wherein the $V_H$ and $V_L$ together form an antigen-binding site that specifically binds a first epitope, and (b) a plurality (such as 2, 3, or 4) of identical or different sdAbs that each specifically binds an epitope that is different from the first epitope, wherein the sdAbs are fused to each other, and/or to the first antigen binding portion. Examples are shown in FIGS. 2, 3, 17, 18, 21, and 22.

In some embodiments, there is provided a multispecific (such as bispecific) antigen binding protein comprising: (a) two copies of a first antigen binding portion each comprising a heavy chain variable domain ($V_H$) and a light chain variable domain ($V_L$), wherein the $V_H$ and $V_L$ together form an antigen-binding site that specifically binds a first epitope, and (b) two copies of a second antigen binding portion each comprising an sdAb that specifically binds a second epitope, wherein one copy of the second antigen binding portion is fused to each copy of the first antigen binding portion. Examples are shown in FIGS. 4, 9, 11, 13, 19, and 20. In some embodiments, one or more of the sdAbs is each further fused to another identical or different sdAb.

In some embodiments, there is provided a multispecific (such as trispecific) antigen binding protein comprising: (a) a first copy and a second copy of a first antigen binding portion each comprising a heavy chain variable domain ($V_H$) and a light chain variable domain ($V_L$), wherein the $V_H$ and $V_L$ together form an antigen-binding site that specifically binds a first epitope, (b) a second antigen binding portion comprising an sdAb that specifically binds a second epitope, and (c) a third antigen binding portion comprising a second sdAb that specifically binds a third epitope, wherein the second antigen binding portion is fused to the first copy of the first antigen binding portion, and wherein the third antigen binding portion is fused to the second copy of the first antigen binding portion. Examples are shown in FIGS. 7, 10, 12, and 14. In some embodiments, one or more of the sdAbs is each further fused to another identical or different sdAb.

Figure 6:
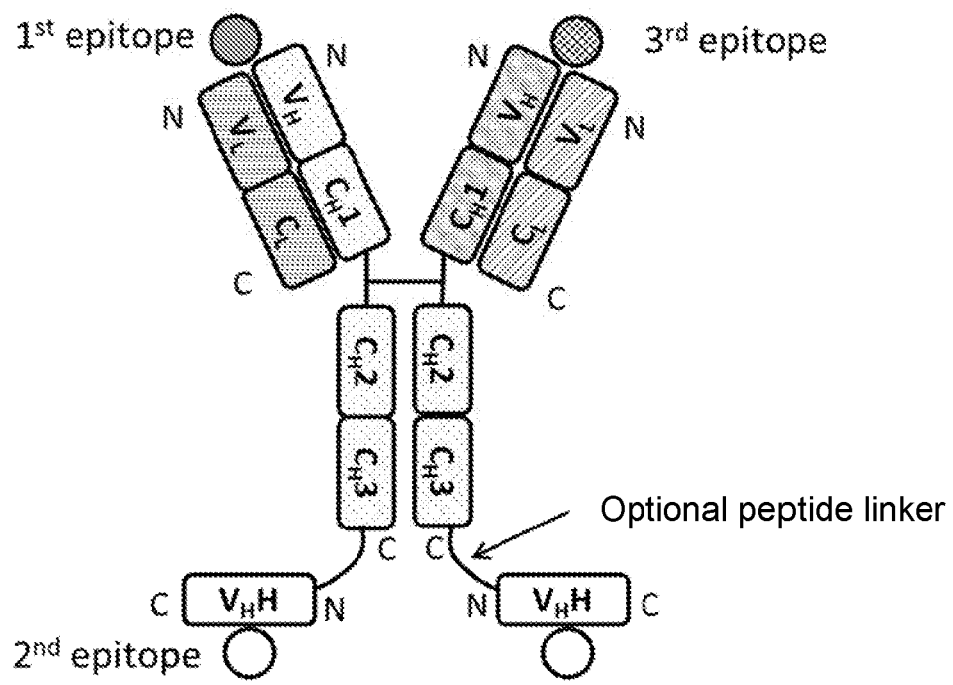
FIG. 6 depicts a schematic structure of an exemplary TABP comprising a bispecific full-length antibody having two heavy chains and two light chains, and two identical sdAbs, wherein the N-terminus of each sdAb is fused to one heavy chain via an optional peptide linker. The full-length antibody has a first antigen binding site that specifically binds the first epitope, and a second antigen binding site that specifically binds the third epitope. The two sdAbs specifically bind to the second epitope. For example, the TABP can consist of four polypeptide chains with structures from the N-terminus to the C-terminus as follows: (1) $V_L1$-$C_L$; (2) $V_H1$-$C_H1$-$C_H2$-$C_H3$-$V_HH$; (3) $V_H2$-$C_H1$-$C_H2$-$C_H3$-$V_HH$; and (4) $V_L2$-$C_L$, wherein $V_H1$ and $V_L1$ of polypeptide chains (1) and (2) forms an antigen binding site that specifically binds the first epitope, $V_H2$ and $V_L2$ of polypeptide chains (3) and (4) forms an antigen binding site that specifically binds the third epitope, and each $V_HH$ specifically binds a copy of the second epitope. In alternative formats, each sdAb may be omitted, or replaced with two identical or different sdAbs fused to each other.
Figure 7:
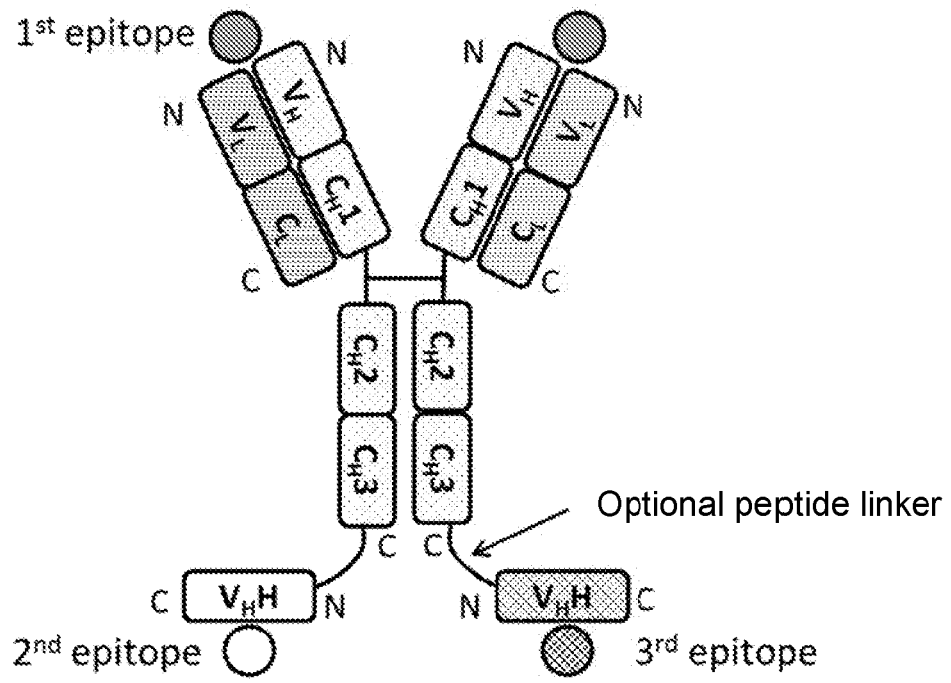
FIG. 7 depicts a schematic structure of an exemplary TABP comprising a monospecific full-length antibody having two identical heavy chains and two identical light chains, a first sdAb, and a second sdAb, wherein the N-terminus of each sdAb is fused to one heavy chain via an optional peptide linker. The full-length antibody has two antigen binding sites that specifically bind the first epitope. The first sdAb specifically binds the second epitope. The second sdAb specifically binds the third epitope. For example, the TABP can consist of four polypeptide chains with structures from the N-terminus to the C-terminus as follows: (1)

In some embodiments, there is provided a multispecific (such as trispecific) antigen binding protein comprising: (a) a first antigen binding portion comprising a first heavy chain variable domain ($V_H$) and a first light chain variable domain ($V_L$), wherein the first $V_H$ and first $V_L$ together form a first antigen-binding site that specifically binds a first epitope; (b) one to four copies of a second antigen binding portion comprising an sdAb that specifically binds a second epitope; and (c) a third antigen binding portion comprising a third heavy chain variable domain ($V_H$) and a third light chain variable domain ($V_L$), wherein the third $V_H$ and third $V_L$ together form a third antigen-binding site that specifically binds a third epitope; and wherein the second antigen binding portion is fused to the first antigen binding portion and/or the third antigen binding portion. An example is shown in FIG. 6. In some embodiments, one or more of the sdAbs is each further fused to another identical or different sdAb.

In some embodiments, there is provided a multispecific (such as tetraspecific) antigen binding protein comprising: (a) a first antigen binding portion comprising a first heavy chain variable domain ($V_H$) and a first light chain variable domain ($V_L$), wherein the first $V_H$ and first $V_L$ together form a first antigen-binding site that specifically binds a first epitope; (b) a second antigen binding portion comprising an sdAb that specifically binds a second epitope; (c) a third antigen binding portion comprising a third heavy chain variable domain ($V_H$) and a third light chain variable domain ($V_L$), wherein the third $V_H$ and third $V_L$ together form a third antigen-binding site that specifically binds a third epitope; and (d) a fourth antigen binding portion comprising a second sdAb that specifically binds a fourth epitope; wherein the first antigen binding portion and the second antigen binding portion are fused to each other, and wherein the third antigen binding portion and the fourth antigen binding portion are fused to each other. An example is shown in FIG. 8. In some embodiments, one or more of the sdAbs is each further fused to another identical or different sdAb.

Epitopes and Antigens

Any of the MABPs described herein can specifically bind at least two different epitopes. The at least two different epitopes recognized can be located on the same antigen, or on different antigens. In some embodiments, the antigens are cell surface molecules. In some embodiments, the antigens are extracellular molecules.

Thus, in some embodiments, there is provided a multispecific (such as bispecific) antigen binding protein comprising: (a) a first antigen binding portion comprising a heavy chain variable domain ($V_H$) and a light chain variable domain ($V_L$), wherein the $V_H$ and $V_L$ together form an antigen-binding site that specifically binds a first antigen, and (b) a second antigen binding portion comprising an sdAb that specifically binds a second antigen, wherein the first antigen binding portion and the second antigen binding portion are fused to each other. In some embodiments, the sdAb is a camelid, humanized, or human sdAb. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the first antigen binding portion comprises a full-length 4-chain antibody. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc or IgG4 Fc.

In some embodiments, the first epitope and/or the second epitope is an immune checkpoint molecule. In some embodiments, the immune checkpoint molecule is a stimulatory immune checkpoint molecule. Exemplary stimulatory immune checkpoint molecules include, but are not limited to, CD28, OX40, ICOS, GITR, 4-1BB, CD27, CD40, CD3, HVEM, and TCR (e.g., MHC class I or class II molecules). In some embodiments, the immune checkpoint molecule is an inhibitory immune checkpoint molecule. Exemplary inhibitory immune checkpoint molecules include, but are not limited to, CTLA-4, TIM-3, A2a Receptor, LAG-3, BTLA, KIR, PD-1, IDO, CD47, and ligands thereof such as B7.1, B7.2, PD-L1, PD-L2, HVEM, B7-H4, NKTR-218, and SIRP-alpha receptor.

Thus, in some embodiments, there is provided a multispecific (such as bispecific) antigen binding protein comprising: (a) a first antigen binding portion comprising a heavy chain variable domain ($V_H$) and a light chain variable domain ($V_L$), wherein the $V_H$ and $V_L$ together form an antigen-binding site that specifically binds a first immune checkpoint molecule, and (b) a second antigen binding portion comprising an sdAb that specifically binds a second immune checkpoint molecule, wherein the first antigen binding portion and the second antigen binding portion are fused to each other. In some embodiments, the sdAb is a camelid, humanized, or human sdAb. In some embodiments, the first immune checkpoint molecule and/or the second immune checkpoint molecule is selected from the group consisting of PD-1, PD-L1, PD-L2, CTLA-4, B7-H3, TIM-3, LAG-3, VISTA, ICOS, 4-1BB, OX40, GITR, and CD40. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the first antigen binding portion comprises a full-length 4-chain antibody. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG4 Fc.

In some embodiments, the first epitope and/or the second epitope is a cell surface antigen. In some embodiments, the cell surface antigen is an antigen on immune effector cells, such as T cells (e.g., helper T cells, cytotoxic T cells, memory T cells, etc.), B cells, macrophages, and Natural Killer (NK) cells. In some embodiments, the cell surface antigen is a T cell surface antigen, such as CD3.

In some embodiments, the cell surface antigen is a tumor antigen. Tumor antigens are proteins that are produced by tumor cells that can elicit an immune response, particularly T-cell mediated immune responses. The selection of the targeted antigen described herein will depend on the particular type of cancer to be treated. Exemplary tumor antigens include, for example, a glioma-associated antigen, carcinoembryonic antigen (CEA), β-human chorionic gonadotropin, alphafetoprotein (AFP), lectin-reactive AFP, thyroglobulin, RAGE-1, MN-CAIX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, HER2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In some embodiments, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and gp100 in melanoma and prostatic acid phosphatase (PAP) and prostate-specific antigen (PSA) in prostate cancer. Other target molecules belong to the group of transformation-related molecules such as the oncogene HER2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD 19, CD20 and CD37 are other candidates for target antigens in B-cell lymphoma.

In some embodiments, the tumor antigen is a tumor-specific antigen (TSA) or a tumor-associated antigen (TAA). A TSA is unique to tumor cells and does not occur on other cells in the body. A TAA associated antigen is not unique to a tumor cell, and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development, when the immune system is immature, and unable to respond or they may be antigens that are normally present at extremely low levels on normal cells, but which are expressed at much higher levels on tumor cells.

Non-limiting examples of TSA or TAA antigens include the following: Differentiation antigens such as MART-1/MelanA (MART-I), gp 100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, pl85erbB2, pl80erbB-3, c-met, nm-23HI, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3CA 27.29BCAA, CA 195, CA 242, CA-50, CAM43, CD68P1, CO-029, FGF-5, G250, Ga733EpCAM, HTgp-175, M344, MA-50, MG7-Ag, MOV18, NB/70K, NY-CO-1, RCAS 1, SDCCAG16, TA-90Mac-2 binding protein\cyclophilin C-associated protein, TAAL6, TAG72, TLP, and TPS.

Thus, in some embodiments, there is provided a multispecific (such as bispecific) antigen binding protein comprising: (a) a first antigen binding portion comprising a heavy chain variable domain ($V_H$) and a light chain variable domain ($V_L$), wherein the $V_H$ and $V_L$ together form an antigen-binding site that specifically binds a first tumor antigen, and (b) a second antigen binding portion comprising an sdAb that specifically binds a second tumor antigen, wherein the first antigen binding portion and the second antigen binding portion are fused to each other. In some embodiments, the sdAb is a camelid, humanized, or human sdAb. In some embodiments, the first tumor antigen and/or the second tumor antigen is selected from the group consisting of HER2, BRAF, EGFR, VEGFR2, CD20, RANKL, CD38, and CD52. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the first antigen binding portion comprises a full-length 4-chain antibody. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc.

In some embodiments, there is provided a multispecific (such as bispecific) antigen binding protein comprising: (a) a first antigen binding portion comprising a heavy chain variable domain ($V_H$) and a light chain variable domain ($V_L$), wherein the $V_H$ and $V_L$ together form an antigen-binding site that specifically binds a tumor antigen, and (b) a second antigen binding portion comprising an sdAb that specifically binds a cell surface antigen on an immune effector cell (such as T cell), wherein the first antigen binding portion and the second antigen binding portion are fused to each other. In some embodiments, the sdAb is a camelid, humanized, or human sdAb. In some embodiments, the tumor antigen is selected from the group consisting of HER2, BRAF, EGFR, VEGFR2, CD20, RANKL, CD38, and CD52. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the first antigen binding portion comprises a full-length 4-chain antibody. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc or IgG4 Fc.

In some embodiments, the first epitope and/or the second epitope is a pro-inflammatory molecule. "Pro-inflammatory molecule" refers to any molecule produced or expressed by an immune cell (such as monocytes, macrophages, lymphocytes and leukocytes) that up-regulates inflammatory reactions. In some embodiments, the pro-inflammatory molecule is a pro-inflammatory cytokine, such as lymphokine, monokine, chemokine, or interleukin. Exemplary pro-inflammatory molecules include, but are not limited to, IL-1β, TNF-α, IL-6, IL-6R, IL-5, IL-17, IL-23, IL-22, IL-21, IL-12, and eotaxin-1 (i.e., CCL11).

Thus, in some embodiments, there is provided a multi-specific (such as bispecific) antigen binding protein comprising: (a) a first antigen binding portion comprising a heavy chain variable domain ($V_H$) and a light chain variable domain ($V_L$), wherein the $V_H$ and $V_L$ together form an antigen-binding site that specifically binds a first pro-inflammatory molecule, and (b) a second antigen binding portion comprising an sdAb that specifically binds a second pro-inflammatory molecule, wherein the first antigen binding portion and the second antigen binding portion are fused to each other. In some embodiments, the sdAb is a camelid, humanized, or human sdAb. In some embodiments, the first pro-inflammatory molecule and/or the second pro-inflammatory molecule is selected from the group consisting of IL-1β, TNF-α, IL-5, IL-6, IL-6R, and eotaxin-1. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the first antigen binding portion comprises a full-length 4-chain antibody. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc.

In some embodiments, the first epitope and/or the second epitope is an angiogenic factor, such as Ang2 and VEGF. Thus, in some embodiments, there is provided a multispecific (such as bispecific) antigen binding protein comprising: (a) a first antigen binding portion comprising a heavy chain variable domain ($V_H$) and a light chain variable domain ($V_L$), wherein the $V_H$ and $V_L$ together form an antigen-binding site that specifically binds a first angiogenic factor, and (b) a second antigen binding portion comprising an sdAb that specifically binds a second angiogenic factor, wherein the first antigen binding portion and the second antigen binding portion are fused to each other.

Fusion Polypeptides

The first antigen binding portion and the second antigen binding portion of the MABP are fused (i.e., covalently linked) to each other. Thus, the MABPs of the present application comprise one or more fusion polypeptides. Each fusion polypeptide may comprise the second antigen binding portion and a polypeptide from the first antigen binding portion.

The first antigen binding portion and the second antigen binding portion may be linked directly by a single chemical bond (such as peptide bond) or via a peptide linker. The second antigen binding portion may be fused at either the N-terminus or the C-terminus of any one (including each) polypeptide of the first antigen binding portion, or may be fused at an internal position of any one (including each) polypeptide of the first antigen binding portion, such as at the N-terminus of the Fc region in the heavy chain of the first antigen binding portion. The fusion polypeptides may be obtained either recombinantly or chemically. In some embodiments, the C-terminus of the second antigen binding portion is fused to the N-terminus of any (including each) polypeptide of the first antigen binding portion via a chemical bond (such as peptide bond) or a peptide linker. In some embodiments, the N-terminus of the second antigen binding portion is fused to the C-terminus of any (including each) polypeptide of the first antigen binding portion via a chemical bond (such as peptide bond) or a peptide linker. In some embodiments, the second antigen binding portion is fused to the first antigen binding portion via a chemical bond that is not a peptide bond involving the main chain chemical groups of amino acids.

In some embodiments, the first antigen binding portion comprises a single-chain antibody fragment comprising the $V_H$ and $V_L$. In some embodiments, the first antigen binding portion comprises an scFv. In some embodiments, the MABP comprises a fusion polypeptide comprising in the N-terminus to C-terminus direction: the second antigen binding portion comprising the sdAb, an optional peptide linker, the $V_H$ domain and the $V_L$ domain. In some embodiments, the MABP comprises a fusion polypeptide comprising in the N-terminus to C-terminus direction: the second antigen binding portion comprising the sdAb, an optional peptide linker, the $V_L$ domain and the $V_H$ domain. In some embodiments, the MABP comprises a fusion polypeptide comprising in the N-terminus to C-terminus direction: the $V_H$ domain, the $V_L$ domain, an optional peptide linker, and the second antigen binding portion comprising the sdAb. In some embodiments, the MABP comprises a fusion polypeptide comprising in the N-terminus to C-terminus direction: the $V_L$ domain, the $V_H$ domain, an optional peptide linker, and the second antigen binding portion comprising the sdAb.

In some embodiments, the first antigen binding portion comprises a heavy chain comprising the $V_H$ domain, and a light chain comprising the $V_L$ domain. In some embodiments, the heavy chain further comprises one or more heavy chain constant domains, such as $C_H1$, $C_H2$, $C_H4$, and $C_H3$, and/or an antibody hinge region (HR). In some embodiments, the light chain further comprises a light chain constant domain ($C_L$), such as the lambda $C_L$ domain or kappa $C_L$ domain. In some embodiments, the N-terminus of the second antigen binding portion is fused to the C-terminus of the heavy chain. In some embodiments, the C-terminus of the second antigen binding portion is fused to the N-terminus of the heavy chain. In some embodiments, the N-terminus of the second antigen binding portion is fused to the C-terminus of the light chain. In some embodiments, the C-terminus of the second antigen binding portion is fused to the N-terminus of the light chain. In some embodiments, the MABP comprises a first polypeptide comprising from the N-terminus to the C-terminus: the heavy chain, an optional peptide linker, and the second antigen binding portion comprising the sdAb; and a second polypeptide comprising the light chain. In some embodiments, the MABP comprises a first polypeptide comprising from the N-terminus to the C-terminus: the second antigen binding portion comprising the sdAb, an optional peptide linker, and the heavy chain; and a second polypeptide comprising the light chain. In some embodiments, the MABP comprises a first polypeptide comprising from the N-terminus to the C-terminus: the light chain, an optional peptide linker, and the second antigen binding portion comprising the sdAb; and a second polypeptide comprising the heavy chain. In some embodiments, the MABP comprises a first polypeptide comprising from the N-terminus to the C-terminus: the second antigen binding portion comprising the sdAb, an optional peptide linker, and the light chain; and a second polypeptide comprising the heavy chain.

In some embodiments, the first antigen binding portion comprises a full-length antibody consisting of two heavy chains and two light chains. In some embodiments, the full-length antibody is a full-length monoclonal antibody consisting of two identical heavy chains and two identical light chains. In some embodiments, the MABP comprises two identical first polypeptides each comprising from the N-terminus to the C-terminus: the heavy chain, an optional peptide linker, and the second antigen binding portion comprising the sdAb; and two second polypeptides each comprising the light chain (see, for example, FIG. 4). In some embodiments, the MABP comprises two identify first polypeptides each comprising from the N-terminus to the C-terminus: the second antigen binding portion comprising the sdAb, an optional peptide linker, and the heavy chain; and two identical second polypeptides each comprising the light chain (see, for example, FIG. 9). In some embodiments, the MABP comprises two identical first polypeptides each comprising from the N-terminus to the C-terminus: the light chain, an optional peptide linker, and the second antigen binding portion comprising the sdAb; and two identical second polypeptides each comprising the heavy chain (see, for example, FIG. 11). In some embodiments, the MABP comprises two identical first polypeptides each comprising from the N-terminus to the C-terminus: the second antigen binding portion comprising the sdAb, an optional peptide linker, and the light chain; and two identical second polypeptides comprising the heavy chain (see, for example, FIG. 13).

In some embodiments, the MABP comprises: (a) a full-length antibody consisting of two heavy chains and two light chains, wherein the full-length antibody specifically recognizes a first epitope; (b) a first sdAb that specifically recognizes a second epitope; and (c) a second sdAb that specifically recognizes a third epitope, wherein the C-terminus of the first sdAb is fused to the N-terminus of each heavy chain, and wherein the N-terminus of the second sdAb is fused to the C-terminus of each heavy chain. In some embodiments, the MABP comprises two identical first polypeptides each comprising from the N-terminus to the C-terminus: the first sdAb, an optional peptide linker, the heavy chain, an optional peptide linker, and the second sdAb; and two identical second polypeptides each comprising the light chain. See, for example, FIG. 15.

In some embodiments, the MABP comprises: (a) a full-length antibody consisting of two heavy chains and two light chains, wherein the full-length antibody specifically recognizes a first epitope; (b) a first sdAb that specifically recognizes a second epitope; and (c) a second sdAb that specifically recognizes a third epitope, wherein the C-terminus of the first sdAb is fused to the N-terminus of each light chain, and wherein the N-terminus of the second sdAb is fused to the C-terminus of each heavy chain. In some embodiments, the MABP comprises two identical first polypeptides each comprising from the N-terminus to the C-terminus: the heavy chain, an optional peptide linker, and the second sdAb; and two identical second polypeptides each comprising the first sdAb, an optional peptide linker, and the light chain. See, for example, FIG. 16.

In some embodiments, the MABP comprises: (a) a full-length antibody consisting of a first and a second heavy chains and a first and a second light chains, wherein the full-length antibody specifically recognizes a first epitope; (b) a first sdAb that specifically recognizes a second epitope; (c) a second sdAb that specifically recognizes a third epitope; (d) a third sdAb that specifically recognizes a fourth epitope; and (e) a fourth sdAb that specifically recognizes a fifth epitope; wherein the C-terminus of the first sdAb is fused to the N-terminus of the first light chain, wherein the C-terminus of the second sdAb is fused to the N-terminus of the second light chain, wherein the C-terminus of the third sdAb is fused to the N-terminus of the first heavy chain, and wherein the C-terminus of the fourth sdAb is fused to the N-terminus of the second heavy chain. In some embodiments, the MABP comprises two identical first polypeptides each comprising from the N-terminus to the C-terminus: the third or the fourth sdAb, an optional peptide linker, and the heavy chain; and two identical second polypeptides each comprising the first or the second sdAb, an optional peptide linker, and the light chain. See, for example, FIG. 17.

In some embodiments, the MABP comprises: (a) a full-length antibody consisting of two heavy chains and two light chains, wherein the full-length antibody specifically recognizes a first epitope; (b) a first sdAb that specifically recognizes a second epitope; (c) a second sdAb that specifically recognizes a third epitope; (d) a third sdAb that specifically recognizes a fourth epitope; and (e) a fourth sdAb that specifically recognizes a fifth epitope; wherein the C-terminus of the first sdAb is fused to the N-terminus of the second sdAb, and the C-terminus of the second sdAb is fused to the N-terminus of one heavy chain, and wherein the C-terminus of the third sdAb is fused to the N-terminus of the fourth sdAb, and the C-terminus of the fourth sdAb is fused to the N-terminus of the other heavy chain. In some embodiments, the MABP comprises two identical first polypeptides each comprising from the N-terminus to the C-terminus: the first or the third sdAb, an optional peptide linker, the second or the fourth sdAb, an optional peptide linker, and the heavy chain; and two identical second polypeptides each comprising the light chain. See, for example, FIG. 18.

In some embodiments, the MABP comprises: (a) a full-length antibody consisting of two heavy chains and two light chains, wherein the full-length antibody specifically recognizes a first epitope; (b) a first sdAb that specifically recognizes a second epitope; and (c) a second sdAb that specifically recognizes a third epitope, wherein the N-terminus of the first or the second sdAb is fused to the C-terminus of the $C_H1$ region of the heavy chain, and the C-terminus of the first or the second sdAb is fused to the N-terminus of the $C_H2$ region of the heavy chain. In some embodiments, the MABP comprises two identical first polypeptides each comprising from the N-terminus to the C-terminus: $V_H$—$C_H1$-an optional peptide linker-sdAb-$C_H2$-$C_H3$; and two identical second polypeptides each comprising the light chain. See, for example, FIG. 19.

In some embodiments, the MABP comprises: (a) a first scFv that specifically recognizes a first epitope; (b) a second scFv that specifically recognizes a second epitope; (c) an Fc region; (d) a first sdAb that specifically recognizes a third epitope; and (d) a second sdAb that specifically recognizes a fourth epitope, wherein the N-terminus of each sdAb is fused to the C-terminus of an scFv and the C-terminus of the sdAb is fused to the N-terminus of the Fc region. In some embodiments, the MABP comprises two identical polypeptides each comprising from the N-terminus to the C-terminus: scFv-an optional peptide linker-sdAb-CH2-CH3. See, for example, FIG. 20.

In some embodiments, the MABP comprises: (a) a first Fab that specifically recognizes a first epitope; (b) a second Fab that specifically recognizes a second epitope; (c) an Fc region; (d) a first Fab-like domain comprising a first sdAb that specifically recognizes a third epitope and a second sdAb that specifically recognizes a fourth epitope; (e) a second Fab-like domain comprising a third sdAb that specifically recognizes a fifth epitope and a fourth sdAb that specifically recognizes a sixth epitope, wherein the N-termini of each Fab-like domain are fused to the C-termini of a Fab and one of the two C-termini of the Fab-like domain is fused to the N-terminus of the Fc region. In some embodiments, the MABP comprises two identical first polypeptides each comprising from the N-terminus to the C-terminus: $V_H$—$C_H1$-an optional peptide linker-sdAb-$C_H1$-$C_H2$-$C_H3$; and two identical second polypeptides each comprising from the N-terminus to the C-terminus: $V_L$—$C_L$-an optional peptide linker-sdAb-$C_L$. See, for example, FIG. 21.

In some embodiments, the MABP comprises: (a) a first scFv that specifically recognizes a first epitope; (b) a second scFv that specifically recognizes a second epitope; (c) an Fc region; (d) a first Fab-like domain comprising a first sdAb that specifically recognizes a third epitope and a second sdAb that specifically recognizes a fourth epitope; (e) a second Fab-like domain comprising a third sdAb that specifically recognizes a fifth epitope and a fourth sdAb that specifically recognizes a sixth epitope, wherein one of the two N-termini of each Fab-like domain is fused to the C-terminus of an scFv and one of the two C-termini of the sdAb is fused to an N-terminus of the Fc region. In some embodiments, the MABP comprises two identical first polypeptides each comprising from the N-terminus to the C-terminus: scFv-an optional peptide linker-sdAb-$C_H1$-$C_H2$-$C_H3$; and two identical second polypeptides each comprising from the N-terminus to the C-terminus: sdAb-$C_L$. See, for example, FIG. 22.

Thus, in some embodiments, there is provided a multispecific (such as bispecific) antigen binding protein comprising: (a) a first antigen binding portion comprising a heavy chain comprising a heavy chain variable domain ($V_H$) and a light chain comprising a light chain variable domain ($V_L$), wherein the $V_H$ and $V_L$ together form an antigen-binding site that specifically binds a first epitope, and (b) a second antigen binding portion comprising an sdAb that specifically binds a second epitope, wherein the N-terminus of the second antigen binding portion is fused to the C-terminus of the heavy chain of the first antigen binding portion via a peptide bond or a peptide linker. In some embodiments, the sdAb is a camelid, humanized, or human sdAb. In some embodiments, the first epitope is from a first immune checkpoint molecule, and the second epitope is from a second immune checkpoint molecule. In some embodiments, the first epitope is from a first tumor antigen, and the second epitope is from a second tumor antigen. In some embodiments, the first epitope is from a tumor antigen, and the second epitope is from a cell surface molecule, such as CD3. In some embodiments, the first epitope is from a first pro-inflammatory molecule, and the second epitope is from a second pro-inflammatory molecule. In some embodiments, the first epitope is from a first angiogenic factor, and the second epitope is from a second angiogenic factor. In some embodiments, the peptide linker is no more than about 30 (such as no more than about any one of 25, 20, or 15) amino acids long. In some embodiments, the first antigen binding fragment comprises an Fc region, such as an IgG1 Fc or IgG4 Fc.

In some embodiments, there is provided a multispecific (such as bispecific) antigen binding protein comprising: (a) a first antigen binding portion comprising a heavy chain comprising a heavy chain variable domain ($V_H$) and a light chain comprising a light chain variable domain ($V_L$), wherein the $V_H$ and $V_L$ together form an antigen-binding site that specifically binds a first epitope, and (b) a second antigen binding portion comprising an sdAb that specifically binds a second epitope, wherein the C-terminus of the second antigen binding portion is fused to the N-terminus of the heavy chain of the first antigen binding portion via a peptide bond or a peptide linker. In some embodiments, the sdAb is a camelid, humanized, or human sdAb. In some embodiments, the first epitope is from a first immune checkpoint molecule, and the second epitope is from a second immune checkpoint molecule. In some embodiments, the first epitope is from a first tumor antigen, and the second epitope is from a second tumor antigen. In some embodiments, the first epitope is from a tumor antigen, and the second epitope is from a cell surface molecule, such as CD3. In some embodiments, the first epitope is from a first pro-inflammatory molecule, and the second epitope is from a second pro-inflammatory molecule. In some embodiments, the first epitope is from a first angiogenic factor, and the second epitope is from a second angiogenic factor. In some embodiments, the peptide linker is no more than about 30 (such as no more than about any one of 25, 20, or 15) amino acids long. In some embodiments, the first antigen binding fragment comprises an Fc region, such as an IgG1 Fc or IgG4 Fc.

In some embodiments, there is provided a multispecific (such as bispecific) antigen binding protein comprising: (a) a first antigen binding portion comprising a heavy chain comprising a heavy chain variable domain ($V_H$) and a light chain comprising a light chain variable domain ($V_L$), wherein the $V_H$ and $V_L$ together form an antigen-binding site that specifically binds a first epitope, and (b) a second antigen binding portion comprising an sdAb that specifically binds a second epitope, wherein the N-terminus of the second antigen binding portion is fused to the C-terminus of the light chain of the first antigen binding portion via a peptide bond or a peptide linker. In some embodiments, the sdAb is a camelid, humanized, or human sdAb. In some embodiments, the first epitope is from a first immune checkpoint molecule, and the second epitope is from a second immune checkpoint molecule. In some embodiments, the first epitope is from a first tumor antigen, and the second epitope is from a second tumor antigen. In some embodiments, the first epitope is from a tumor antigen, and the second epitope is from a cell surface molecule, such as CD3. In some embodiments, the first epitope is from a first pro-inflammatory molecule, and the second epitope is from a second pro-inflammatory molecule. In some embodiments, the first epitope is from a first angiogenic factor, and the second epitope is from a second angiogenic factor. In some embodiments, the peptide linker is no more than about 30 (such as no more than about any one of 25, 20, or 15) amino acids long. In some embodiments, the first antigen binding fragment comprises an Fc region, such as an IgG1 Fc or IgG4 Fc.

In some embodiments, there is provided a multispecific (such as bispecific) antigen binding protein comprising: (a) a first antigen binding portion comprising a heavy chain comprising a heavy chain variable domain ($V_H$) and a light chain comprising a light chain variable domain ($V_L$), wherein the $V_H$ and $V_L$ together form an antigen-binding site that specifically binds a first epitope, and (b) a second antigen binding portion comprising an sdAb that specifically binds a second epitope, wherein the C-terminus of the second antigen binding portion is fused to the N-terminus of the light chain of the first antigen binding portion via a peptide bond or a peptide linker. In some embodiments, the sdAb is a camelid, humanized, or human sdAb. In some embodiments, the first epitope is from a first immune checkpoint molecule, and the second epitope is from a second immune checkpoint molecule. In some embodiments, the first epitope is from a first tumor antigen, and the second epitope is from a second tumor antigen. In some embodiments, the first epitope is from a tumor antigen, and the second epitope is from a cell surface molecule, such as CD3. In some embodiments, the first epitope is from a first pro-inflammatory molecule, and the second epitope is from a second pro-inflammatory molecule. In some embodiments, the first epitope is from a first angiogenic factor, and the second epitope is from a second angiogenic factor. In some embodiments, the peptide linker is no more than about 30 (such as no more than about any one of 25, 20, or 15) amino acids long. In some embodiments, the first antigen binding fragment comprises an Fc region, such as an IgG1 Fc or IgG4 Fc.

In some embodiments, there is provided a multispecific (such as bispecific) antigen binding protein comprising: (a) a first antigen binding portion comprising a full-length antibody comprising two heavy chains and two light chains, wherein the full-length antibody specifically binds a first epitope, and (b) a second antigen binding portion comprising an sdAb that specifically binds a second epitope, wherein the N-terminus of the second antigen binding portion is fused to the C-terminus of one or each of the two heavy chains of the first antigen binding portion via a peptide bond or a peptide linker. In some embodiments, the sdAb is a camelid, humanized, or human sdAb. In some embodiments, the first epitope is from a first immune checkpoint molecule, and the second epitope is from a second immune checkpoint molecule. In some embodiments, the first epitope is from a first tumor antigen, and the second epitope is from a second tumor antigen. In some embodiments, the first epitope is from a tumor antigen, and the second epitope is from a cell surface molecule, such as CD3. In some embodiments, the first epitope is from a first pro-inflammatory molecule, and the second epitope is from a second pro-inflammatory molecule. In some embodiments, the first epitope is from a first angiogenic factor, and the second epitope is from a second angiogenic factor. In some embodiments, the peptide linker is no more than about 30 (such as no more than about any one of 25, 20, or 15) amino acids long. In some embodiments, the first antigen binding fragment comprises an Fc region, such as an IgG1 Fc or IgG4 Fc.

In some embodiments, there is provided a multispecific (such as bispecific) antigen binding protein comprising: (a) a first antigen binding portion comprising a full-length antibody comprising two heavy chains and two light chains, wherein the full-length antibody specifically binds a first epitope, and (b) a second antigen binding portion comprising an sdAb that specifically binds a second epitope, wherein the C-terminus of the second antigen binding portion is fused to the N-terminus of one or each of the two heavy chains of the first antigen binding portion via a peptide bond or a peptide linker. In some embodiments, the sdAb is a camelid, humanized, or human sdAb. In some embodiments, the first epitope is from a first immune checkpoint molecule, and the second epitope is from a second immune checkpoint molecule. In some embodiments, the first epitope is from a first tumor antigen, and the second epitope is from a second tumor antigen. In some embodiments, the first epitope is from a tumor antigen, and the second epitope is from a cell surface molecule, such as CD3. In some embodiments, the first epitope is from a first pro-inflammatory molecule, and the second epitope is from a second pro-inflammatory molecule. In some embodiments, the first epitope is from a first angiogenic factor, and the second epitope is from a second angiogenic factor. In some embodiments, the peptide linker is no more than about 30 (such as no more than about any one of 25, 20, or 15) amino acids long. In some embodiments, the first antigen binding fragment comprises an Fc region, such as an IgG1 Fc or IgG4 Fc.

In some embodiments, there is provided a multispecific (such as bispecific) antigen binding protein comprising: (a) a first antigen binding portion comprising a full-length antibody comprising two heavy chains and two light chains, wherein the full-length antibody specifically binds a first epitope, and (b) a second antigen binding portion comprising an sdAb that specifically binds a second epitope, wherein the N-terminus of the second antigen binding portion is fused to the C-terminus of one or each of the two light chains of the first antigen binding portion via a peptide bond or a peptide linker. In some embodiments, the sdAb is a camelid, humanized, or human sdAb. In some embodiments, the first epitope is from a first immune checkpoint molecule, and the second epitope is from a second immune checkpoint molecule. In some embodiments, the first epitope is from a first tumor antigen, and the second epitope is from a second tumor antigen. In some embodiments, the first epitope is from a tumor antigen, and the second epitope is from a cell surface molecule, such as CD3. In some embodiments, the first epitope is from a first pro-inflammatory molecule, and the second epitope is from a second pro-inflammatory molecule. In some embodiments, the first epitope is from a first angiogenic factor, and the second epitope is from a second angiogenic factor. In some embodiments, the peptide linker is no more than about 30 (such as no more than about any one of 25, 20, or 15) amino acids long. In some embodiments, the first antigen binding fragment comprises an Fc region, such as an IgG1 Fc or IgG4 Fc.

In some embodiments, there is provided a multispecific (such as bispecific) antigen binding protein comprising: (a) a first antigen binding portion comprising a full-length antibody comprising two heavy chains and two light chains, wherein the full-length antibody specifically binds a first epitope, and (b) a second antigen binding portion comprising an sdAb that specifically binds a second epitope, wherein the C-terminus of the second antigen binding portion is fused to the N-terminus of one or each of the two light chains of the first antigen binding portion via a peptide bond or a peptide linker. In some embodiments, the first epitope is from a first immune checkpoint molecule, and the second epitope is from a second immune checkpoint molecule. In some embodiments, the sdAb is a camelid, humanized, or human sdAb. In some embodiments, the first epitope is from a first tumor antigen, and the second epitope is from a second tumor antigen. In some embodiments, the first epitope is from a tumor antigen, and the second epitope is from a cell surface molecule, such as CD3. In some embodiments, the first epitope is from a first pro-inflammatory molecule, and the second epitope is from a second pro-inflammatory molecule. In some embodiments, the first epitope is from a first angiogenic factor, and the second epitope is from a second angiogenic factor. In some embodiments, the peptide linker is no more than about 30 (such as no more than about any one of 25, 20, or 15) amino acids long. In some embodiments, the first antigen binding fragment comprises an Fc region, such as an IgG1 Fc or IgG4 Fc.

The MABPs described herein may comprise one or more peptide linkers situated between the first antigen binding portion and the second antigen binding portion. In some embodiments, the peptide linker between the heavy chain polypeptide of the first antigen binding portion and the second antigen binding portion is the same as the peptide linker between the light chain polypeptide of the first antigen binding portion and the second antigen binding portion. In some embodiments, the peptide linker between the heavy chain polypeptide of the first antigen binding portion and the second antigen binding portion is different from the peptide linker between the light chain polypeptide of the first antigen binding portion and the second antigen binding portion. In some embodiments, the first antigen binding portion and the second antigen binding portion are directly fused to each other without a peptide linker disposed therebetween.

The various antigen binding portions of the MABPs may be fused to each other via a peptide linker. The peptide linkers connecting different antigen binding portions may be the same or different. Each peptide linker can be optimized individually. The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50 or more amino acids long. In some embodiments, the peptide linker is no more than about any of 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acids to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, or about 1 amino acid to about 50 amino acids.

The peptide linker may have a naturally occurring sequence, or a non-naturally occurring sequence. For example, a sequence derived from the hinge region of heavy chain only antibodies may be used as the linker. See, for example, WO1996/34103. In some embodiments, the peptide linker is a flexible linker. Exemplary flexible linkers include glycine polymers $(G)_n$, glycine-serine polymers (including, for example, $(GS)_n$ (SEQ ID NO: 9), $(GSGGS)_n$ (SEQ ID NO: 10) and $(GGGS)_n$ (SEQ ID NO: 11), where n is an integer of at least one), glycine-alanine polymers, alanine-serine polymers, and other flexible linkers known in the art. In some embodiments, the peptide linker comprises the amino acid sequence GGGGSGGGS (SEQ ID NO: 1). In some embodiments, the peptide linker comprises the hinge region of an IgG, such as the hinge region of human IgG1. In some embodiments, the peptide linker comprises the amino acid sequence EPKSCDKTHTCPPCP (SEQ ID NO: 8). In some embodiments, the peptide linker comprises a modified sequence derived from the hinge region of an IgG, such as the hinge region of human IgG1. For example, one or more cysteines in the hinge region of an IgG may be replaced with a serine. In some embodiments, the peptide linker comprises the amino acid sequence EPKSSDKTHTSPPSP (SEQ ID NO: 12).

In some embodiments, the first antigen binding portion and the second antigen binding portion are fused to each other chemically. For example, the second antigen binding portion and one or more polypeptides of the first antigen binding portion may be conjugated using one or more reactive sites via a linking group. Reactive sites in polypeptides that are useful for chemical conjugation are well known in the art, including, but not limited to primary amino groups present on amino acid residue such as the epsilon amino group of lysine, and the alpha amino group of N-terminal amino acids, thiol groups in cysteine residues, the carboxylic group of the C-terminal amino acids, and carbohydrate groups in glycosylated antibodies. In some embodiments, the reactive site is introduced into the second antigen binding portion or the first antigen binding portion by site-directed mutagenesis, incorporation of selenocysteines or unnatural amino acids, incorporation of bifunctional linkers (such as bis-alkylating reagents), and/or glycoengineering. In some embodiments, one or more primary amino groups of a polypeptide can be converted to a thiol-containing group (e.g., from a cysteine or homocysteine residue), an electrophilic unsaturated group such as a maleimide group, or halogenated group such as a bromoacetyl group, for conjugation to thiol reactive polypeptides. Any linking groups and conjugation methods known in the art can be used to chemically fuse the second antigen binding portion to the first antigen binding portion. In some embodiments, the conjugation can be achieved, for example, by using succinimide esters (such as succinimidyl 4-[N-maleimidomethyl]cyclohexane-1-carboxylate (SMCC), or N-maleimidobenzoyl-N-hydroxysuccinimide ester (MBS)), glutaraldehyde, carbodiimide (such as 1-ethyl-3-(3-dimethylaminopropyl) carbodiimide (EDCI)), benzidine (BDB), periodate, or isothiocyanate (such as N-acetyl homocysteine thiolactone (NAHT)).

Antigen Binding Portion Comprising Single-Domain Antibody

The MABPs of the present application comprise at least one antigen binding portion comprising an sdAb. Exemplary sdAbs include, but are not limited to, heavy chain variable domains from heavy-chain only antibodies (e.g., $V_HH$ or $V_{NAR}$), binding molecules naturally devoid of light chains, single domains (such as $V_H$ or $V_L$) derived from conventional 4-chain antibodies, humanized heavy-chain only antibodies, human sdAbs produced by transgenic mice or rats expressing human heavy chain segments, and engineered domains and single domain scaffolds other than those derived from antibodies. Any sdAbs known in the art or developed by the inventors may be used to construct the MABPs of the present application. The sdAbs may be derived from any species including, but not limited to mouse, rat, human, camel, llama, lamprey, fish, shark, goat, rabbit, and bovine. Single-domain antibodies contemplated herein also include naturally occurring sdAb molecules from species other than *Camelidae* and sharks.

In some embodiments, the sdAb is derived from a naturally occurring single-domain antigen binding molecule known as heavy chain antibody devoid of light chains (also referred herein as "heavy chain only antibodies"). Such single domain molecules are disclosed in WO 94/04678 and Hamers-Casterman, C. et al. (1993) *Nature* 363:446-448, for example. For clarity reasons, the variable domain derived from a heavy chain molecule naturally devoid of light chain is known herein as a $V_HH$ to distinguish it from the conventional $V_H$ of four chain immunoglobulins. Such a $V_HH$ molecule can be derived from antibodies raised in *Camelidae* species, for example, camel, llama, vicuna, dromedary, alpaca and guanaco. Other species besides *Camelidae* may produce heavy chain molecules naturally devoid of light chain, and such $V_HHs$ are within the scope of the present application.

$V_HH$ molecules from Camelids are about 10 times smaller than IgG molecules. They are single polypeptides and can be very stable, resisting extreme pH and temperature conditions. Moreover, they can be resistant to the action of proteases which is not the case for conventional antibodies. Furthermore, in vitro expression of $V_HH$ s produces high yield, properly folded functional $V_HHs$. In addition, antibodies generated in Camelids can recognize epitopes other than those recognized by antibodies generated in vitro through the use of antibody libraries or via immunization of mammals other than Camelids (see, for example, WO9749805). As such, MABPs comprising one or more $V_HH$ domains may interact more efficiently with targets than conventional antibodies. Since $V_HHs$ are known to bind into 'unusual' epitopes such as cavities or grooves, the affinity of MABPs comprising such $V_HHs$ may be more suitable for therapeutic treatment than conventional multispecific polypeptides.

In some embodiments, there is provided a multispecific (such as bispecific) antigen binding protein comprising: (a) a first antigen binding portion comprising a heavy chain variable domain ($V_H$) and a light chain variable domain ($V_L$), wherein the $V_H$ and $V_L$ together form an antigen-binding site that specifically binds a first epitope, and (b) a second antigen binding portion comprising a $V_HH$ domain that specifically binds a second epitope, wherein the first antigen binding portion and the second antigen binding portion are fused to each other. In some embodiments, the first epitope is from a first immune checkpoint molecule, and the second epitope is from a second immune checkpoint molecule. In some embodiments, the first epitope is from a first tumor antigen, and the second epitope is from a second tumor antigen. In some embodiments, the first epitope is from a tumor antigen, and the second epitope is from a cell surface molecule, such as CD3. In some embodiments, the first epitope is from a first pro-inflammatory molecule, and the second epitope is from a second pro-inflammatory molecule. In some embodiments, the first antigen binding portion comprises a heavy chain comprising the $V_H$ and a light chain comprising the $V_L$. In some embodiments, the $V_HH$ domain is humanized. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the first antigen binding portion comprises a full-length 4-chain antibody. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc or IgG4 Fc.

In some embodiments, the sdAb is derived from a variable region of the immunoglobulin found in cartilaginous fish. For example, the sdAb can be derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) *Protein Sci.* 14:2901-2909.

In some embodiments, the sdAb is recombinant, CDR-grafted, humanized, camelized, de-immunized and/or in vitro generated (e.g., selected by phage display). In some embodiments, the sdAb is a human sdAb produced by transgenic mice or rats expressing human heavy chain segments. See, e.g., US20090307787A1, U.S. Pat. No. 8,754,287, US20150289489A1, US20100122358A1, and WO2004049794. In some embodiments, the sdAb is affinity matured.

SdAbs comprising a $V_HH$ domain can be humanized to have human-like sequences. In some embodiments, the FR regions of the $V_HH$ domain used herein comprise at least about any one of 50%, 60%, 70%, 80%, 90%, 95% or more of amino acid sequence homology to human VH framework regions. One exemplary class of humanized $V_HH$ domains is characterized in that the $V_HHs$ carry an amino acid from the group consisting of glycine, alanine, valine, leucine, isoleucine, proline, phenylalanine, tyrosine, tryptophan, methionine, serine, threonine, asparagine, or glutamine at position 45, such as, for example, L45 and a tryptophan at position 103, according to the Kabat numbering. As such, polypeptides belonging to this class show a high amino acid sequence homology to human VH framework regions and said polypeptides might be administered to a human directly without expectation of an unwanted immune response therefrom, and without the burden of further humanization.

Another exemplary class of humanized *Camelidae* sdAbs has been described in WO 03/035694 and contains hydrophobic FR2 residues typically found in conventional antibodies of human origin or from other species, but compensating this loss in hydrophilicity by the charged arginine residue on position 103 that substitutes the conserved tryptophan residue present in $V_H$ from double-chain antibodies. As such, peptides belonging to these two classes show a high amino acid sequence homology to human $V_H$ framework regions and said peptides might be administered to a human directly without expectation of an unwanted immune response therefrom, and without the burden of further humanization.

In some embodiments, the MABP comprises a naturally produced sdAb or a derivative thereof, such as a Camelid sdAb, or a humanized sdAb derived from a Camelid sdAb. In some embodiments, the sdAb is obtained from llama. In some embodiments, the sdAb is further engineered to remove sequences not normally found in human antibodies (such as CDR regions or CDR-FR junctions).

In some embodiments, the MABP comprises a Fab-like domain comprising a first polypeptide chain comprising a first sdAb (such as $V_HH$) fused to a $C_H1$ domain, and a second polypeptide chain comprising a second sdAb (such as $V_HH$) fused to a $C_L$ domain. In some embodiments, the first sdAb and the second sdAb specifically bind to the same epitope. In some embodiments, the first sdAb and the second sdAb specifically bind to different epitopes. In some embodiments, each polypeptide chain of the Fab-like domain is fused to the N-terminus, C-terminus or an internal position of a polypeptide chain of the first antigen binding portion. In some embodiments, one of the two polypeptide chain of the Fab-like domain is fused to the N-terminus, C-terminus or an internal position of a polypeptide chain of the first antigen binding portion. In some embodiments, the MABP comprises two or more Fab-like domains.

In some embodiments, the MABP comprises an antigen binding portion comprising an sdAb having a suitable affinity to its epitope. For example, the affinity of the sdAb may affect the overall affinity and avidity of the MABP to the target cell or tissue, which may further affect the efficacy of the MABP. In some embodiments, the sdAb binds its epitope with high affinity. A high-affinity sdAb binds its epitope with a dissociation constant (Kd) in the low nanomolar ($10^{-9}$ M) range, such as no more than about any of 5 nM, 4 nM, 3 nM, 2 nM, 1 nM, 0.5 nM, 0.2 nM, 0.1 nM, 0.05 nM, 0.02 nM, 0.01 nM, 5 μM, 2 μM, 1 μM or less. In some embodiments, the sdAb binds its epitope with low affinity. A low-affinity sdAb binds its epitope with a Kd in the low micromolar ($10^{-6}$ M) range or higher, such as more than about any of 1 μM, 2 μM, 3 μM, 4 M, 5 μM, 6 μM, 7 μM, 8 μM, 9 μM, 10 μM or more. In some embodiments, the sdAb binds its epitope with medium affinity. A medium-affinity sdAb binds its epitope with a Kd lower than that of a low-affinity sdAb but higher than that of a high-affinity sdAb. In some embodiments, a medium-affinity sdAb binds its epitope with a Kd of any one of about 1 nM to about 10 nM, about 10 nM to about 100 nM, about 100 nM to about 500 nM, about 500 nM to about 1 μM, about 1 nM to about 100 nM, about 10 nM to about 500 nM, or about 1 nM to about 1 μM.

In some embodiments, the sdAb has a stronger affinity to its epitope than the antigen binding portion comprising $V_H$ and $V_L$. In some embodiments, the sdAb has a weaker affinity to its epitope than the antigen binding portion comprising $V_H$ and $V_L$. In some embodiments, the difference between the affinity between the sdAb to its epitope and the antigen binding portion comprising $V_H$ and $V_L$ and its epitope is about at least any of 2×, 5×, 10×, 100×, 1000× or more. In some embodiments, the affinity between the sdAb to its epitope is comparable to that between the antigen binding portion comprising $V_H$ and $V_L$ and its epitope.

In some embodiments, the sdAb specifically binds an immune checkpoint molecule. In some embodiments, the sdAb specifically binds a stimulatory immune checkpoint molecule. In some embodiments, the sdAb specifically binds an inhibitory immune checkpoint molecule. In some embodiments, the sdAb specifically binds an immune checkpoint molecule selected from the group consisting of PD-1, PD-L1, PD-L2, CTLA-4, B7-H3, TIM-3, LAG-3, VISTA, ICOS, 4-1BB, OX40, GITR, and CD40. In some embodiments, the sdAb is an agonist for the immune checkpoint molecule. In some embodiments, the sdAb is an antagonist against the immune checkpoint molecule.

Thus, in some embodiments, there is provided a multi-specific (such as bispecific) antigen binding protein comprising: (a) a first antigen binding portion comprising a heavy chain variable domain ($V_H$) and a light chain variable domain ($V_L$), wherein the $V_H$ and $V_L$ together form an antigen-binding site that specifically binds a first epitope, and (b) a second antigen binding portion comprising an sdAb that specifically binds a second epitope of an immune checkpoint molecule, wherein the first antigen binding portion and the second antigen binding portion are fused to each other. In some embodiments, the sdAb is a camelid, humanized, or human sdAb. In some embodiments, the immune checkpoint molecule is selected from the group consisting of PD-1, PD-L1, PD-L2, CTLA-4, B7-H3, TIM-3, LAG-3, VISTA, ICOS, 4-1BB, OX40, GITR, and CD40. In some embodiments, the first epitope is from a second immune checkpoint molecule. In some embodiments, the first epitope is from a pro-inflammatory molecule, such as a pro-inflammatory cytokine. In some embodiments, the pro-inflammatory molecule is selected from the group consisting of IL-1β, TNF-α, IL-5, IL-6, IL-6R and eotaxin-1. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG4 Fc.

In some embodiments, the sdAb specifically binds CTLA-4. In some embodiments, the sdAb binds CTLA-4 with high affinity. In some embodiments, the sdAb binds CTLA-4 with medium affinity. In some embodiments, the sdAb binds CTLA-4 with low affinity.

In some embodiments, there is provided a multispecific (such as bispecific) antigen binding protein comprising: (a) a first antigen binding portion comprising a heavy chain variable domain ($V_H$) and a light chain variable domain ($V_L$), wherein the $V_H$ and $V_L$ together form an antigen-binding site that specifically binds an epitope of an immune checkpoint molecule, and (b) a second antigen binding portion comprising an sdAb (e.g., a $V_H$H) that specifically binds CTLA-4, wherein the first antigen binding portion and the second antigen binding portion are fused to each other. In some embodiments, the sdAb is a camelid, humanized, or human sdAb. In some embodiments, the immune checkpoint molecule is an epitope of CTLA-4 that is different from the epitope specifically recognized by the sdAb. In some embodiments, the immune checkpoint molecule is selected from the group consisting of PD-1, PD-L1, PD-L2, B7-H3, TIM-3, LAG-3, VISTA, ICOS, 4-1BB, OX40, GITR, and CD40. In some embodiments, the first antigen binding portion comprises a full-length anti-PD-1 monoclonal antibody (such as pembrolizumab or nivolumab) or antigen binding fragment thereof. In some embodiments, the first antigen binding portion comprises a full-length anti-PD-L1 monoclonal antibody (such as duravalumab or atezolizumab) or antigen binding fragment thereof. In some embodiments, the sdAb binds CTLA-4 with high affinity. In some embodiments, the sdAb binds CTLA-4 with medium affinity. In some embodiments, the sdAb binds CTLA-4 with low affinity. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG4 Fc.

In some embodiments, the sdAb specifically binds TIM-3. In some embodiments, the sdAb binds TIM-3 with high affinity. In some embodiments, the sdAb binds TIM-3 with medium affinity. In some embodiments, the sdAb binds TIM-3 with low affinity.

Thus, in some embodiments, there is provided a multi-specific (such as bispecific) antigen binding protein comprising: (a) a first antigen binding portion comprising a heavy chain variable domain ($V_H$) and a light chain variable domain ($V_L$), wherein the $V_H$ and $V_L$ together form an antigen-binding site that specifically binds an epitope of an immune checkpoint molecule, and (b) a second antigen binding portion comprising an sdAb (e.g., a $V_H H$) that specifically binds TIM-3, wherein the first antigen binding portion and the second antigen binding portion are fused to each other. In some embodiments, the sdAb is a camelid, humanized, or human sdAb. In some embodiments, the immune checkpoint molecule is selected from the group consisting of CTLA-4, PD-1, PD-L1, PD-L2, B7-H3, LAG-3, VISTA, ICOS, 4-1BB, OX40, GITR, and CD40. In some embodiments, the first antigen binding portion comprises a full-length anti-PD-1 monoclonal antibody (such as pembrolizumab or nivolumab) or antigen binding fragment thereof. In some embodiments, the first antigen binding portion comprises a full-length anti-PD-L1 monoclonal antibody (such as duravalumab or atezolizumab) or antigen binding fragment thereof. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG4 Fc.

In some embodiments, the sdAb specifically binds LAG-3. In some embodiments, the sdAb binds LAG-3 with high affinity. In some embodiments, the sdAb binds LAG-3 with medium affinity. In some embodiments, the sdAb binds LAG-3 with low affinity.

Thus, in some embodiments, there is provided a multi-specific (such as bispecific) antigen binding protein comprising: (a) a first antigen binding portion comprising a heavy chain variable domain ($V_H$) and a light chain variable domain ($V_L$), wherein the $V_H$ and $V_L$ together form an antigen-binding site that specifically binds an epitope of an immune checkpoint molecule, and (b) a second antigen binding portion comprising an sdAb (e.g., a $V_H H$) that specifically binds LAG-3, wherein the first antigen binding portion and the second antigen binding portion are fused to each other. In some embodiments, the sdAb is a camelid, humanized, or human sdAb. In some embodiments, the immune checkpoint molecule is selected from the group consisting of CTLA-4, PD-1, PD-L1, PD-L2, B7-H3, TIM-3, VISTA, ICOS, 4-1BB, OX40, GITR, and CD40. In some embodiments, the first antigen binding portion comprises a full-length anti-PD-1 monoclonal antibody (such as pembrolizumab or nivolumab) or antigen binding fragment thereof. In some embodiments, the first antigen binding portion comprises a full-length anti-PD-L1 monoclonal antibody (such as duravalumab or atezolizumab) or antigen binding fragment thereof. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG4 Fc.

In some embodiments, the sdAb specifically binds VISTA. In some embodiments, the sdAb binds VISTA with high affinity. In some embodiments, the sdAb binds VISTA with medium affinity. In some embodiments, the sdAb binds VISTA with low affinity.

Thus, in some embodiments, there is provided a multi-specific (such as bispecific) antigen binding protein comprising: (a) a first antigen binding portion comprising a heavy chain variable domain ($V_H$) and a light chain variable domain ($V_L$), wherein the $V_H$ and $V_L$ together form an antigen-binding site that specifically binds an epitope of an immune checkpoint molecule, and (b) a second antigen binding portion comprising an sdAb (e.g., a $V_H H$) that specifically binds VISTA, wherein the first antigen binding portion and the second antigen binding portion are fused to each other. In some embodiments, the sdAb is a camelid, humanized, or human sdAb. In some embodiments, the immune checkpoint molecule is selected from the group consisting of CTLA-4, PD-1, PD-L1, PD-L2, B7-H3, TIM-3, LAG-3, ICOS, 4-1BB, OX40, GITR, and CD40. In some embodiments, the first antigen binding portion comprises a full-length anti-PD-1 monoclonal antibody (such as pembrolizumab or nivolumab) or antigen binding fragment thereof. In some embodiments, the first antigen binding portion comprises a full-length anti-PD-L1 monoclonal antibody (such as duravalumab or atezolizumab) or antigen binding fragment thereof. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG4 Fc.

In some embodiments, the sdAb specifically binds a cell surface antigen. In some embodiments, the cell surface antigen is a tumor antigen. In some embodiments, the sdAb specifically binds a cell surface antigen on an immune effector cell, such as T cell, or Natural Killer cell.

In some embodiments, there is provided a multispecific (such as bispecific) antigen binding protein comprising: (a) a first antigen binding portion comprising a heavy chain variable domain ($V_H$) and a light chain variable domain ($V_L$), wherein the $V_H$ and $V_L$ together form an antigen-binding site that specifically binds a first tumor antigen, and (b) a second antigen binding portion comprising an sdAb that specifically binds a second tumor antigen, wherein the first antigen binding portion and the second antigen binding portion are fused to each other. In some embodiments, the sdAb is a camelid, humanized, or human sdAb. In some embodiments, the first tumor antigen and/or the second tumor antigen is selected from the group consisting of HER2, BRAF, EGFR, VEGFR2, CD20, RANKL, CD38, and CD52. In some embodiments, the first antigen binding portion comprises a full-length anti-HER-2 monoclonal antibody (such as trastuzumab) or antigen binding fragment thereof. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc.

In some embodiments, the sdAb specifically binds CD3. In some embodiments, the sdAb binds CD3 with high affinity. In some embodiments, the sdAb binds CD3 with medium affinity. In some embodiments, the sdAb binds CD3 with low affinity.

Thus, in some embodiments, there is provided a multispecific (such as bispecific) antigen binding protein comprising: (a) a first antigen binding portion comprising a heavy chain variable domain ($V_H$) and a light chain variable domain ($V_L$), wherein the $V_H$ and $V_L$ together form an antigen-binding site that specifically binds an epitope of a tumor antigen, and (b) a second antigen binding portion comprising an sdAb (e.g., a $V_HH$) that specifically binds CD3, wherein the first antigen binding portion and the second antigen binding portion are fused to each other. In some embodiments, the sdAb is a camelid, humanized, or human sdAb. In some embodiments, the tumor antigen is selected from the group consisting of HER2, BRAF, EGFR, VEGFR2, CD20, RANKL, CD38, and CD52. In some embodiments, the first antigen binding portion comprises a full-length anti-HER-2 monoclonal antibody (such as trastuzumab) or antigen binding fragment thereof. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG4 Fc.

In some embodiments, the sdAb specifically binds an extracellular protein, such as a secreted protein. In some embodiments, the sdAb specifically binds a pro-inflammatory molecule. In some embodiments, the sdAb specifically binds an angiogenic factor, such as VEGF.

In some embodiments, the sdAb specifically binds IL-1β. In some embodiments, the sdAb binds IL-1β with high affinity. In some embodiments, the sdAb binds IL-1β with medium affinity. In some embodiments, the sdAb binds IL-1β with low affinity.

Thus, in some embodiments, there is provided a multispecific (such as bispecific) antigen binding protein comprising: (a) a first antigen binding portion comprising a heavy chain variable domain ($V_H$) and a light chain variable domain ($V_L$), wherein the $V_H$ and $V_L$ together form an antigen-binding site that specifically binds an epitope of a pro-inflammatory molecule, and (b) a second antigen binding portion comprising an sdAb (e.g., a $V_HH$) that specifically binds IL-1β, wherein the first antigen binding portion and the second antigen binding portion are fused to each other. In some embodiments, the sdAb is a camelid, humanized, or human sdAb. In some embodiments, the pro-inflammatory molecule is selected from the group consisting of TNF-α, IL-5, IL-6, IL-6R and eotaxin-1. In some embodiments, the first antigen binding portion comprises a full-length anti-TNF-α monoclonal antibody (such as adalimumab) or antigen binding fragment thereof. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc.

In some embodiments, the sdAb specifically binds eotaxin-1, i.e., CCL11.

Thus, in some embodiments, there is provided a multispecific (such as bispecific) antigen binding protein comprising: (a) a first antigen binding portion comprising a heavy chain variable domain ($V_H$) and a light chain variable domain ($V_L$), wherein the $V_H$ and $V_L$ together form an antigen-binding site that specifically binds an epitope of a pro-inflammatory molecule, and (b) a second antigen binding portion comprising an sdAb (e.g., a $V_HH$) that specifically binds eotaxin-1, wherein the first antigen binding portion and the second antigen binding portion are fused to each other. In some embodiments, the sdAb is a camelid, humanized, or human sdAb. In some embodiments, the pro-inflammatory molecule is selected from the group consisting of IL-1β, TNF-α, IL-5, IL-6 and IL-6R. In some embodiments, the first antigen binding portion comprises a full-length anti-IL-5 monoclonal antibody (such as mepolizumab) or antigen binding fragment thereof. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc.

Antigen Binding Portion Comprising $V_H$ and $V_L$

The MABPs of the present application comprise at least one antigen binding portion comprising a heavy chain variable domain ($V_H$) and a light chain variable domain ($V_L$). Such antigen binding portion can be a full-length conventional antibody consisting of two heavy chains and two light chains, or an antigen binding fragment derived therefrom.

In some embodiments, the first antigen binding portion is an antigen binding fragment comprising a heavy chain comprising the $V_H$ domain and a light chain comprising the $V_L$ domain. Exemplary antigen binding fragments contemplated herein include, but are not limited to, Fab, Fab', F(ab')$_2$, and Fv fragments; diabodies; linear antibodies; single-chain antibody molecules (such as scFv); and multi-specific antibodies formed from antibody fragments.

In some embodiments, the first antigen binding portion comprises an Fc region, such as a human Fc region. In some embodiments, the Fc region is derived from an IgG molecule, such as any one of the IgG1, IgG2, IgG3, or IgG4 subclass. In some embodiments, the Fc region is capable of mediating an antibody effector function, such as ADCC (antibody-dependent cell-mediated cytotoxicity) and/or CDC (complement-dependent cytotoxicity). For example, antibodies of subclass IgG1, IgG2, and IgG3 with wildtype Fc sequences usually show complement activation including C1q and C3 binding, whereas IgG4 does not activate the complement system and does not bind C1q and/or C3. In some embodiments, the Fc region comprises a modification that reduces binding affinity of the Fc region to an Fc receptor. In some embodiments, the Fc region is an IgG1 Fc. In some embodiments, the IgG1 Fc comprises one or mutations in positions 233-236, such as L234A and/or L235A. In some embodiments, the Fc region is an IgG4 Fc. In some embodiments, the IgG4 Fc comprises a mutation in positions 327, 330 and/or 331. See, for example, Armour K L et al., *Eur J. Immunol.* 1999; 29: 2613; and Shields R L et al., J. Biol. Chem. 2001; 276: 6591. In some embodiments, the Fc region comprises a P329G mutation.

In some embodiments, the Fc region comprises a modification that promotes heterodimerization of two non-identical heavy chains. Such modified Fc regions may be of particular interest for MABPs described herein having an asymmetric design. In some embodiments, said modification is a knob-into-hole modification, comprising a knob modification in one of the heavy chains or heavy chain fusion polypeptides and a hole modification in the other one of the two heavy chains or heavy chain fusion polypeptides. In one embodiment, the Fc region comprises a modification within the interface between the two heavy chains in the CH3 domain, wherein i) in the CH3 domain of one heavy chain, an amino acid residue is replaced with an amino acid residue having a larger side chain volume, thereby generating a protuberance ("knob") within the interface in the CH3 domain of one heavy chain which is positionable in a cavity ("hole") within the interface in the CH3 domain of the other heavy chain, and ii) in the CH3 domain of the other heavy chain, an amino acid residue is replaced with an amino acid residue having a smaller side chain volume, thereby generating a cavity ("hole") within the interface in the second CH3 domain within which a protuberance ("knob") within the interface in the first CH3 domain is positionable. Examples of knob-into-hole modifications have been described, for example, in US 2011/0287009, US2007/0178552, WO 96/027011, WO 98/050431, and Zhu et al., 1997, *Protein Science* 6:781-788. Other modifications to the Fc region that promote heterodimerization are also contemplated herein. For example, electrostatic steering effects can be engineered into the Fc region to provide Fc-heterodimeric molecules (see, e.g., U.S. Pat. No. 4,676,980, and Brennan et al., *Science*, 229: 81 (1985)).

In some embodiments, the Fc region comprises a modification that inhibits Fab arm exchange. For example, the S228P mutation in IgG4 Fc prevents Fab arm exchange.

In some embodiments, the first antigen binding portion comprises a kappa light chain constant region. In some embodiments, the first antigen binding portion comprises a lambda light chain constant region. In some embodiments, the first antigen binding portion comprises a light chain constant region comprising the amino acid sequence of SEQ ID NO: 6.

In some embodiments, the first antigen binding portion comprises a heavy chain constant region comprising the amino acid sequence of SEQ ID NO: 7.

In some embodiments, the first antigen binding portion is a full-length antibody consisting of two heavy chains and two light chains. In some embodiments, the first antigen binding portion comprises a monoclonal antibody consisting of two heavy chains and two light chains (also referred herein as "4-chain antibody"). In some embodiments, the first antigen binding portion comprises a multispecific (such as bispecific) full-length antibody consisting of two heavy chains and two light chains. In some embodiments, the first antigen binding portion comprises a full-length antibody of human IgG1 subclass, or of human IgG1 subclass with the mutations L234A and L235A. In some embodiments, the first antigen binding portion comprises a full-length antibody of human IgG2 subclass. In some embodiments, the first antigen binding portion comprises a full-length antibody of human IgG3 subclass. In some embodiments, the first antigen binding portion comprises a full-length antibody of human IgG4 subclass or, of human IgG4 subclass with the additional mutation S228P.

Any full-length 4-chain antibody known in the art or antigen binding fragments derived therefrom can be used as the first antigen binding portion in the MABP of the present application. Antibodies or antibody fragments with proven clinical efficacy, safety, and pharmacokinetics profile are of particular interest. In some embodiments, the antibody or antibody fragment known in the art is further engineered, such as humanized or mutagenized to select for a variant with a suitable affinity, prior to fusion with the second antigen binding portion to provide the MABP. In some embodiments, the first antigen binding portion comprises the V_H and V_L domains of a monoclonal antibody or antibody fragment known in the art, and modified heavy chain constant region and/or light chain constant region. In some embodiments, the first antigen binding portion comprises the monoclonal antibody known in the art and a modified Fc region, such as an IgG4 Fc with an S228P mutation. In some embodiments, the first antigen binding portion comprises a human, humanized, or chimeric full-length antibody or antibody fragments.

In some embodiments, the first antigen binding portion is derived from an approved (such as by FDA and/or EMA) or investigational monoclonal antibody or antibody fragment (such as Fab). In some embodiments, the first antigen binding portion is an approved (such as by FDA and/or EMA) or investigational monoclonal antibody or antibody fragment (such as Fab).

In some embodiments, the first antigen binding portion specifically binds an immune checkpoint molecule. In some embodiments, the first antigen binding portion comprises a full-length antibody (such as antagonist antibody) or antigen binding fragment derived therefrom that specifically binds an inhibitory immune checkpoint protein. In some embodiments, the first antigen binding portion comprises a full-length antibody (such as agonist antibody) or antigen binding fragment derived therefrom that specifically binds a stimulatory checkpoint molecule. In some embodiments, the immune checkpoint molecule is selected from the group consisting of PD-1, PD-L1, PD-L2, CTLA-4, B7-H3, TIM-3, LAG-3, VISTA, ICOS, 4-1BB, OX40, GITR, and CD40. In some embodiments, the first antigen binding portion is an anti-PD-1 antibody or antigen binding fragment thereof. In some embodiments, the anti-PD-1 antibody is selected from the group consisting of pembrolizumab and nivolumab. In some embodiments, the first antigen binding portion is an anti-PD-L1 antibody or antigen binding fragment thereof. In some embodiments, the anti-PD-L1 antibody is duravalumab or atezolizumab. In some embodiments, the first antigen binding portion is an anti-CTLA-4 antibody or antigen binding fragment thereof. In some embodiments, the anti-CTLA-4 antibody is ipilimumab.

In some embodiments, the first antigen binding portion comprises pembrolizumab or antigen binding fragment thereof. In some embodiments, the first antigen binding portion comprises a $V_H$ domain comprising the amino acid sequence of SEQ ID NO: 2 and a $V_L$ domain comprising the amino acid sequence of SEQ ID NO: 3. In some embodiments, the first antigen binding portion comprises an IgG4 Fc. In some embodiments, the first antigen binding portion comprises a heavy chain comprising the amino acid sequence of SEQ ID NO: 4. In some embodiments, the first antigen binding portion comprises a light chain comprising the amino acid sequence of SEQ ID NO: 5. In some embodiments, the first antigen binding portion comprises an IgG4 Fc.

Pembrolizumab (e.g., KEYTRUDA®) is a humanized antibody used in cancer immunotherapy. It targets the programmed cell death 1 (PD-1) receptor. The drug was initially used in treating metastatic melanoma. On Sep. 4, 2014 the US Food and Drug Administration (FDA) approved KEYTRUDA® under the FDA Fast Track Development Program. It is approved for use in advanced melanoma. On Oct. 2, 2015, the US FDA approved KEYTRUDA® for the treatment of metastatic non-small cell lung cancer in patients whose tumors express PD-L1 and who have failed treatments with other chemotherapeutic agents.

Ipilimumab (e.g., YERVOY®) is a fully human anti-CTLA-4 immunoglobulin G1 (IgG1) monoclonal antibody (mAb) that blocks the down-regulation of T-cell activation. Ipilimumab is a CTLA-4 immune checkpoint inhibitor that blocks T-cell inhibitory signals induced by the CTLA-4 pathway, and increases the number of tumor reactive T effector cells. Ipilimumab was used in combination with nivolumab (e.g., OPDIVO®) to investigate the effects of concurrent inhibition of the PD-1 and CTLA-4 receptors in nonhuman primates. OPDIVO® has demonstrated clinical efficacy either as monotherapy or in combination with ipilimumab in treating several tumor types, including renal cell carcinoma, melanoma, NSCLC, and some lymphomas. BMS recently announced the treatment results of immune combination therapy OPDIVO® and ipilimumab for treating melanoma. Compared with ipilimumab monotherapy, the combined therapy achieved a very high objective response rate (61% vs 11%) and complete remission rate of 22%, while disease progression or death risk decreased by 60%. This kind of therapy demonstrated the great potential of different combinations of immune therapeutic agents in clinical treatment of cancer.

In some embodiments, the first antigen binding portion specifically binds a tumor antigen. In some embodiments, the tumor antigen is selected from the group consisting of HER2, BRAF, EGFR, VEGFR2, CD20, RANKL, CD38, and CD52. In some embodiments, the first antigen binding portion is an anti-HER2 antibody or antigen binding fragment thereof. In some embodiments, the anti-HER2 antibody is trastuzumab.

Trastuzumab (HERCEPTIN®), one of the five top selling therapeutic antibodies, is a humanized anti-HER2 receptor monoclonal antibody that has significantly increased the survival rate in patients with HER2-positive breast cancer. The HER receptors are proteins that are embedded in the cell membrane and communicate molecular signals from outside the cell (molecules called EGFs) to inside the cell, and turn genes on and off. The HER protein, Human Epidermal Growth Factor Receptor, binds Human Epidermal Growth Factor, and stimulates cell proliferation. In some cancers, notably certain types of breast cancer, HER2 is over-expressed, and causes cancer cells to reproduce uncontrollably. However, among breast cancer patients, only 15-20% of them exhibit amplification and overexpression of the human epidermal growth factor receptor 2 (HER2), most HER2- patients do not respond to trastuzumab. In addition, some of the HER2+ patients have developed resistance to trastuzumab after initial treatment. As the epidermal growth factor RTK family consists of four members: EGFR, HER2, HER3 and HER4, some bispecific antibodies have been developed to target two of these antigens, which have shown advantages over conventional monospecific antibodies.

In some embodiments, the first antigen binding portion specifically binds an angiogenic factor. In some embodiments, the first antigen binding portion is an anti-Ang2 antibody or antigen binding fragment thereof, such as LC10.

In some embodiments, the first antigen binding portion specifically binds a pro-inflammatory molecule. In some embodiments, the pro-inflammatory molecule is selected from the group consisting of IL-1β, TNF-α, IL-5, IL-6, IL-6R and eotaxin-1. In some embodiments, the first antigen binding portion is an anti-TNF-α antibody or antigen binding fragment thereof. In some embodiments, the anti-TNF-α antibody is adalimumab.

Exemplary Multispecific Antigen Binding Proteins

In some embodiments, there is provided a multispecific (such as bispecific) antigen binding protein comprising: (a) a first antigen binding portion comprising a full-length antibody (such as pembrolizumab or nivolumab) consisting of two heavy chains and two light chains, wherein the full-length antibody specifically binds PD-1; and (b) a second antigen binding portion comprising an sdAb that specifically binds CTLA-4, wherein the first antigen binding portion and the second antigen binding portion are fused to each other. In some embodiments, the sdAb is a camelid, humanized, or human sdAb. In some embodiments, the sdAb binds CTLA-4 with a high affinity. In some embodiments, the sdAb binds CTLA-4 with a medium affinity. In some embodiments, the sdAb binds CTLA-4 with a low affinity. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the peptide linker comprises the amino acid sequence of SEQ ID NO: 1, 8 or 13. In some embodiments, the first antigen binding fragment comprises an Fc region, such as an IgG4 Fc.

Figure 4:
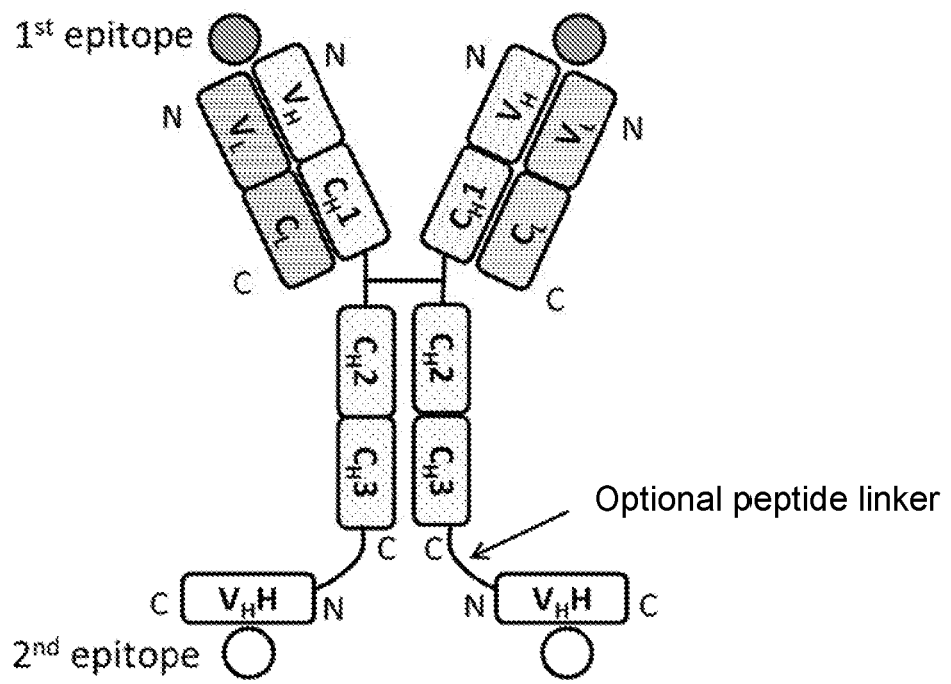
FIG. 4 depicts a schematic structure of an exemplary BABP comprising a monospecific full-length antibody having two identical heavy chains and two identical light chains, and two identical sdAbs, wherein the N-terminus of each sdAb is fused to the C terminus of one heavy chain via an optional peptide linker. The full-length antibody has two antigen binding sites that specifically bind a first epitope. The two sdAbs specifically bind the second epitope. For example, the BABP can consist of four polypeptide chains with structures from the N-terminus to the C-terminus as follows: (1) $V_L$-$C_L$; (2) $V_H$-$C_H1$-$C_H2$-$C_H3$-$V_HH$; (3) $V_H$-$C_H1$-$C_H2$-$C_H3$-$V_HH$; and (4) $V_L$-$C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, and each $V_HH$ specifically binds a copy of the second epitope. In alternative formats, each sdAb may be replaced with two copies of the sdAb fused to each other.

In some embodiments, there is provided a bispecific antigen binding protein comprising: (a) a first polypeptide comprising from N-terminus to C-terminus: $V_H$—$C_H1$-$C_H2$-$C_H3$-$V_HH$; and (b) a second polypeptide comprising from N-terminus to C-terminus: VL-CL, wherein $V_H$ and $V_L$ forms an antigen binding site that specifically binds PD-1, and wherein $V_HH$ specifically binds CTLA-4. In some embodiments, the $V_H$ and $V_L$ domains are derived from pembrolizumab or nivolumab. In some embodiments, the $C_H3$ and $V_HH$ domains are fused to each other via a peptide linker, such as a peptide linker comprising the amino acid sequence of SEQ ID NO: 1, 8 or 13. In some embodiments, the $C_H2$ and $C_H3$ domains are derived from an IgG4 Fc. In some embodiments, the BABP has the structure as shown in FIG. 4.

In some embodiments, there is provided a bispecific antigen binding protein comprising: (a) a first polypeptide comprising from N-terminus to C-terminus: $V_HH$-$V_H$-$C_H1$-$C_H2$-$C_H3$; and (b) a second polypeptide comprising from N-terminus to C-terminus: VL-CL, wherein $V_H$ and $V_L$ forms an antigen binding site that specifically binds PD-1, and wherein $V_HH$ specifically binds CTLA-4. In some embodiments, the $V_H$ and $V_L$ domains are derived from pembrolizumab or nivolumab. In some embodiments, the $V_H$ and $V_HH$ domains are fused to each other via a peptide linker, such as a peptide linker comprising the amino acid sequence of SEQ ID NO: 1, 8 or 13. In some embodiments, the $C_H2$ and $C_H3$ domains are derived from an IgG4 Fc. In some embodiments, the BABP has the structure as shown in FIG. 9.

In some embodiments, there is provided a bispecific antigen binding protein comprising: (a) a first polypeptide comprising from N-terminus to C-terminus: $V_H$—$C_H1$-$C_H2$-$C_H3$; and (b) a second polypeptide comprising from N-terminus to C-terminus: VL-CL-$V_HH$, wherein $V_H$ and $V_L$ forms an antigen binding site that specifically binds PD-1, and wherein $V_HH$ specifically binds CTLA-4. In some embodiments, the $V_H$ and $V_L$ domains are derived from pembrolizumab or nivolumab. In some embodiments, the $C_L$ and $V_HH$ domains are fused to each other via a peptide linker, such as a peptide linker comprising the amino acid sequence of SEQ ID NO: 1, 8 or 13. In some embodiments, the $C_H2$ and $C_H3$ domains are derived from an IgG4 Fc. In some embodiments, the BABP has the structure as shown in FIG. 11.

In some embodiments, there is provided a bispecific antigen binding protein comprising: (a) a first polypeptide comprising from N-terminus to C-terminus: $V_H$—$C_H1$-$C_H2$-$C_H3$; and (b) a second polypeptide comprising from N-terminus to C-terminus: $V_HH$-VL-CL, wherein $V_H$ and $V_L$ forms an antigen binding site that specifically binds PD-1, and wherein $V_HH$ specifically binds CTLA-4. In some embodiments, the $V_H$ and $V_L$ domains are derived from pembrolizumab or nivolumab. In some embodiments, the $V_L$ and $V_HH$ domains are fused to each other via a peptide linker, such as a peptide linker comprising the amino acid sequence of SEQ ID NO: 1, 8 or 13. In some embodiments, the $C_H2$ and $C_H3$ domains are derived from an IgG4 Fc. In some embodiments, the BABP has the structure as shown in FIG. 13.

In some embodiments, there is provided a bispecific antigen binding protein comprising: (a) a first polypeptide comprising from N-terminus to C-terminus: $V_HH$-$V_H$-$C_H1$-$C_H2$-$C_H3$; and (b) a second polypeptide comprising from N-terminus to C-terminus: $V_HH$-VL-CL, wherein $V_H$ and $V_L$ forms an antigen binding site that specifically binds PD-1, and wherein $V_HH$ specifically binds CTLA-4. In some embodiments, the $V_H$ and $V_L$ domains are derived from pembrolizumab or nivolumab. In some embodiments, the $V_L$ and $V_HH$ domains, and/or the $V_L$ and $V_HH$ domains are fused to each other via a peptide linker, such as a peptide linker comprising the amino acid sequence of SEQ ID NO: 1, 8 or 13. In some embodiments, the $C_H2$ and $C_H3$ domains are derived from an IgG4 Fc. In some embodiments, the BABP has the structure as shown in FIG. 17.

In some embodiments, there is provided a bispecific antigen binding protein comprising: (a) a first polypeptide comprising from N-terminus to C-terminus: $V_HH1$-$V_HH2$-$V_H$-$C_H1$-$C_H2$-$C_H3$; and (b) a second polypeptide comprising from N-terminus to C-terminus: VL-CL, wherein $V_H$ and $V_L$ forms an antigen binding site that specifically binds PD-1, and wherein $V_HH$ specifically binds CTLA-4. In some embodiments, the $V_H$ and $V_L$ domains are derived from pembrolizumab or nivolumab. In some embodiments, the $V_HH1$ and $V_HH2$ domains, and/or the $V_H$ and $V_HH2$ domains are fused to each other via a peptide linker, such as a peptide linker comprising the amino acid sequence of SEQ ID NO: 1, 8 or 13. In some embodiments, the $C_H2$ and $C_H3$ domains are derived from an IgG4 Fc. In some embodiments, the BABP has the structure as shown in FIG. 18.

In some embodiments, there is provided a bispecific antigen binding protein comprising: (a) a first polypeptide comprising from N-terminus to C-terminus: $V_H$—$C_H1$-$V_HH$-$C_H2$-$C_H3$; and (b) a second polypeptide comprising from N-terminus to C-terminus: VL-CL, wherein $V_H$ and $V_L$ forms an antigen binding site that specifically binds PD-1, and wherein $V_HH$ specifically binds CTLA-4. In some embodiments, the $V_H$ and $V_L$ domains are derived from pembrolizumab or nivolumab. In some embodiments, the $C_H1$ and $V_HH$ domains are fused to each other via a peptide linker, such as a peptide linker comprising the amino acid sequence of SEQ ID NO: 1, 8 or 13. In some embodiments, the $C_H2$ and $C_H3$ domains are derived from an IgG4 Fc. In some embodiments, the BABP has the structure as shown in FIG. 19.

In some embodiments, there is provided a bispecific antigen binding protein comprising a polypeptide comprising from N-terminus to C-terminus: scFv-$V_HH$-$C_H2$-$C_H3$, wherein the scFv that specifically binds PD-1, and wherein $V_HH$ specifically binds CTLA-4. In some embodiments, the scFv derived from pembrolizumab or nivolumab. In some embodiments, the scFv and $V_HH$ domains are fused to each other via a peptide linker, such as a peptide linker comprising the amino acid sequence of SEQ ID NO: 1, 8 or 13. In some embodiments, the $C_H2$ and $C_H3$ domains are derived from an IgG4 Fc. In some embodiments, the BABP has the structure as shown in FIG. 20.

In some embodiments, there is provided a bispecific antigen binding protein comprising: (a) a first polypeptide comprising from N-terminus to C-terminus: $V_H$—$C_H1$-$V_HH$-$C_H1$-$C_H2$-$C_H3$; and (b) a second polypeptide comprising from N-terminus to C-terminus: $V_L$—$C_L$-$V_HH$-$C_L$, wherein $V_H$ and $V_L$ forms an antigen binding site that specifically binds PD-1, and wherein $V_HH$ specifically binds CTLA-4. In some embodiments, the $V_H$ and $V_L$ domains are derived from pembrolizumab or nivolumab. In some embodiments, the $C_H1$ and $V_HH$ domains, and/or $C_L$ and $V_HH$ domains are fused to each other via a peptide linker, such as a peptide linker comprising the amino acid sequence of SEQ ID NO: 1, 8 or 13. In some embodiments, the $C_H2$ and $C_H3$ domains are derived from an IgG4 Fc. In some embodiments, the BABP has the structure as shown in FIG. 21.

In some embodiments, there is provided a bispecific antigen binding protein comprising: (a) a first polypeptide comprising from N-terminus to C-terminus: scFv-$V_HH$-$C_H2$-$C_H3$; and (b) a second polypeptide comprising from N-terminus to C-terminus: $V_HH$-$C_L$, wherein the scFv specifically binds PD-1, and wherein $V_HH$ specifically binds CTLA-4. In some embodiments, the scFv is derived from pembrolizumab or nivolumab. In some embodiments, the scFv and $V_HH$ domains are fused to each other via a peptide linker, such as a peptide linker comprising the amino acid sequence of SEQ ID NO: 1, 8 or 13. In some embodiments, the $C_H2$ and $C_H3$ domains are derived from an IgG4 Fc. In some embodiments, the BABP has the structure as shown in FIG. 22.

In some embodiments, there is provided a multispecific (such as bispecific) antigen binding protein comprising: (a) a first antigen binding portion comprising a full-length antibody (such as pembrolizumab or nivolumab) consisting of two heavy chains and two light chains, wherein the full-length antibody specifically binds PD-1; and (b) a second antigen binding portion comprising an sdAb that specifically binds TIM-3, wherein the first antigen binding portion and the second antigen binding portion are fused to each other. In some embodiments, the sdAb is a camelid, humanized, or human sdAb. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the peptide linker comprises the amino acid sequence of SEQ ID NO: 1, 8 or 13. In some embodiments, the first antigen binding fragment comprises an Fc region, such as an IgG4 Fc.

In some embodiments, there is provided a multispecific (such as bispecific) antigen binding protein comprising: (a) a first antigen binding portion comprising a full-length antibody (such as pembrolizumab or nivolumab) consisting of two heavy chains and two light chains, wherein the full-length antibody specifically binds PD-1; and (b) a second antigen binding portion comprising an sdAb that specifically binds LAG-3, wherein the first antigen binding portion and the second antigen binding portion are fused to each other. In some embodiments, the sdAb is a camelid, humanized, or human sdAb. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the peptide linker comprises the amino acid sequence of SEQ ID NO: 1, 8 or 13. In some embodiments, the first antigen binding fragment comprises an Fc region, such as an IgG4 Fc.

In some embodiments, there is provided a multispecific (such as bispecific) antigen binding protein comprising: (a) a first antigen binding portion comprising a full-length antibody (such as pembrolizumab or nivolumab) consisting of two heavy chains and two light chains, wherein the full-length antibody specifically binds PD-1; and (b) a second antigen binding portion comprising an sdAb that specifically binds VISTA, wherein the first antigen binding portion and the second antigen binding portion are fused to each other. In some embodiments, the sdAb is a camelid, humanized, or human sdAb. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the peptide linker comprises the amino acid sequence of SEQ ID NO: 1, 8 or 13. In some embodiments, the first antigen binding fragment comprises an Fc region, such as an IgG4 Fc.

In some embodiments, there is provided a multispecific (such as bispecific) antigen binding protein comprising: (a) a first antigen binding portion comprising a heavy chain comprising a $V_H$ domain comprising the amino acid sequence of SEQ ID NO: 2 and a light chain comprising a $V_L$ domain comprising the amino acid sequence of SEQ ID NO: 3; and (b) a second antigen binding portion comprising an anti-CTLA-4 sdAb, and wherein the first antigen binding portion and the second antigen binding portion are fused to each other. In some embodiments, the sdAb is a camelid, humanized, or human sdAb. In some embodiments, the first antigen binding portion is full-length pembrolizumab. In some embodiments, the N-terminus of the second antigen binding portion is fused to the C-terminus of the heavy chain of the first antigen binding portion via an optional peptide linker. In some embodiments, the C-terminus of the second antigen binding portion is fused to the N-terminus of the heavy chain of the first antigen binding portion via an optional peptide linker. In some embodiments, the peptide linker is no more than about 30 (such as no more than about any one of 25, 20, or 15) amino acids long. In some embodiments, the peptide linker comprises the amino acid sequence of SEQ ID NO: 1, 8 or 13. In some embodiments, the first antigen binding fragment comprises an Fc region, such as an IgG4 Fc.

In some embodiments, there is provided a multispecific (such as bispecific) antigen binding protein comprising: (a) a first antigen binding portion comprising a full-length antibody (such as duravalumab or atezolizumab) consisting of two heavy chains and two light chains, wherein the full-length antibody specifically binds PD-L1; and (b) a second antigen binding portion comprising an sdAb that specifically binds CTLA-4, wherein the first antigen binding portion and the second antigen binding portion are fused to each other. In some embodiments, the sdAb is a camelid, humanized, or human sdAb. In some embodiments, the sdAb binds CTLA-4 with a high affinity. In some embodiments, the sdAb binds CTLA-4 with a medium affinity. In some embodiments, the sdAb binds CTLA-4 with a low affinity. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the peptide linker comprises the amino acid sequence of SEQ ID NO: 1, 8 or 13. In some embodiments, the first antigen binding fragment comprises an Fc region, such as an IgG4 Fc.

In some embodiments, there is provided a bispecific antigen binding protein comprising: (a) a first polypeptide comprising from N-terminus to C-terminus: $V_HH$-$V_H$-$C_H1$-$C_H2$-$C_H3$; and (b) a second polypeptide comprising from N-terminus to C-terminus: VL-CL, wherein $V_H$ and $V_L$ forms an antigen binding site that specifically binds PD-L1, and wherein $V_HH$ specifically binds CTLA-4. In some embodiments, the $V_H$ and $V_L$ domains are derived from atezolizumab. In some embodiments, the $V_H$ and $V_HH$ domains are fused to each other via a peptide linker, such as a peptide linker comprising the amino acid sequence of SEQ ID NO: 1, 8 or 13. In some embodiments, the $C_H2$ and $C_H3$ domains are derived from an IgG4 Fc. In some embodiments, the BABP has the structure as shown in FIG. 9.

In some embodiments, there is provided a multispecific (such as bispecific) antigen binding protein comprising: (a) a first antigen binding portion comprising a full-length antibody (such as duravalumab or atezolizumab) consisting of two heavy chains and two light chains, wherein the full-length antibody specifically binds PD-L1; and (b) a second antigen binding portion comprising an sdAb that specifically binds TIM-3, wherein the first antigen binding portion and the second antigen binding portion are fused to each other. In some embodiments, the sdAb is a camelid, humanized, or human sdAb. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the peptide linker comprises the amino acid sequence of SEQ ID NO: 1, 8 or 13. In some embodiments, the first antigen binding fragment comprises an Fc region, such as an IgG4 Fc.

In some embodiments, there is provided a multispecific (such as bispecific) antigen binding protein comprising: (a) a first antigen binding portion comprising a full-length antibody (such as duravalumab or atezolizumab) consisting of two heavy chains and two light chains, wherein the full-length antibody specifically binds PD-L1; and (b) a second antigen binding portion comprising an sdAb that specifically binds LAG-3, wherein the first antigen binding portion and the second antigen binding portion are fused to each other. In some embodiments, the sdAb is a camelid, humanized, or human sdAb. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the peptide linker comprises the amino acid sequence of SEQ ID NO: 1, 8 or 13. In some embodiments, the first antigen binding fragment comprises an Fc region, such as an IgG4 Fc.

In some embodiments, there is provided a multispecific (such as bispecific) antigen binding protein comprising: (a) a first antigen binding portion comprising a full-length antibody (such as duravalumab or atezolizumab) consisting of two heavy chains and two light chains, wherein the full-length antibody specifically binds PD-L1; and (b) a second antigen binding portion comprising an sdAb that specifically binds VISTA, wherein the first antigen binding portion and the second antigen binding portion are fused to each other. In some embodiments, the sdAb is a camelid, humanized, or human sdAb. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the peptide linker comprises the amino acid sequence of SEQ ID NO: 1, 8 or 13. In some embodiments, the first antigen binding fragment comprises an Fc region, such as an IgG4 Fc.

In some embodiments, there is provided a multispecific (such as bispecific) antigen binding protein comprising: (a) a first antigen binding portion comprising a full-length antibody (such as trastuzumab) consisting of two heavy chains and two light chains, wherein the full-length antibody specifically binds HER2 receptor; and (b) a second antigen binding portion comprising an sdAb that specifically binds CD3, wherein the first antigen binding portion and the second antigen binding portion are fused to each other. In some embodiments, the sdAb is a camelid, humanized, or human sdAb. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the peptide linker comprises the amino acid sequence of SEQ ID NO: 1, 8 or 13. In some embodiments, the first antigen binding fragment comprises an Fc region, such as IgG4 Fc.

In some embodiments, there is provided a multispecific (such as bispecific) antigen binding protein comprising: (a) a first antigen binding portion comprising a full-length antibody (such as LC10) consisting of two heavy chains and two light chains, wherein the full-length antibody specifically binds Ang2; and (b) a second antigen binding portion comprising an sdAb that specifically binds VEGF, wherein the first antigen binding portion and the second antigen binding portion are fused to each other. In some embodiments, the sdAb is a camelid, humanized, or human sdAb. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the peptide linker comprises the amino acid sequence of SEQ ID NO: 1, 8 or 13. In some embodiments, the first antigen binding fragment comprises an Fc region, such as IgG1 Fc.

In some embodiments, there is provided a bispecific antigen binding protein comprising: (a) a first polypeptide comprising from N-terminus to C-terminus: $V_H$—$C_H1$-$C_H2$-$C_H3$-$V_HH$; and (b) a second polypeptide comprising from N-terminus to C-terminus: VL-CL, wherein $V_H$ and $V_L$ forms an antigen binding site that specifically binds Ang2, and wherein $V_HH$ specifically binds VEGF. In some embodiments, the $V_H$ and $V_L$ domains are derived from LC10. In some embodiments, the $C_H3$ and $V_HH$ domains are fused to each other via a peptide linker, such as a peptide linker comprising the amino acid sequence of SEQ ID NO: 1, 8 or 13. In some embodiments, the $C_H2$ and $C_H3$ domains are derived from an IgG1 Fc. In some embodiments, the BABP has the structure as shown in FIG. 4.

In some embodiments, there is provided a bispecific antigen binding protein comprising: (a) a first polypeptide comprising from N-terminus to C-terminus: $V_HH$-$V_H$-$C_H1$-$C_H2$-$C_H3$; and (b) a second polypeptide comprising from N-terminus to C-terminus: VL-CL, wherein $V_H$ and $V_L$ forms an antigen binding site that specifically binds Ang2, and wherein $V_HH$ specifically binds VEGF. In some embodiments, the $V_H$ and $V_L$ domains are derived from LC10. In some embodiments, the $V_H$ and $V_HH$ domains are fused to each other via a peptide linker, such as a peptide linker comprising the amino acid sequence of SEQ ID NO: 1, 8 or 13. In some embodiments, the $C_H2$ and $C_H3$ domains are derived from an IgG1 Fc. In some embodiments, the BABP has the structure as shown in FIG. 9.

In some embodiments, there is provided a bispecific antigen binding protein comprising: (a) a first polypeptide comprising from N-terminus to C-terminus: $V_H$—$C_H1$-$C_H2$-$C_H3$; and (b) a second polypeptide comprising from N-terminus to C-terminus: VL-CL-$V_HH$, wherein $V_H$ and $V_L$ forms an antigen binding site that specifically binds Ang2, and wherein $V_HH$ specifically binds VEGF. In some embodiments, the $V_H$ and $V_L$ domains are derived from LC10. In some embodiments, the $C_L$ and $V_HH$ domains are fused to each other via a peptide linker, such as a peptide linker comprising the amino acid sequence of SEQ ID NO: 1, 8 or 13. In some embodiments, the $C_H2$ and $C_H3$ domains are derived from an IgG1 Fc. In some embodiments, the BABP has the structure as shown in FIG. 11.

In some embodiments, there is provided a bispecific antigen binding protein comprising: (a) a first polypeptide comprising from N-terminus to C-terminus: $V_H$—$C_H1$-$C_H2$-$C_H3$; and (b) a second polypeptide comprising from N-terminus to C-terminus: $V_HH$-VL-CL, wherein $V_H$ and $V_L$ forms an antigen binding site that specifically binds Ang2, and wherein $V_HH$ specifically binds VEGF. In some embodiments, the $V_H$ and $V_L$ domains are derived from LC10. In some embodiments, the $V_L$ and $V_HH$ domains are fused to each other via a peptide linker, such as a peptide linker comprising the amino acid sequence of SEQ ID NO: 1, 8 or 13. In some embodiments, the $C_H2$ and $C_H3$ domains are derived from an IgG1 Fc. In some embodiments, the BABP has the structure as shown in FIG. 13.

In some embodiments, there is provided a multispecific (such as bispecific) antigen binding protein comprising: (a) a first antigen binding portion comprising a full-length antibody (such as adalimumab) consisting of two heavy chains and two light chains, wherein the full-length antibody specifically binds TNF-α; and (b) a second antigen binding portion comprising an sdAb that specifically binds IL-1β, wherein the first antigen binding portion and the second antigen binding portion are fused to each other. In some embodiments, the sdAb is a camelid, humanized, or human sdAb. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the peptide linker comprises the amino acid sequence of SEQ ID NO: 1, 8 or 13. In some embodiments, the first antigen binding fragment comprises an Fc region, such as an IgG1 Fc.

In some embodiments, there is provided a multispecific (such as bispecific) antigen binding protein comprising: (a) a first antigen binding portion comprising a full-length antibody (such as mepolizumab) consisting of two heavy chains and two light chains, wherein the full-length antibody specifically binds IL-5; and (b) a second antigen binding portion comprising an sdAb that specifically binds eotaxin-1, wherein the first antigen binding portion and the second antigen binding portion are fused to each other. In some embodiments, the sdAb is a camelid, humanized, or human sdAb. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the peptide linker comprises the amino acid sequence of SEQ ID NO: 1, 8 or 13. In some embodiments, the first antigen binding fragment comprises an Fc region, such as an IgG1 Fc.

Properties of the MABPs

The MABPs described herein are amenable for manufacture and development as a biologic drug. In some embodiments, the MABP can be recombinantly produced at high expression levels. In some embodiments, the MABP can be recombinantly produced at a level sufficient for industrial production. In some embodiments, the MABP can be expressed transiently in mammalian cells. In some embodiments, the expression level of the MABP in mammalian cell culture is comparable to that of the parent 4-chain antibodies, such as no less than about any one of 50%, 60%, 70%, 80%, 90%, 95%, or 100% solubility as the parent 4-chain antibody. As used herein, the "parent 4-chain antibody" refers to an antibody, such as a full-length 4-chain antibody, comprising the VH and the VL of the first antigen binding portion. In some embodiments, the expression level of the MABP in mammalian cell culture is higher than that of the parent 4-chain antibodies. In some embodiments, the expression level of the MABP in mammalian cell culture (e.g., CHO cells) is at least about any one of 10 mg/L, 15 mg/L, 20 mg/L, 30 mg/L, 40 mg/L, 50 mg/L, 60 mg/L, 70 mg/L, 80 mg/L, 90 mg/L, 100 mg/L, 110 mg/L, 120 mg/L, 150 mg/L or higher. Expression levels of the MABP in a cell culture can be determined using known methods in the art, such as by SDS-PAGE analysis, or analysis using a High-Performance Liquid Chromatography (HPLC) or Fast Protein Liquid Chromatography (FPLC).

In some embodiments, the MABP produced by recombinant expression can be purified to homogeneity or substantial homogeneity by a size exclusion chromatography. In some embodiments, the percentage of mono-dispersive molecule (e.g., as a monomeric MABP molecule, such as a dimeric protein consisting of 4 polypeptide chains) in the purified MABP, e.g., as determined by chromatography, is at least about any one of 90%, 91%, 92%, 93%, 94%, 95%, 96%, 97%, 98%, 99%, 99.5% or higher. The homogeneity of the MABP in a composition can be determined using known methods in the art, such as by SDS-PAGE analysis, dynamic light scattering (DLS), or analysis using an HPLC or FPLC. In some embodiments, the yield of the MABP from the purification is at least about any one of 50%, 60%, 70%, 80%, 90% or higher. In some embodiments, the yield of the MABP from the purification is about 70% to about 95%.

The MABPs described herein further has various biophysical properties that are amenable for use as a biologic drug, including, for example, high solubility, high long-term stability, and thermal stability. Stability of the MABP can be determined using known methods in the art, including Dynamic light scattering (DSL), which profiles different populations of a molecule in soluble based on their particle sizes. In some embodiments, at least about 90%, 91%, 92%, 93%, 94%, 95% or higher of the MABP in a composition is a non-aggregated conformation, i.e., as single, monomeric MABP molecules, e.g., a dimeric protein consisting of 4 polypeptide chains. In some embodiments, the level of aggregation, i.e., association of multiple MABP molecules as a complex, in a composition is no more than about any one of 1%, 2%, 3%, 4%, 5%, 6%, 7%, 8%, 9%, 10% or higher. In some embodiments, the time to form at least about 5% aggregation of the MABP in a composition is at least about any one of 1 day, 3 days, 7 days, 2 weeks, 3 weeks, 4 weeks or more at about 4° C. In some embodiments, the time to form at least about 5% aggregation of the MABP in a composition is at least about any one of 1 day, 3 days, 7 days, 2 weeks, 3 weeks, 4 weeks or more at about room temperature, e.g., 25° C. In some embodiments, the time to form at least about 10% aggregation of the MABP in a composition is at least about any one of 1 day, 2 days, 3 days, 4 days, 6 days, 7 days, 10 days, 2 weeks or more at physiological temperature, e.g., about 37° C.

In some embodiments, the MABP has comparable solubility, such as no less than about any one of 50%, 60%, 70%, 80%, 90%, 95%, or 100% solubility as the parent 4-chain antibody or the sdAbs. In some embodiments, the MABP has higher solubility than the parent 4-chain antibodies or the sdAbs. In some embodiments, the MABP is soluble at a concentration of at least about any one of 50 mg/mL, 75 mg/mL, 100 mg/mL, 125 mg/mL, 150 mg/mL, 175 mg/mL, 200 mg/mL, 225 mg/mL, 250 mg/mL, 300 mg/mL or higher, for example, in a PBS buffer at pH 7.2. The solubility of the MABPs can be measured using any known methods in the art, including concentration using a centrifugation filter followed by protein quantification, or passing the MABP over an IgG-coupled cross-interaction chromatography (CIC) column. In some embodiments, the retention factor k' of the MABP on a cross-interaction chromatography (CIC) column is no more than about any one of 0.2, 0.1, 0.09, 0.08, 0.07, 0.06, 0.05, 0.04, 0.03, 0.02, 0.01 or less.

In some embodiments, the MABP has comparable thermal stability as the parent 4-chain antibody or antigen-binding fragment thereof. In some embodiments, the MABP has higher thermal stability than the parent 4-chain antibodies or antigen-binding fragment thereof. Thermal stability can be measured using known methods in the art, including Capillary Differential Scanning Calorimetry (DSC) and DLS coupled to gradual heating. In some embodiments, the MABP has an aggregation onset temperature ($T_{agg}$) of at least about 65° C., such as at least about any one of 66° C., 67° C., 68° C., 69° C., 70° C., 71° C., 72° C., 73° C., 74° C., 75° C. or higher. In some embodiments, the MABP has an aggregation onset temperature ($T_{agg}$) of about 65° C. to about 75° C. In some embodiments, the MABP has an unfolding midpoint temperature ($T_m$) of at least about 65° C., such as at least about 66° C., 67° C., 68° C., 69° C., 70° C., 71° C., 72° C., 73° C., 74° C., 75° C. or higher. In some embodiments, the MABP has an unfolding midpoint temperature ($T_m$) of about 65° C. to about 75° C.

In some embodiments, the MABP has a high long-term stability. In some embodiments, the MABP is stable for at least about any one of 1 day, 3 days, 7 days, 2 weeks, 3 week, 4 weeks or more at about 4° C. In some embodiments, the MABP has a high long-term stability at an elevated temperature. In some embodiments, the MABP is stable for at least about any one of 1 day, 3 days, 7 days, 2 weeks, 3 week, 4 weeks or more at room temperature, such as about 25° C. or higher. In some embodiments, the MABP is stable for at least about any one of 1 day, 2 days, 3 days, 4 days, 6 days, 7 days, 10 days, 2 weeks or more at physiological temperature, such as about 37° C. or higher. In some embodiments, the stability of the MABP is tested in an accelerated stability assessment program, for example, at about any one of 40° C., 50° C., 60° C., 70° C. or higher do derive the stability of the MABP at a lower temperature. In some embodiments, the MABP has a high long-term stability at a high concentration, such as at least about any one of 50 mg/mL, 100 mg/mL, 150 mg/mL, 200 mg/mL or higher. As used herein, a "stable" composition is substantially free (such as less than about any of 10%, 9%, 8%, 7%, 6%, 5%, 4%, 3%, 2%, 1% or less) of precipitation and/or aggregation. Precipitation can be detected by optical spectroscopy. Aggregation can be detected by e.g., DLS.

In some embodiments, the MABP has high stability over freeze-thaw cycles. In some embodiments, a composition comprising the MABP can be freeze-thawed for at least about any one of 3, 4, 5, 6, 7, 8, 9, 10 times or more without losing structural integrity (e.g., forming aggregates) and/or activity of the MABP. In some embodiments, the composition comprising the MABP can be freeze-thawed at high concentration, such as at least about any one of 50 mg/mL, 100 mg/mL, 150 mg/mL, 200 mg/mL or higher.

Further provided are fragments derived from any one of the multispecific antigen binding proteins described herein, for example, Fab-like domains.

III. Pharmaceutical Compositions

Further provided by the present application are pharmaceutical compositions comprising any one of the MABPs and a pharmaceutically acceptable carrier. Pharmaceutical compositions can be prepared by mixing a MABP having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions.

In some embodiments, the pharmaceutical composition has a high concentration of the MABP. In some embodiments, the concentration of MABP in the pharmaceutical composition is at least about any one of 50 mg/mL, 75 mg/mL, 100 mg/mL, 125 mg/mL, 150 mg/mL, 175 mg/mL, 200 mg/mL, 225 mg/mL, 250 mg/mL, 300 mg/mL or higher. In some embodiments, the pharmaceutical composition has high thermal stability and long-term stability. In some embodiments, the pharmaceutical composition can be stored at about room temperature (e.g., about 25° C.) for at least about any one of 1 day, 3 days, 7 days, 2 weeks, 3 weeks, 4 weeks or more. In some embodiments, the pharmaceutical composition can be stored at a physiological temperature (e.g., about 37° C.) for at least about any one of 1 day, 2 days, 3 days, 4 days, 5 days, 7 days, 10 days, 2 weeks or longer. In some embodiments, the pharmaceutical composition can be freeze-thawed for at least about any one of 3, 4, 5, 6, 7, 8, 9, 10 times or more without losing structural integrity (e.g., forming aggregates) and/or activity of the MABP. In some embodiments, the shelf life of the pharmaceutical composition is at least about any one of 1 weeks, 2 weeks, 3 weeks, 4 weeks, 2 months, 3 months, or longer.

Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or non-ionic surfactants.

Buffers are used to control the pH in a range which optimizes the therapeutic effectiveness, especially if stability is pH dependent. Buffers are preferably present at concentrations ranging from about 50 mM to about 250 mM. Suitable buffering agents for use in the present application include both organic and inorganic acids and salts thereof. For example, citrate, phosphate, succinate, tartrate, fumarate, gluconate, oxalate, lactate, acetate. Additionally, buffers may comprise histidine and trimethylamine salts such as Tris.

Preservatives are added to retard microbial growth, and are typically present in a range from 0.2%-1.0% (w/v). Suitable preservatives for use in the present application include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between 0.1% to 25% by weight, preferably 1 to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the pharmaceutical compositions to be used for in vivo administration, they must be sterile. The pharmaceutical composition may be rendered sterile by filtration through sterile filtration membranes. The pharmaceutical compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

Sustained-release preparations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The pharmaceutical compositions herein may also contain more than one active compound as necessary for the particular indication being treated, preferably those with complementary activities that do not adversely affect each other. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 18th edition.

An exemplary pharmaceutical formulation of the MABP is a liquid formulation comprising sodium citrate, sodium chloride, mannitol, diethylenetriaminepentacetic acid (pentetic acid), and polysorbate 80 (Tween 80), at pH 6.0. In some embodiments, the MABP is formulated in a liquid formulation comprising 4% Sucrose, 50 mM Histidine, 50 mM Arginine, at pH 6.0.

IV. Methods of Use

The multispecific antigen binding proteins described herein, and the compositions (such as pharmaceutical compositions) thereof are useful for a variety of applications, such as in diagnosis, molecular assays, and therapy.

In some embodiments, there is a method of treating a disease or a condition in an individual in need thereof, comprising administering an effective amount of a pharmaceutical composition comprising a multispecific (such as bispecific) antigen binding protein and a pharmaceutically acceptable carrier, wherein the MABP comprises (a) a first antigen binding portion comprising a heavy chain variable domain ($V_H$) and a light chain variable domain ($V_L$), wherein the $V_H$ and $V_L$ together form an antigen-binding site that specifically binds a first epitope, and (b) a second antigen binding portion comprising an sdAb that specifically binds a second epitope, wherein the first antigen binding portion and the second antigen binding portion are fused to each other. In some embodiments, the sdAb is a camelid, humanized, or human sdAb. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the first antigen binding portion comprises a full-length 4-chain antibody. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc or IgG4 Fc.

Methods of Treating a Cancer

In some embodiments, there is provided a method of treating a cancer in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a heavy chain variable domain ($V_H$) and a light chain variable domain ($V_L$), wherein the $V_H$ and $V_L$ together form an antigen-binding site that specifically binds a first epitope, and (b) a second antigen binding portion comprising an sdAb that specifically binds a second epitope, wherein the first antigen binding portion and the second antigen binding portion are fused to each other. In some embodiments, the sdAb is a camelid, humanized, or human sdAb. In some embodiments, the cancer is selected from the group consisting of breast cancer, renal cancer, melanoma, lung cancer, glioblastoma, head and neck cancer, prostate cancer, ovarian carcinoma, bladder carcinoma, and lymphoma. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the first antigen binding portion comprises a full-length 4-chain antibody. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc or IgG4 Fc.

In some embodiments, there is provided a method of treating a cancer in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a heavy chain variable domain ($V_H$) and a light chain variable domain ($V_L$), wherein the $V_H$ and $V_L$ together form an antigen-binding site that specifically binds a first immune checkpoint molecule, and (b) a second antigen binding portion comprising an sdAb (e.g., a $V_H$H) that specifically binds a second immune checkpoint molecule, wherein the first antigen binding portion and the second antigen binding portion are fused to each other. In some embodiments, the sdAb is a camelid, humanized, or human sdAb. In some embodiments, the first immune checkpoint molecule and/or the second immune checkpoint molecule is selected from the group consisting of PD-1, PD-L1, PD-L2, CTLA-4, B7-H3, TIM-3, LAG-3, VISTA, ICOS, 4-1BB, OX40, GITR, and CD40. In some embodiments, the cancer is selected from the group consisting of breast cancer, renal cancer, melanoma, lung cancer, glioblastoma, head and neck cancer, prostate cancer, ovarian carcinoma, bladder carcinoma, and lymphoma. In some embodiments, the first antigen binding portion comprises a heavy chain comprising the $V_H$ and a light chain comprising the $V_L$. In some embodiments, the second antigen binding portion is fused to the first antigen binding portion at the N-terminus of the heavy chain, the N-terminus of the light chain, the N-terminus of the Fc region, the C-terminus of the heavy chain, or the C-terminus of the light chain. In some embodiments, the first antigen binding portion comprises a full-length 4-chain antibody. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG4 Fc.

In some embodiments, there is provided a method of treating a cancer in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a full-length antibody (such as pembrolizumab or nivolumab) consisting of two heavy chains and two light chains, wherein the full-length antibody specifically binds PD-1; and (b) a second antigen binding portion comprising an sdAb (e.g., a $V_H$H) that specifically binds CTLA-4, wherein the first antigen binding portion and the second antigen binding portion are fused to each other. In some embodiments, the sdAb is a camelid, humanized, or human sdAb. In some embodiments, the sdAb binds CTLA-4 with a high affinity. In some embodiments, the sdAb binds CTLA-4 with a medium affinity. In some embodiments, the sdAb binds CTLA-4 with a low affinity. In some embodiments, the cancer is selected from the group consisting of breast cancer, renal cancer, melanoma, lung cancer, glioblastoma, head and neck cancer, prostate cancer, ovarian carcinoma, bladder carcinoma, and lymphoma. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG4 Fc.

In some embodiments, there is provided a method of treating a cancer in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a full-length antibody (such as pembrolizumab or nivolumab) consisting of two heavy chains and two light chains, wherein the full-length antibody specifically binds PD-1; and (b) a second antigen binding portion comprising an sdAb that specifically binds TIM-3, wherein the first antigen binding portion and the second antigen binding portion are fused to each other. In some embodiments, the sdAb is a camelid, humanized, or human sdAb. In some embodiments, the cancer is selected from the group consisting of breast cancer, renal cancer, melanoma, lung cancer, glioblastoma, head and neck cancer, prostate cancer, ovarian carcinoma, bladder carcinoma, and lymphoma. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG4 Fc.

In some embodiments, there is provided a method of treating a cancer in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a full-length antibody (such as pembrolizumab or nivolumab) consisting of two heavy chains and two light chains, wherein the full-length antibody specifically binds PD-1; and (b) a second antigen binding portion comprising an sdAb that specifically binds LAG-3, wherein the first antigen binding portion and the second antigen binding portion are fused to each other. In some embodiments, the sdAb is a camelid, humanized, or human sdAb. In some embodiments, the cancer is selected from the group consisting of breast cancer, renal cancer, melanoma, lung cancer, glioblastoma, head and neck cancer, prostate cancer, ovarian carcinoma, bladder carcinoma, and lymphoma. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG4 Fc.

In some embodiments, there is provided a method of treating a cancer in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a full-length antibody (such as pembrolizumab or nivolumab) consisting of two heavy chains and two light chains, wherein the full-length antibody specifically binds PD-1; and (b) a second antigen binding portion comprising an sdAb that specifically binds VISTA, wherein the first antigen binding portion and the second antigen binding portion are fused to each other. In some embodiments, the sdAb is a camelid, humanized, or human sdAb. In some embodiments, the cancer is selected from the group consisting of breast cancer, renal cancer, melanoma, lung cancer, glioblastoma, head and neck cancer, prostate cancer, ovarian carcinoma, bladder carcinoma, and lymphoma. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG4 Fc.

In some embodiments, there is provided a method of treating a cancer in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising pembrolizumab consisting of two heavy chains and two light chains; and (b) a second antigen binding portion comprising an anti-CTLA-4 sdAb, wherein the first antigen binding portion and the second antigen binding portion are fused to each other. In some embodiments, the sdAb is a camelid, humanized, or human sdAb. In some embodiments, the cancer is selected from the group consisting of breast cancer, renal cancer, melanoma, lung cancer, glioblastoma, head and neck cancer, prostate cancer, ovarian carcinoma, bladder carcinoma, and lymphoma. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the peptide linker comprises the amino acid sequence of SEQ ID NO: 1, 8 or 13. In some embodiments, the first antigen binding fragment comprises an Fc region, such as an IgG4 Fc.

In some embodiments, there is provided a method of treating a cancer in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a full-length antibody (such as durvalumab or atezolizumab) consisting of two heavy chains and two light chains, wherein the full-length antibody specifically binds PD-L1; and (b) a second antigen binding portion comprising an sdAb that specifically binds CTLA-4, wherein the first antigen binding portion and the second antigen binding portion are fused to each other. In some embodiments, the sdAb is a camelid, humanized, or human sdAb. In some embodiments, the sdAb binds CTLA-4 with a high affinity. In some embodiments, the sdAb binds CTLA-4 with a medium affinity. In some embodiments, the sdAb binds CTLA-4 with a low affinity. In some embodiments, the cancer is selected from the group consisting of breast cancer, renal cancer, melanoma, lung cancer, glioblastoma, head and neck cancer, prostate cancer, ovarian carcinoma, bladder carcinoma, and lymphoma. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG4 Fc.

In some embodiments, there is provided a method of treating a cancer in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a full-length antibody (such as durvalumab or atezolizumab) consisting of two heavy chains and two light chains, wherein the full-length antibody specifically binds PD-L1; and (b) a second antigen binding portion comprising an sdAb that specifically binds TIM-3, wherein the first antigen binding portion and the second antigen binding portion are fused to each other. In some embodiments, the sdAb is a camelid, humanized, or human sdAb. In some embodiments, the cancer is selected from the group consisting of breast cancer, renal cancer, melanoma, lung cancer, glioblastoma, head and neck cancer, prostate cancer, ovarian carcinoma, bladder carcinoma, and lymphoma. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG4 Fc.

In some embodiments, there is provided a method of treating a cancer in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a full-length antibody (such as durvalumab or atezolizumab) consisting of two heavy chains and two light chains, wherein the full-length antibody specifically binds PD-L1; and (b) a second antigen binding portion comprising an sdAb that specifically binds LAG-3, wherein the first antigen binding portion and the second antigen binding portion are fused to each other. In some embodiments, the sdAb is a camelid, humanized, or human sdAb. In some embodiments, the cancer is selected from the group consisting of breast cancer, renal cancer, melanoma, lung cancer, glioblastoma, head and neck cancer, prostate cancer, ovarian carcinoma, bladder carcinoma, and lymphoma. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG4 Fc.

In some embodiments, there is provided a method of treating a cancer in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a full-length antibody (such as durvalumab or atezolizumab) consisting of two heavy chains and two light chains, wherein the full-length antibody specifically binds PD-L1; and (b) a second antigen binding portion comprising an sdAb that specifically binds VISTA, wherein the first antigen binding portion and the second antigen binding portion are fused to each other. In some embodiments, the sdAb is a camelid, humanized, or human sdAb. In some embodiments, the cancer is selected from the group consisting of breast cancer, renal cancer, melanoma, lung cancer, glioblastoma, head and neck cancer, prostate cancer, ovarian carcinoma, bladder carcinoma, and lymphoma. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG4 Fc.

In some embodiments, there is provided a method of treating a cancer in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a heavy chain variable domain ($V_H$) and a light chain variable domain ($V_L$), wherein the $V_H$ and $V_L$ together form an antigen-binding site that specifically binds a first tumor antigen, and (b) a second antigen binding portion comprising an sdAb (e.g., a $V_H H$) that specifically binds a second tumor antigen, wherein the first antigen binding portion and the second antigen binding portion are fused to each other. In some embodiments, the sdAb is a camelid, humanized, or human sdAb. In some embodiments, the first tumor antigen and/or the second tumor antigen is selected from the group consisting of HER2, BRAF, EGFR, VEGFR2, CD20, RANKL, CD38, and CD52. In some embodiments, the first antigen binding portion comprises a full-length anti-HER-2 monoclonal antibody (such as trastuzumab) or antigen binding fragment thereof. In some embodiments, the cancer is selected from the group consisting of breast cancer, renal cancer, melanoma, lung cancer, glioblastoma, head and neck cancer, prostate cancer, ovarian carcinoma, bladder carcinoma, and lymphoma. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc.

In some embodiments, there is provided a method of treating a cancer in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a heavy chain variable domain ($V_H$) and a light chain variable domain ($V_L$), wherein the $V_H$ and $V_L$ together form an antigen-binding site that specifically binds a tumor antigen, and (b) a second antigen binding portion comprising an sdAb (e.g., a $V_HH$) that specifically binds a cell surface antigen on an immune effector cell (such as T cell), wherein the first antigen binding portion and the second antigen binding portion are fused to each other. In some embodiments, the sdAb is a camelid, humanized, or human sdAb. In some embodiments, the tumor antigen is selected from the group consisting of HER2, BRAF, EGFR, VEGFR2, CD20, RANKL, CD38, and CD52. In some embodiments, the first antigen binding portion comprises a full-length anti-HER-2 monoclonal antibody (such as trastuzumab) or antigen binding fragment thereof. In some embodiments, the cancer is selected from the group consisting of breast cancer, renal cancer, melanoma, lung cancer, glioblastoma, head and neck cancer, prostate cancer, ovarian carcinoma, bladder carcinoma, and lymphoma. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc.

In some embodiments, there is provided a method of treating a cancer in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a heavy chain variable domain ($V_H$) and a light chain variable domain ($V_L$), wherein the $V_H$ and $V_L$ together form an antigen-binding site that specifically binds a first angiogenic factor (such as Ang-2), and (b) a second antigen binding portion comprising an sdAb (e.g., a $V_HH$) that specifically binds a second angiogenic factor (such as VEGF), wherein the first antigen binding portion and the second antigen binding portion are fused to each other. In some embodiments, the sdAb is a camelid, humanized, or human sdAb. In some embodiments, the cancer is selected from the group consisting of breast cancer, renal cancer, melanoma, lung cancer, glioblastoma, head and neck cancer, prostate cancer, ovarian carcinoma, bladder carcinoma, and lymphoma. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc.

In some embodiments, there is provided a method of treating a cancer (such as breast cancer) in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a full-length antibody (such as trastuzumab) consisting of two heavy chains and two light chains, wherein the full-length antibody specifically binds HER2 receptor; and (b) a second antigen binding portion comprising an sdAb that specifically binds CD3, wherein the first antigen binding portion and the second antigen binding portion are fused to each other. In some embodiments, the sdAb is a camelid, humanized, or human sdAb. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG4 Fc.

The methods described herein are suitable for treating various cancers, including both solid cancer and liquid cancer. The methods are applicable to cancers of all stages, including early stage, advanced stage and metastatic cancer. The methods described herein may be used as a first therapy, second therapy, third therapy, or combination therapy with other types of cancer therapies known in the art, such as chemotherapy, surgery, radiation, gene therapy, immunotherapy, bone marrow transplantation, stem cell transplantation, targeted therapy, cryotherapy, ultrasound therapy, photodynamic therapy, radio-frequency ablation or the like, in an adjuvant setting or a neoadjuvant setting.

Methods of Treating Inflammatory or Autoimmune Disease

In some embodiments, there is provided a method of treating an inflammatory or autoimmune disease in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a heavy chain variable domain ($V_H$) and a light chain variable domain ($V_L$), wherein the $V_H$ and $V_L$ together form an antigen-binding site that specifically binds a first epitope, and (b) a second antigen binding portion comprising an sdAb that specifically binds a second epitope, wherein the first antigen binding portion and the second antigen binding portion are fused to each other. In some embodiments, the sdAb is a camelid, humanized, or human sdAb.

In some embodiments, the inflammatory or autoimmune disease is selected from the group consisting of arthritis (such as rheumatoid arthritis, juvenile idiopathic arthritis, psoriatic arthritis, ankylosing spondylitis, and arthritic ulcerative colitis), colitis, psoriasis, severe asthma, and moderate to severe Cronh's disease. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc.

In some embodiments, there is provided a method of treating an inflammatory or autoimmune disease in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a heavy chain variable domain ($V_H$) and a light chain variable domain ($V_L$), wherein the $V_H$ and $V_L$ together form an antigen-binding site that specifically binds a first pro-inflammatory molecule, and (b) a second antigen binding portion comprising an sdAb that specifically binds a second pro-inflammatory molecule, wherein the first antigen binding portion and the second antigen binding portion are fused to each other. In some embodiments, the sdAb is a camelid, humanized, or human sdAb. In some embodiments, the inflammatory or autoimmune disease is selected from the group consisting of arthritis (such as rheumatoid arthritis, juvenile idiopathic arthritis, psoriatic arthritis, ankylosing spondylitis, and arthritic ulcerative colitis), colitis, psoriasis, severe asthma, and moderate to severe Cronh's disease. In some embodiments, the first pro-inflammatory molecule and/or the second pro-inflammatory molecule is selected from the group consisting of IL-1β, TNF-α, IL-5, IL-6, IL-6R, and eotaxin-1. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc.

In some embodiments, there is provided a method of treating an inflammatory or autoimmune disease in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a full-length antibody (such as adalimumab) consisting of two heavy chains and two light chains, wherein the full-length antibody specifically binds TNF-α; and (b) a second antigen binding portion comprising an sdAb that specifically binds IL-1β, wherein the first antigen binding portion and the second antigen binding portion are fused to each other. In some embodiments, the sdAb is a camelid, humanized, or human sdAb. In some embodiments, the inflammatory or autoimmune disease is selected from the group consisting of arthritis (such as rheumatoid arthritis, juvenile idiopathic arthritis, psoriatic arthritis, ankylosing spondylitis, and arthritic ulcerative colitis), colitis, psoriasis, severe asthma, and moderate to severe Cronh's disease. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc.

In some embodiments, there is provided a method of treating an inflammatory or autoimmune disease in an individual in need thereof, comprising administering an effective amount of a pharmaceutical composition comprising a multispecific (such as bispecific) antigen binding protein and a pharmaceutically acceptable carrier, wherein the MABP comprises: (a) a first antigen binding portion comprising a full-length antibody (such as mepolizumab) consisting of two heavy chains and two light chains, wherein the full-length antibody specifically binds IL-5; and (b) a second antigen binding portion comprising an sdAb that specifically binds eotaxin-1, wherein the first antigen binding portion and the second antigen binding portion are fused to each other. In some embodiments, the sdAb is a camelid, humanized, or human sdAb. In some embodiments, the inflammatory or autoimmune disease is selected from the group consisting of arthritis (such as rheumatoid arthritis, juvenile idiopathic arthritis, psoriatic arthritis, ankylosing spondylitis, and arthritic ulcerative colitis), colitis, psoriasis, severe asthma, and moderate to severe Cronh's disease. In some embodiments, the second antigen binding portion is fused to the first antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the second antigen binding portion is fused to the first antigen binding portion chemically. In some embodiments, the second antigen binding portion is fused to the first antigen binding portion via a peptide bond or a peptide linker. In some embodiments, the peptide linker is no more than about 30 (such as no more than about any one of 25, 20, or 15) amino acids long. In some embodiments, the first antigen binding fragment comprises an Fc region, such as an IgG1 Fc.

Dosage and Routes of Administration

Dosages and desired drug concentrations of pharmaceutical compositions of the present application may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

When in vivo administration of the MABPs described herein are used, normal dosage amounts may vary from about 10 ng/kg up to about 100 mg/kg of mammal body weight or more per day, preferably about 1 mg/kg/day to 10 mg/kg/day, depending upon the route of administration. It is within the scope of the present application that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

In some embodiments, the pharmaceutical composition is administered for a single time. In some embodiments, the pharmaceutical composition is administered for multiple times (such as any of 2, 3, 4, 5, 6, or more times). In some embodiments, the pharmaceutical composition is administered once per week, once 2 weeks, once 3 weeks, once 4 weeks, once per month, once per 2 months, once per 3 months, once per 4 months, once per 5 months, once per 6 months, once per 7 months, once per 8 months, once per 9 months, or once per year. In some embodiments, the interval between administrations is about any one of 1 week to 2 weeks, 2 weeks to 1 month, 2 weeks to 2 months, 1 month to 2 months, 1 month to 3 months, 3 months to 6 months, or 6 months to a year. The optimal dosage and treatment regime for a particular patient can readily be determined by one skilled in the art of medicine by monitoring the patient for signs of disease and adjusting the treatment accordingly.

The pharmaceutical compositions of the present application, including but not limited to reconstituted and liquid formulations, are administered to an individual in need of treatment with the MABPs, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes.

In some embodiments, the pharmaceutical compositions are administered to the individual by subcutaneous (i.e. beneath the skin) administration. For such purposes, the pharmaceutical compositions may be injected using a syringe. However, other devices for administration of the pharmaceutical compositions are available such as injection devices; injector pens; auto-injector devices, needleless devices; and subcutaneous patch delivery systems.

In some embodiments, the pharmaceutical compositions are administered to the individual intravenously. In some embodiments, the pharmaceutical composition is administered to an individual by infusion, such as intravenous infusion. Infusion techniques for immunotherapy are known in the art (see, e.g., Rosenberg et al., New Eng. J. of Med. 319: 1676 (1988)).

V. Methods of Preparation

The present application also provides isolated nucleic acids encoding the MABPs, vectors and host cells comprising such isolated nucleic acids, and recombinant methods for the production of the MABPs.

For recombinant production of the MABP, the nucleic acids encoding the full-length antibody or antigen binding fragment of the first antigen binding portion, and the sdAb are isolated and inserted into a replicable vector for further cloning (amplification of the DNA) or for expression. In some embodiments, the nucleic acid encoding the full-length antibody or antigen binding fragment of the first antigen binding portion is recombinantly fused to the nucleic acid encoding the sdAb of the second antigen binding portion and optionally via a nucleic acid encoding a peptide linker, all in frame for translation with respect to each other to provide a nucleic acid encoding the MABP. DNA encoding the MABP, components thereof, or the sdAb is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin. Alternatively, the first antigen binding fragment and the second antigen binding fragment are each prepared recombinantly using prokaryotic or eukaryotic host cells comprising nucleic acids that encode the first antigen binding fragment and the second antigen binding fragment respectively. The expressed first antigen binding fragment and the second antigen binding fragment are then conjugated chemically, and purified in order to provide the MABP.

1. Protein Production in Prokaryotic Cells
a) Vector Construction

Polynucleotide sequences encoding polypeptide components of the MABP of the present application can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present application. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as GEM™-11 may be utilized in making a recombinant vector which can be used to transform susceptible host cells such as E. coli LE392.

The expression vector described herein may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the -galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) *Cell* 20: 269) using linkers or adaptors to supply any required restriction sites.

In one aspect, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this application should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In some embodiments, the signal sequences used in both cistrons of the expression system are STII signal sequences or variants thereof.

In some embodiments, the production of the MABPs can occur in the cytoplasm of the host cell, and therefore does not require the presence of secretion signal sequences within each cistron. In some embodiments, polypeptide components, such as the polypeptide encoding the $V_H$ domain of the first antigen binding portion optionally fused to the second antigen binding portion, and the polypeptide encoding the $V_L$ domain of the first antigen binding portion optionally fused to the second antigen binding portion, are expressed, folded and assembled to form functional MABPs within the cytoplasm. Certain host strains (e.g., the E. coli trxB strains) provide cytoplasm conditions that are favorable for disulfide bond formation, thereby permitting proper folding and assembly of expressed protein subunits. Proba and Pluckthun *Gene*, 159:203 (1995).

The present application provides an expression system in which the quantitative ratio of expressed polypeptide components can be modulated in order to maximize the yield of secreted and properly assembled the MABPs of the present application. Such modulation is accomplished at least in part by simultaneously modulating translational strengths for the polypeptide components. One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleotide sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

Preferably, a set of vectors is generated with a range of TIR strengths for each cistron therein. This limited set provides a comparison of expression levels of each chain as well as the yield of the desired MABP products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the present application.

b) Prokaryotic Host Cells.

Prokaryotic host cells suitable for expressing the MABPs of the present application include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*,

*Vitreoscilla,* or *Paracoccus.* In one embodiment, gram-negative cells are used. In one embodiment, *E. coli* cells are used as hosts. Examples of *E. coli* strains include strain W3110 (Bachmann, *Cellular and Molecular Biology*, vol. 2 (Washington, D.C.: American Society for Microbiology, 1987), pp. 1190-1219; ATCC Deposit No. 27,325) and derivatives thereof, including strain 33D3 having genotype W3110 AfhuA (AtonA) ptr3 lac Iq lacL8 AompT A (nmpc-fepE) degP41 kan$^R$ (U.S. Pat. No. 5,639,635). Other strains and derivatives thereof, such as *E. coli* 294 (ATCC 31,446), *E. coli* B, *E. coli* 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., *Proteins,* 8:309-314 (1990). It is generally necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon.

Typically the host cell should secrete minimal amounts of proteolytic enzymes, and additional protease inhibitors may desirably be incorporated in the cell culture.

c) Protein Production

Host cells are transformed with the above-described expression vectors and cultured in conventional nutrient media modified as appropriate for inducing promoters, selecting transformants, or amplifying the genes encoding the desired sequences. Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the MABPs of the present application are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli,* the pH is preferably from about 6.8 to about 7.4, and more preferably about 7.0.

If an inducible promoter is used in the expression vector, protein expression is induced under conditions suitable for the activation of the promoter. In some embodiments, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* (2002), 263:133-147). A variety of other inducers may be used, according to the vector construct employed, as is known in the art.

The expressed MABPs of the present application are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Alternatively, protein production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

During the fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the MABPs of the present application, various fermentation conditions can be modified. For example, to improve the proper assembly and folding of the secreted polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275:17106-17113; Arie et al. (2001) *Mol. Microbiol.* 39:199-210.

To minimize proteolysis of expressed heterologous proteins (especially those that are proteolytically sensitive), certain host strains deficient for proteolytic enzymes can be used for the present application. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., *Microbial Drug Resistance*, 2:63-72 (1996).

*E. coli* strains deficient for proteolytic enzymes and transformed with plasmids overexpressing one or more chaperone proteins may be used as host cells in the expression system encoding the MABPs of the present application.

d) Protein Purification

The MABPs produced herein are further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In some embodiments, Protein A immobilized on a solid phase is used for immunoaffinity purification of the MABPs comprising an Fc region described herein. Protein A is a 411 (D cell wall protein from *Staphylococcus aureas* which binds with a high affinity to the Fc region of antibodies. Lindmark et al (1983) *J. Immunol. Meth.* 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants. The solid phase is then washed to remove contaminants non-specifically bound to the solid phase. Finally the MABPs of interest are recovered from the solid phase by elution.

2. Protein Production in Eukaryotic Cells

For Eukaryotic expression, the vector components generally include, but are not limited to, one or more of the following, a signal sequence, an origin of replication, one or more marker genes, and enhancer element, a promoter, and a transcription termination sequence.

a) Signal Sequence Component

A vector for use in a eukaryotic host may also an insert that encodes a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the MABPs of the present application.

b) Origin of Replication

Generally, the origin of replication component is not needed for mammalian expression vectors (the SV40 origin may typically be used only because it contains the early promoter).

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up nucleic acid encoding the MABPs of the present application, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with the polypeptide encoding-DNA sequences, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

d) Promoter Component

Expression and cloning vectors usually contain a promoter that is recognized by the host organism and is operably linked to the nucleic acid encoding the desired polypeptide sequences. Virtually all eukaryotic genes have an AT-rich region located approximately 25 to 30 based upstream from the site where transcription is initiated. Another sequence found 70 to 80 bases upstream from the start of the transcription of many genes is a CNCAAT region where N may be any nucleotide. A the 3' end of most eukaryotic is an AATAAA sequence that may be the signal for addition of the poly A tail to the 3' end of the coding sequence. All of these sequences may be inserted into eukaryotic expression vectors.

Other promoters suitable for use with prokaryotic hosts include the phoA promoter, -lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the MABPs.

Polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human-interferon cDNA in mouse cells under the control of a thymidine kinase promoter from herpes simplex virus. Alternatively, the Rous Sarcoma Virus long terminal repeat can be used as the promoter.

e) Enhancer Element Component

Transcription of a DNA encoding the MABPs of the present application by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the polypeptide encoding sequence, but is preferably located at a site 5' from the promoter.

f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the polypeptide-encoding mRNA. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for MABPs production and cultured in conventional nutrient media modified as appropriate for inducing promoters, selecting transformants, or amplifying the genes encoding the desired sequences.

h) Culturing the Host Cells

The host cells used to produce the MABPs of the present application may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

i) Protein Purification

When using recombinant techniques, the MABPs can be produced intracellularly, in the periplasmic space, or directly secreted into the medium. If the MABP or the sdAb is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the MABP or the sdAb is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the MABP. Protein A can be used to purify the MABPs that are based on human immunoglobulins containing 1, 2, or 4 heavy chains (Lindmark et al., *J. Immunol. Meth.* 62:1-13 (1983)). Protein G is recommended for all mouse isotypes and for human 3 (Guss et al., *EMBO J.* 5:15671575 (1986)). The matrix to which the affinity ligand is attached is most often agarose, but other matrices are available. Mechanically stable matrices such as controlled pore glass or poly(styrene-divinyl)benzene allow for faster flow rates and shorter processing times than can be achieved with agarose. Where the MABP comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the MABP or the sdAb to be recovered.

Following any preliminary purification step(s), the mixture comprising the MABP or the sdAb of interest and contaminants may be subjected to low pH hydrophobic interaction chromatography using an elution buffer at a pH between about 2.5-4.5, preferably performed at low salt concentrations (e.g., from about 0-0.25M salt).

3. Antibody Production

Components of the MABPs, such as conventional 4-chain antibodies, antigen-binding fragments, and sdAbs, can be produced using any known methods in the art, including methods described below.

The sdAbs (such as $V_H$Hs) may be obtained using methods known in the art such as by immunizing a Camelidae species (such as camel or llama) and obtaining hybridomas therefrom, or by cloning a library of sdAbs using molecular biology techniques known in the art and subsequent selection by ELISA with individual clones of unselected libraries or by using phage display.

1) Monoclonal Antibodies

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986).

The immunizing agent will typically include the antigenic protein or a fusion variant thereof. Generally either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principles and Practice*, Academic Press (1986), pp. 59-103.

Immortalized cell lines are usually transformed mammalian cells, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, Calif. USA, and SP-2 cells (and derivatives thereof, e.g., X63-Ag8-653) available from the American Type Culture Collection, Manassas, Va. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen. Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells, Review articles on recombinant expression in bacteria of DNA encoding the antibody include Skerra et al, *Curr. Opinion in Immunol.*, 5:256-262 (1993) and Pliickthun, *Immunol Revs.* 130:151-188 (1992).

In a further embodiment, antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nucl. Acids Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

2) Humanized Antibodies

The antibodies may further comprise humanized or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domain, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Jones et al., *Nature* 321: 522-525 (1986); Riechmann et al, *Nature* 332: 323-329 (1988) and Presta, *Curr. Opin. Struct. Biol.* 2: 593-596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., *Nature* 321:522-525 (1986); Riechmann et al., *Nature* 332:323-327 (1988); Verhoeyen et al., *Science* 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al, *J. Immunol,* 151:2296 (1993); Chothia et al., *J. Mol. Biol.* 196:901 (1987). Another method uses a particular framework derived from the consensus sequence of all human antibodies of a particular subgroup of light or heavy chains. The same framework may be used for several different humanized antibodies. Carter et al., *Proc. Natl. Acad. Sci. USA*, 89:4285 (1992); Presta et al., *J. Immunol,* 151:2623 (1993).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Various forms of the humanized antibody are contemplated. For example, the humanized antibody may be an antibody fragment, such as an Fab, which is optionally conjugated with one or more cytotoxic agent(s) in order to generate an immunoconjugate. Alternatively, the humanized antibody may be an intact antibody, such as an intact IgG1 antibody.

In some embodiments, the sdAbs are modified, such as humanized, without diminishing the native affinity of the domain for antigen and while reducing its immunogenicity with respect to a heterologous species. For example, the amino acid residues of the antibody variable domain ($V_H$H) of an llama antibody can be determined, and one or more of the Camelidae amino acids, for example, in the framework regions, are replaced by their human counterpart as found in the human consensus sequence, without that polypeptide losing its typical character, i.e. the humanization does not significantly affect the antigen binding capacity of the resulting polypeptide. Humanization of Camelidae sdAbs requires the introduction and mutagenesis of a limited amount of amino acids in a single polypeptide chain. This is in contrast to humanization of scFv, Fab', (Fab')2 and IgG, which requires the introduction of amino acid changes in two chains, the light and the heavy chain and the preservation of the assembly of both chains.

3) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); U.S. Pat. No. 5,591,669 and WO 97/17852. Transgenic mice or rats capable of producing fully human sdAbs are known in the art. See, e.g., US20090307787A1, U.S. Pat. No. 8,754,287, US20150289489A1, US20100122358A1, and WO2004049794.

Alternatively, phage display technology can be used to produce human antibodies and antibody fragments in vitro, from immunoglobulin variable (V) domain gene repertoires from unimmunized donors. McCafferty et al., *Nature* 348: 552-553 (1990); Hoogenboom and Winter, *J. Mol. Biol.* 227: 381 (1991). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David *J., Curr. Opin Struct. Biol.* 3:564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., EMBO J. 12:725-734 (1993). See also, U.S. Pat. Nos. 5,565,332 and 5,573,905.

The techniques of Cole et al., and Boerner et al., are also available for the preparation of human monoclonal antibodies (Cole et al., Monoclonal Antibodies and Cancer Therapy, Alan R. Liss, p. 77 (1985) and Boerner et al., *J. Immunol.* 147(1): 86-95 (1991). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly and antibody repertoire. This approach is described, for example, in U.S. Pat. Nos. 5,545,807; 5,545,806, 5,569,825, 5,625,126, 5,633,425, 5,661,016 and in the following scientific publications: Marks et al., *Bio/Technology* 10: 779-783 (1992); Lonberg et al., *Nature* 368: 856-859 (1994); Morrison, *Nature* 368: 812-13 (1994), Fishwild et al., *Nature Biotechnology* 14: 845-51 (1996), Neuberger, *Nature Biotechnology* 14: 826 (1996) and Lonberg and Huszar, *Intern. Rev. Immunol.* 13: 65-93 (1995).

Finally, human antibodies may also be generated in vitro by activated B cells (see U.S. Pat. Nos. 5,567,610 and 5,229,275).

4) Antibody Fragments

In certain circumstances there are advantages to using antibody fragments, such as antigen binding fragments, rather than whole antibodies. Smaller fragment sizes allow for rapid clearance, and may lead to improved access to solid tumors.

Various techniques have been developed for the production of antibody fragments. Traditionally, these fragments were derived via proteolytic digestion of intact antibodies (see, e.g., Morimoto et al., *J Biochem Biophys. Method.* 24:107-117 (1992); and Brennan et al., *Science* 229:81 (1985)), However, these fragments can now be produced directly by recombinant host cells. Fab, Fv and scFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ with increase in vivo half-life is described in U.S. Pat. No. 5,869,046. In other embodiments, the antibody of choice is a single chain Fv fragment (scFv). See WO 93/16185; U.S. Pat. Nos. 5,571,894 and 5,587,458. The antibody fragment may also be a "linear antibody", e.g., as described in U.S. Pat. No. 5,641,870. Such linear antibody fragments may be monospecific or bispecific.

5) Bispecific and Multispecific Antibodies

Bispecific antibodies (BsAbs) are antibodies that have binding specificities for at least two different epitopes, including those on the same or another protein. Alternatively, one arm can bind the target antigen, and another arm can be combined with an arm that binds a triggering molecule on a leukocyte such as a T-cell receptor molecule (e.g., CD3), or Fc receptors for IgG (FcγR) such as FcγR1 (CD64), FcγRII (CD32) and FcγRIII (CD16), so as to focus and localize cellular defense mechanisms to the target antigen-expressing cell. Such antibodies can be derived from full length antibodies or antibody fragments (e.g. F(ab')$_2$ bispecific antibodies).

Bispecific antibodies may also be used to localize cytotoxic agents to cells which express the target antigen. Such antibodies possess one arm that binds the desired antigen and another arm that binds the cytotoxic agent (e.g., saporin, anti-interferon-α, vinca alkaloid, ricin A chain, methotrexate or radioactive isotope hapten). Examples of known bispecific antibodies include anti-ErbB2/anti-FcgRIII (WO 96/16673), anti-ErbB2/anti-FcgRI (U.S. Pat. No. 5,837,234), anti-ErbB2/anti-CD3 (U.S. Pat. No. 5,821,337).

Methods for making bispecific antibodies are known in the art. Traditional production of full length bispecific antibodies is based on the coexpression of two immunoglobulin heavy-chain/light chain pairs, where the two chains have different specificities. Millstein et al., *Nature*, 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecules provides for an easy way of separation. This approach is disclosed in WO 94/04690, For further details of generating bispecific antibodies, see, for example, Suresh et al., *Methods in Enzymology* 121: 210 (1986).

According to another approach described in WO 96/27011 or U.S. Pat. No. 5,731,168, the interface between a pair of antibody molecules can be engineered to maximize the percentage of heterodimers which are recovered from recombinant cell culture. The preferred interface comprises at least a part of the $C_H3$ region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., *Science* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175: 217-225 (1992) describes the production of fully humanized bispecific antibody F(ab')$_2$ molecules. Each Fab' fragment was separately secreted from *E. coli* and subjected to directed chemical coupling in vitro to form the bispecific antibody. The bispecific antibody thus formed was able to bind cells overexpressing the ErbB2 receptor and normal human T cells, as well as trigger the lytic activity of human cytotoxic lymphocytes against human breast tumor targets.

Various techniques for making and isolating bivalent antibody fragments directly from recombinant cell culture have also been described. For example, bivalent heterodimers have been produced using leucine zippers. Kostelny et al., *J. Immunol.*, 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Natl. Acad. Sci.*; 4, 90: 6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (scFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.* 147: 60 (1991).

Exemplary bispecific antibodies may bind two different epitopes on a given molecule. Alternatively, an anti-protein arm may be combined with an arm which binds a triggering molecule on a leukocyte such as a T-cell receptor molecule (e.g., CD2, CD3, CD28 or B7), or Fc receptors for IgG (FcγR), such as FcγRI (CD64), FcγRII (CD32) and FcγRIII (CD16) so as to focus cellular defense mechanisms to the cell expressing the particular protein. Bispecific antibodies may also be used to localize cytotoxic agents to cells which express a particular protein. Such antibodies possess a protein-binding arm and an arm which binds a cytotoxic agent or a radionuclide chelator, such as EOTUBE, DPTA, DOTA or TETA. Another bispecific antibody of interest binds the protein of interest and further binds tissue factor (TF).

6) Multivalent Antibodies

A multivalent antibody may be internalized (and/or catabolized) faster than a bivalent antibody by a cell expressing an antigen to which the antibodies bind. The antibodies used as the first antigen binding portion in the MABPs of the present application can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X$_2$)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: $V_H$-$C_H$1-flexible linker-$V_H$-$C_H$1-Fc region chain; or $V_H$-$C_H$1-$V_H$-$C_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a $C_L$ domain.

7) Heteroconjugate Antibodies

Heteroconjugate antibodies can also be used as the first antigen binding portion of the MABPs of the present application. Heteroconjugate antibodies are composed of two covalently joined antibodies. For example, one of the antibodies in the heteroconjugate can be coupled to avidin, the other to biotin. Such antibodies have, for example, been proposed to target immune system cells to unwanted cells, U.S. Pat. No. 4,676,980, and for treatment of HIV infection. WO 91/00360, WO 92/200373 and EP 0308936. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may be made using any convenient cross-linking methods. Suitable cross-linking agents are well known in the art, and are disclosed in U.S. Pat. No. 4,676,980, along with a number of cross-linking techniques.

8) Effector Function Engineering

It may be desirable to modify the MABPs of the present application with respect to Fc effector function, e.g., so as to modify (e.g., enhance or eliminate) antigen-dependent cell-mediated cytotoxicity (ADCC) and/or complement dependent cytotoxicity (CDC) of the antibody. In a preferred embodiment, Fc effector function of the MABP is reduced or eliminated. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric MABP thus generated may have improved internalization capability and/or increased complement-mediated cell killing and antibody-dependent cellular cytotoxicity (ADCC). See Caron et al., *J. Exp Med.* 176:1191-1195 (1992) and Shopes, *J. Immunol* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989).

To increase the serum half-life of the antibody, one may incorporate a salvage receptor binding epitope into the MABP as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

9) Other Amino Acid Sequence Modifications

Amino acid sequence modification(s) of the antibodies, such as single chain antibodies or antibody components of the MABPs, described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells in *Science,* 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table 2 below under the heading of "preferred substitutions". If such substitutions result in a change in biological activity, then more substantial changes, denominated "exemplary substitutions" in Table II, or as further described below in reference to amino acid classes, may be introduced and the products screened.

TABLE II

Amino Acid Substitutions

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | Ala | ala |
| Ser (S) | Thr | thr |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and its target (e.g., PD-L1, B7.1). Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants to the MABPs of the present application are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant versions.

10) Other Modifications

The MABPs of the present application can be further modified to contain additional nonproteinaceous moieties that are known in the art and readily available. Preferably, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in *Remington: The Science and Practice of Pharmacy*, 20th Ed., Alfonso Gennaro, Ed., Philadelphia College of Pharmacy and *Science* (2000).

VI. Kits and Articles of Manufacture

Further provided are kits, unit dosages, and articles of manufacture comprising any of the MABPs described herein. In some embodiments, a kit is provided comprising any one of the pharmaceutical compositions described herein and preferably provides instructions for its use.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder described herein, and may have a sterile access port (for example the container may be an intravenous solution bag or a vial having a stopper pierceable by a hypodermic injection needle). The label or package insert indicates that the composition is used for treating the particular condition in an individual. The label or package insert will further comprise instructions for administering the composition to the individual. The label may indicate directions for reconstitution and/or use. The container holding the pharmaceutical composition may be a multi-use vial, which allows for repeat administrations (e.g. from 2-6 administrations) of the reconstituted formulation. Package insert refers to instructions customarily included in commercial packages of therapeutic products that contain information about the indications, usage, dosage, administration, contraindications and/or warnings concerning the use of such therapeutic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the pharmaceutical composition and instructions for use, packaged in quantities sufficient for storage and use in pharmacies, for example, hospital pharmacies and compounding pharmacies.

EXAMPLES

The examples below are intended to be purely exemplary of the invention and should therefore not be considered to limit the invention in any way. The following examples and detailed description are offered by way of illustration and not by way of limitation.

Example 1: Construction, Expression and Biophysical Characterization of PD-1/CTLA-4 Bispecific Antigen Binding Proteins This example describes the construction and expression of exemplary PD-1/CTLA-4 bispecific antigen binding proteins (BABP). 15 constructs were designed and expressed, each comprising two polypeptide chains as follows.

Constructs 1-3 (BCP-73, BCP-74, BCP-75): The first polypeptide comprises from the N-terminus to the C terminus: the $V_HH$ domain of an anti-CTLA-4 sdAb (sdAb-1 for BCP-73, sdAb-2 for BCP-74, and sdAb-3 for BCP-75), a peptide linker (a modified sequence from human IgG1 hinge region, e.g., SEQ ID NO: 13), the heavy chain variable domain $V_H$ of pembrolizumab, and heavy chain constant domains of IgG4. The second polypeptide comprises from the N-terminus to the C-terminus: the light chain variable domain $V_L$ of pembrolizumab, and antibody kappa light chain $C_L$ domain. The three BABPs have the format of FIG. 9.

Construct 4-6 (BCP-78, BCP-79, BCP-80): The first polypeptide comprises from the N-terminus to the C terminus: the $V_HH$ domain of an anti-CTLA-4 sdAb (sdAb-1 for BCP-78, sdAb-2 for BCP-79, and sdAb-3 for BCP-80), a peptide linker (SEQ ID NO: 13), the heavy chain variable domain $V_H$ of nivolumab, and heavy chain constant domains of IgG4. The second polypeptide comprises from the N-terminus to the C-terminus: the light chain variable domain $V_L$ of nivolumab, and antibody kappa light chain $C_L$ domain. The three BABPs have the format of FIG. 9.

Construct 7 (BCP-2): The first polypeptide comprises from the N-terminus to the C terminus: the heavy chain variable domain $V_H$ of pembrolizumab, heavy chain constant domains of IgG4, a peptide linker (GGGGSGGGS, SEQ ID NO: 1), and the $V_HH$ domain of an anti-CTLA-4 sdAb (sdAb-1). The second polypeptide comprises from the N-terminus to the C-terminus: the light chain variable domain $V_L$ of pembrolizumab, and antibody kappa light chain $C_L$ domain. BCP-2 has the format of FIG. 4.

Construct 8 (BCP-16): The first polypeptide comprises from the N-terminus to the C terminus: the heavy chain variable domain $V_H$ of pembrolizumab, and heavy chain constant domains of IgG4. The second polypeptide comprises from the N-terminus to the C-terminus: the $V_HH$ domain of an anti-CTLA-4 sdAb (sdAb-1), a peptide linker (human IgG1 hinge region, e.g., SEQ ID NO: 8), the light chain variable domain $V_L$ of pembrolizumab, and antibody kappa light chain $C_L$ domain. BCP-16 has the format of FIG. 13.

Construct 9 (BCP-17): The first polypeptide comprises from the N-terminus to the C terminus: the heavy chain variable domain $V_H$ of pembrolizumab, and heavy chain constant domains of IgG4. The second polypeptide comprises from the N-terminus to the C-terminus: the light chain variable domain $V_L$ of pembrolizumab, antibody kappa light chain $C_L$ domain, a peptide linker (SEQ ID NO: 8), the $V_HH$ domain of an anti-CTLA-4 sdAb (sdAb-1). BCP-17 has the format of FIG. 11.

Construct 10 (BCP-31): The first polypeptide comprises from the N-terminus to the C terminus: the $V_HH$ domain of an anti-CTLA-4 sdAb (sdAb-1), a peptide linker (SEQ ID NO: 1), the heavy chain variable domain $V_H$ of pembrolizumab, and heavy chain constant domains of IgG4. The second polypeptide comprises from the N-terminus to the C-terminus: the $V_HH$ domain of an anti-CTLA-4 sdAb (sdAb-1), a peptide linker (SEQ ID NO: 1), the light chain variable domain $V_L$ of pembrolizumab, and antibody kappa light chain $C_L$ domain. BCP-31 has the format of FIG. 17.

Construct 11 (BCP-32): The first polypeptide comprises from the N-terminus to the C terminus: the $V_HH$ domain of an anti-CTLA-4 sdAb (sdAb-1), a peptide linker (SEQ ID NO: 1), the $V_HH$ domain of an anti-CTLA-4 sdAb (sdAb-1), a peptide linker (SEQ ID NO: 1), the heavy chain variable domain $V_H$ of pembrolizumab, and heavy chain constant domains of IgG4. The second polypeptide comprises from the N-terminus to the C-terminus: the light chain variable domain $V_L$ of pembrolizumab, and antibody kappa light chain $C_L$ domain. BCP-32 has the format of FIG. 18.

Construct 12 (BCP-33): The first polypeptide comprises from the N-terminus to the C terminus: the heavy chain variable region of pembrolizumab, constant $C_H1$ region of IgG4, a peptide linker (SEQ ID NO: 8), the $V_HH$ domain of an anti-CTLA-4 sdAb (sdAb-1), and the Fc region of IgG1. The second polypeptide comprises from the N-terminus to the C-terminus: the light chain variable domain $V_L$ of pembrolizumab, and antibody kappa light chain $C_L$ domain. BCP-33 has the format of FIG. 19.

Construct 13 (BCP-34): The polypeptide comprises from the N-terminus to the C terminus: the light chain variable domain $V_L$ of pembrolizumab, a peptide linker (GGGGSGGGGSGGGGS, SEQ ID NO: 12), the heavy chain variable domain $V_H$ of pembrolizumab, a peptide linker (SEQ ID NO: 8), the $V_HH$ domain of an anti-CTLA-4 sdAb (sdAb-1), and Fc region of IgG1. BCP-34 has the format of FIG. 20.

Construct 14 (BCP-35): The first polypeptide comprises from the N-terminus to the C terminus: the heavy chain variable region of pembrolizumab, constant $C_H1$ region of IgG4, a peptide linker (SEQ ID NO: 8), the $V_HH$ domain of an anti-CTLA-4 sdAb (sdAb-1), constant $C_H1$ region of IgG4, and the Fc region of IgG4. The second polypeptide comprises from the N-terminus to the C-terminus: the light chain variable region of pembrolizumab, antibody kappa light chain $C_L$ domain, a peptide linker (SEQ ID NO: 8), the $V_HH$ domain of an anti-CTLA-4 sdAb (sdAb-1), and antibody kappa light chain $C_L$ domain. BCP-35 has the format of FIG. 21.

Construct 15 (BCP-36): The first polypeptide comprises from the N-terminus to the C terminus: the light chain variable domain $V_L$ of pembrolizumab, a peptide linker (SEQ ID NO: 12), the heavy chain variable domain $V_H$ of pembrolizumab, a peptide linker (SEQ ID NO: 8), the $V_HH$ domain of an anti-CTLA-4 sdAb (sdAb-1), and Fc region of IgG1. The second polypeptide comprises from the N-terminus to the C-terminus: the $V_HH$ domain of an anti-CTLA-4 sdAb (sdAb-1), and antibody kappa light chain $C_L$ domain. BCP-36 has the format of FIG. 22.

Each BABP consists of two copies of the first polypeptide and two copies of the second polypeptide. An S228P mutation can be introduced to the IgG4 Fc region to inhibit Fab arm exchange. Furthermore, the Fc region of the BABP may be swapped with an IgG Fc of a different isotype, for example, the IgG1 isotype. The Fc region of IgG4 isotype has low binding affinity to FcγRs, and thus is preferable over IgG1 isotype in some embodiments for avoiding ADCC-mediated depletion of PD-1 or CTLA-4 positive cells.

Production

The plasmids of the 15 BABP constructs described above were prepared and transiently expressed in CHO-3E7 cells. The BABPs were purified by one-step protein A chromatography and stored in PBS buffer, pH7.4. The composition and purity of the purified BABPs were analyzed by SDS-PAGE under both reduced and non-reduced conditions. The sizes of the polypeptide chains as well as the full-length BABP molecules were consistent with their calculated molecular mass based on the amino acid sequences. To further study the physical properties of the BABPs in solution, size exclusion chromatography was used to analyze each protein. All BABPs exhibited a single major peak, demonstrating physical homogeneity as monomeric molecules, i.e., non-aggregated BABP molecules each being a dimeric protein consisting of 4 polypeptide chains, including 2 copies of the first polypeptide chain and 2 copies of the second polypeptide chain. A summary of this data is shown in the Table 1. Data in Table 1 shows that the production levels of most BABPs are comparable to those of the regular monoclonal antibodies, indicating that the BABPs can be expressed efficiently in mammalian cells.

The purified BABPs could also be formulated in a solution containing sodium citrate, sodium chloride, mannitol, diethylenetriaminepentacetic acid (pentetic acid), and polysorbate 80 (Tween 80), pH 6.0.

TABLE 1

Production of exemplary PD-1/CTLA-4 BABPs.

| BABP | Host cell | Transient expression (mg/L) | Monomeric molecule (HPLC) | Storage buffer |
|---|---|---|---|---|
| BCP-73 | CHO-3E7 | 13.15 | 94.20% | PBS, pH 7.2 |
| BCP-74 | CHO-3E7 | 13.45 | 94.00% | PBS, pH 7.2 |
| BCP-75 | CHO-3E7 | 14.55 | 94.70% | PBS, pH 7.2 |
| BCP-78 | CHO-3E7 | 106.3 | 96.60% | PBS, pH 7.2 |
| BCP-79 | CHO-3E7 | 122.4 | 93.60% | PBS, pH 7.2 |
| BCP-80 | CHO-3E7 | 102.4 | 94.10% | PBS, pH 7.2 |
| BCP-2 | CHO-3E7 | 20.5 | 97.90% | PBS, pH 7.2 |
| BCP-16 | CHO-3E7 | 4.65 | 98.30% | PBS, pH 7.2 |
| BCP-17 | CHO-3E7 | 12.35 | 92.30% | PBS, pH 7.2 |
| BCP-31 | CHO-3E7 | 31.05 | 95.20% | PBS, pH 7.2 |
| BCP-32 | CHO-3E7 | 29.7 | 93.90% | PBS, pH 7.2 |
| BCP-33 | CHO-3E7 | 2.45 | 94.80% | PBS, pH 7.2 |
| BCP-34 | CHO-3E7 | 3.6 | 99.50% | PBS, pH 7.2 |

TABLE 1-continued

Production of exemplary PD-1/CTLA-4 BABPs.

| BABP | Host cell | Transient expression (mg/L) | Monomeric molecule (HPLC) | Storage buffer |
|---|---|---|---|---|
| BCP-35 | CHO-3E7 | 11.25 | 95.40% | PBS, pH 7.2 |
| BCP-36 | CHO-3E7 | 0.45 | 92.90% | PBS, pH 7.2 |

Stability Analysis

The thermal stability of various BABPs were investigated using a MICROCAL™ VP-Capillary Differential Scanning Calorimetry (DSC, Microcal, Northampton, Mass., USA, Malvern Instruments). Approximately 370 μl of each BABP (1 mg/ml) and its corresponding buffer was added to a 96-well plate according to MICROCAL™ VP-Capillary DSC user's manual. A detergent cleaning program was included between each sample run to keep the reference and sample cells clean. All samples were scanned from 20° C. to 100° C. with a scan rate of 90° C./h (1.5° C./min) in a passive mode. The collected data were analyzed using the VP-Capillary DSC software based on ORGIN™ 7.0 (Northampton, Mass., USA). All thermograms were control and baseline subtracted to obtain the apparent midpoint ($T_m$) and apparent enthalpy (ΔH) of protein unfolding. The unfolding Midpoint Temperatures ($T_m$) of various BABPs are shown in Table 2 (DSC).

The formation of larger protein aggregates during heating was followed using dynamic light scattering (DLS). A temperature ramp from 25° C. to 75° C. with temperature interval at about 0.75° C. was performed for samples at 1.5 mg/ml using the DYNAPRO® NANOSTAR® plate reader (Wyatt, Santa Barbara, Calif.). 20 μl of each BABP sample was added to a WYATT® disposable cuvette followed by covering the sample with 10 μl of mineral oil (Sigma 8410) to prevent evaporation. Triplicate measurements (5 acquisitions/each measurement) were averaged for each BABP sample. In the duration of an experiment with the chosen temperature interval, the thermal scan rate was calculated to be 1.5° C./min. Each sample was measured while the temperature was continuously heated until the target temperature reached 75° C. (~40 min). The aggregation temperature ($T_{agg}$) was analyzed with onset analysis method in the DYNAMICS™ 7.6.0.48 software (Wyatt, Santa Barbara, Calif.). The measured aggregation onset temperatures ($T_{agg}$) of various BABPs are shown in Table 2.

TABLE 2

DSC and DLS analysis of exemplary PD-1/CTLA-4 BABPs.

| Construct | $T_m$ (° C.) | $T_{agg}$ (° C.) |
|---|---|---|
| BCP-73 | 69.5 | 69.2 |
| BCP-74 | 68.9 | 70.8 |
| BCP-75 | 67.6 | 70.2 |
| Biosimilar pembrolizumab | 67.6 | 69.6 |
| BCP-78 | 68.9 | 70.8 |
| BCP-79 | 67.9 | 70.6 |
| BCP-80 | 67.8 | 69.2 |
| Biosimilar nivolumab | 65.2 | 67.6 |

BABP samples at concentration of >50 mg/ml in Histidine buffer (pH6.0) were incubated at constant temperatures of 4° C., 25° C. and 37° C. for 7 days. A similar set of samples was also freeze-thawed five times. Fractions of intact full monomeric molecules of all samples were evaluated by SEC-HPLC, and the data was recorded and analyzed using CHROMELEON™ software supplied by the manufacturer. Table 3 shows that the BABPs retained greater than 90% integrity under the thermo-challenged conditions.

TABLE 3

Stability analysis of exemplary PD-1/CTLA-4 BABPs.

Monomeric molecule (by SEC-HPLC)

| Construct | Starting | 4° C. | 25° C. | 37° C. | after 5 freeze-thaw cycles |
|---|---|---|---|---|---|
| BCP-73 | 94.2% | 94.8% | 94.5% | 93.7% | 92.3% |
| BCP-74 | 94.0% | 94.2% | 93.9% | 93.8% | 92.5% |
| BCP-75 | 94.7% | 95.1% | 94.5% | 94.1% | 93.4% |
| BCP-78 | 96.6% | 97.2% | 95.8% | 95.2% | 94.7% |
| BCP-79 | 93.6% | 94.3% | 93.6% | 93.1% | 92.1% |
| BCP-80 | 94.1% | 92.8% | 93.5% | 92.7% | 91.8% |

Solubility Analysis

To characterize the solubility of purified BABPs, 10 mg of each BABP at 1 mg/ml was added to MICROCON®-30 kDa centrifugal concentrators (EMD Millipore) in volumes of ~2.5 ml and centrifuged at 4000×g (4° C.). The volumes were periodically checked and protein was added to the concentrators until the remaining protein solutions had been consumed. Concentration proceeded for 2 h until either the volume reached ~20 μl or stopped decreasing. The concentration was determined by performing UV measurements of samples obtained by diluting 1 μl of concentrated BABP into 199 μl of each respective buffer. The samples were evaluated for aggregation using analytical SEC-HPLC after diluting BABPs to 1 mg/ml in their respective buffers. Table 4 shows that the BABPs retained full integrity under these stressed conditions.

The solubility of purified BABPs was also measured using a cross-interaction chromatography (CIC) column. Murine polyclonal antibodies purified from pooled mouse serum were purchased from Sigma-Aldrich (15381). Murine polyclonal antibodies were coupled to the resin matrix at ~30 mg/mL. Purified BABPs in PBS buffer were injected to the murine IgG-coupled column and the control column, respectively, with concentrations ranging from 0.05 to 0.20 mg/mL. The retention times were used to calculate the retention factor k' values reported in Table 4: k'=(Vr−Vo)/Vo=(Tr−Tm)/Tm. Vr represents the elution volume of the sample on the protein coupled column, Vo represents the elution volume from a control column, Tr represents the retention time on the protein coupled column, and Tm represents the retention time on the control column. A number of samples were run twice on the same column. Antibodies with k' values >0.6 are generally significantly less soluble. According to Table 4, all the BABPs exhibited excellent solubility.

TABLE 4

Solubility analysis of exemplary PD-1/CTLA-4 BABPs.

| Construct | Concentration (mg/mL) | Monemeric molecule | K' |
|---|---|---|---|
| BCP-73 | 194.4 | 94.1% | 0.07 |
| BCP-74 | 189.2 | 92.7% | 0.04 |
| BCP-75 | 290.9 | 92.6% | 0.03 |
| BCP-78 | 248.0 | 93.4% | 0.06 |
| BCP-79 | 337.5 | 93.5% | 0.04 |
| BCP-80 | 206.1 | 92.8% | 0.03 |

Example 2: In Vitro Functional Assays of PD-1/CTLA-4 Bispecific Antigen Binding Proteins The 15 exemplary PD-1/CTLA-4 bispecific antigen binding proteins (BABPs) described in Example 1 were tested in the in vitro assays below to assess the functional blockade of PD-1 and CTLA-4 by the BABPs.

Target Binding Assays

The ability of the BABPs to bind PD-1 and CTLA-4 can be determined using the Surface Plasmon Resonance method (e.g., BIACORE®), an enzyme-linked immunosorbent assay, a Fluorescence-Assisted Cell Sorting method (FACS), or a combination thereof. The analyses can be performed on activated T cells.

Binding affinities of the various BABPs to PD-1 expressed on CHO cells, were determined using a fluorescence-activated cell sorting (FACS)-based assay. BABP samples were prepared (starting at 1 μM, 3-fold serial dilution with 10 concentrations) as primary antibodies for FACS analysis. CHO cells expressing human PD-1 were dissociated from adherent culture flasks and mixed with varying concentrations of BABP samples (both in a 96-well plate). Pembrolizumab (e.g., KEYTRUDA®) or nivolumab (e.g., OPDIVO®) was used as an anti-PD-1 antibody positive control. The mixture was equilibrated for 30 minutes at room temperature, washed three times with FACS buffer (PBS containing 1% BSA). Fluorescein isothiocyanate (FITC)-conjugated anti-human kappa antibody (Jackson ImmunoResearch) used as the secondary antibody was then added and incubated for 15 minutes at room temperature. Cells were washed again with FACS buffer and analyzed by flow cytometry. Data was analyzed with PRISM™ (GraphPad Software, San Diego, Calif.) using non-linear regression, and $EC_{50}$ values were calculated. As shown in Table 5, the FACS binding assays demonstrated that the BABPs retained comparable PD-1 binding affinities as pembrolizumab (e.g., KEYTRUDA®) and nivolumab (e.g., OPDIVO®), respectively.

Binding affinities of the 15 BABPs to CTLA-4 expressed on CHO cells, were determined using a fluorescence-activated cell sorting (FACS)-based assay. BABP samples were prepared (starting at 1 μM, 3-fold serial dilution with 10 concentrations) as primary antibody for FACS analysis. CHO cells expressing human CTLA-4 were dissociated from adherent culture flasks and mixed with varying concentrations of antibodies (both in a 96-well plate). sdAb-1-Fc, sdAb-2-Fc, sdAb-3-Fc and ipilimumab (e.g., YERVOY®) were used as anti-CTLA-4 antibody positive controls. The mixture was equilibrated for 30 minutes at room temperature, washed three times with FACS buffer (PBS containing 1% BSA). Fluorescein isothiocyanate (FITC)-conjugated anti-human kappa antibody (Jackson ImmunoResearch) used as the secondary antibody was then added and incubated for 15 minutes at room temperature. Cells were washed again with FACS buffer and analyzed by flow cytometry. Data were analyzed with PRISM™ (GraphPad Software, San Diego, Calif.) using non-linear regression, and $EC_{50}$ values were calculated. As show in Table 5, the FACS binding assays demonstrated that the BABPs exhibited comparable binding affinities to CTLA-4 as their corresponding sdAbs fused to an Fc. Also, the BABPs showed comparable binding affinities to CTLA-4 as ipilimumab (e.g., YERVOY®).

Binding kinetics of various BABPs to PD-1 were determined using a Surface Plasmon Resonance (SPR) biosensor, BIACORE® T200 (GE Healthcare). Different concentrations of the BABP samples were prepared starting at 50 nM with 3-fold serial dilution. Each BABP sample was immobilized on the sensor chip through the Fc capture method. Antigen PD-1 was used as the analyte. The dissociation ($k_d$) and association ($k_a$) rate constants were obtained using the BIACORE® T200 evaluation software. The apparent equilibrium dissociation constants ($K_D$) were calculated from the ratio of $k_d$ over $k_a$. As shown in Table 5, the BABPs retained comparable binding kinetics to PD-1 as pembrolizumab (e.g., KEYTRUDA®) and nivolumab (e.g., OPDIVO®).

Binding kinetics of various BABPs to CTLA-4 were determined using a Surface Plasmon Resonance (SPR) biosensor, BIACORE® T200 (GE Healthcare). Different concentrations of the BABP samples were prepared starting at 200 nM with 3-fold serial dilution. Each BABP sample was immobilized on the sensor chip through the Fc capture method. Antigen CTLA-4 was used as the analyte. The dissociation (kd) and association ($k_a$) rate constants were obtained using the BIACORE® T200 evaluation software. The apparent equilibrium dissociation constants ($K_D$) were calculated from the ratio of $k_d$ over $k_a$. As shown in Table 5, the binding kinetics demonstrated that the BABPs exhibited comparable binding kinetics to CTLA-4 as their corresponding sdAbs fused to an Fc. Also, the BABPs have comparable binding kinetics to CTLA-4 as biosimilar ipilimumab.

TABLE 5

Binding data of exemplary PD-1/CTLA-4 BABPs.

| | PD-1 | | | CTLA-4 | | |
|---|---|---|---|---|---|---|
| Construct | $K_D$ (nM) | $EC_{50}$ (nM) | $IC_{50}$ (nM) | $K_D$ (nM) | $EC_{50}$ (nM) | $IC_{50}$ (nM) |
| BCP-73 | 7.5 | 2.2 | 1.1 | 7.5 | 3.0 | 11.5 |
| BCP-74 | 2.5 | 1.6 | 2.6 | 2.6 | 3.9 | 17.2 |
| BCP-75 | 2.2 | 1.6 | 1.5 | 4.0 | 3.0 | 11.7 |
| BCP-78 | 8.1 | 1.7 | 4.8 | 6.6 | 2.7 | 7.1 |
| BCP-79 | 6.8 | 1.1 | 3.5 | 2.5 | 1.9 | 7.8 |
| BCP-80 | 6.3 | 1.4 | 5.7 | 5.6 | 3.7 | 11.9 |
| BCP-2 | 5.3 | 5.2 | 2.3 | 11.0 | 16.4 | 11.7 |
| BCP-16 | 3.9 | 12.2 | 8.8 | 4.8 | 26.6 | 8.6 |
| BCP-17 | 3.9 | 2.7 | 4.0 | 39.3 | 17.7 | 33.3 |
| BCP-31 | 8.0 | 3.4 | 5.7 | 4.3 | 31.2 | 15.3 |
| BCP-32 | 7.5 | 8.1 | 4.3 | 4.1 | 71.7 | 14.6 |
| BCP-33 | 8.1 | 1.5 | 2.0 | 9.2 | 48.0 | 26.3 |
| BCP-34 | 9.2 | 5.4 | 4.8 | 6.3 | 24.3 | 18.6 |
| BCP-35 | 7.3 | 3.0 | 4.6 | 7.2 | 20.4 | 17.5 |
| BCP-36 | 8.3 | 1.8 | 2.0 | 6.1 | 26.4 | 17.9 |
| pembrolizumab (KEYTRUDA ®) | 6.5 | 1.1 | 1.3 | N/A | N/A | N/A |
| nivolumab (OPDIVO ®) | 7.3 | 1.1 | 3.1 | N/A | N/A | N/A |
| sdAb-1 | N/A | N/A | N/A | 15.0 | 2.1 | 3.5 |
| sdAb-2 | N/A | N/A | N/A | 4.2 | 3.2 | 4.1 |
| sdAb-3 | N/A | N/A | N/A | 5.5 | 3.5 | 5.1 |
| ipilimumab (YERVOY ®) | N/A | N/A | N/A | 17.3 | 13.2 | 8.5 |

Inhibition of Ligand Binding by FACS Analysis

Inhibition of ligand binding by the BABPs was assessed using a FACS assay.

To assess inhibition of PD-L1 by the BABPs, BABP samples were prepared (starting at 1 μM, 3-fold serial dilution with 10 concentrations). CHO cells expressing human PD-1 were dissociated from adherent culture flasks and mixed with varying concentrations of each BABP and 0.5 μM hPD-L1-Fc fusion protein having a biotin label. Biosimilar pembrolizumab or biosimilar nivolumab was used as an anti-PD-1 antibody positive control. The mixture was equilibrated for 30 minutes at room temperature, and washed three times with FACS buffer (PBS containing 1% BSA). PE/Cy5 Streptavidin secondary antibody was then added to the mixtures and incubated for 15 minutes at room temperature. Subsequently, the cells were washed with FACS buffer and analyzed by flow cytometry. Data was analyzed with PRISM™ (GraphPad Software, San Diego, Calif.) using non-linear regression, and $IC_{50}$ values were calculated (Table 5). The competition assays demonstrated the ability of the BABPs to efficiently inhibit PD-1/PD-L1 interactions at low concentrations (1-10 µg/ml). The binding data in Table 5 indicates that the functional activities of the exemplary PD1/CTLA-4 BABPs are very similar to pembrolizumab (e.g., KEYTRUDA®) and nivolumab (e.g., OPDIVOR®).

To assess inhibition of B7-1 (a CTLA-4 ligand) by the BABPs, BABP samples were prepared (starting at 1 µM, 3-fold serial dilution with 10 concentrations). CHO cells expressing human B7-1 cells were dissociated from adherent culture flasks and mixed with varying concentrations of each BABP and 0.5 µM hCTLA-4-Fc fusion protein having a biotin-label. sdAb-1-Fc, sdAb-2-Fc, sdAb-3-Fc and ipilimumab (e.g., YERVOY®) were used as anti-CTLA-4 antibody positive controls. The mixture was equilibrated for 30 minutes at room temperature, and washed three times with FACS buffer (PBS containing 1% BSA). PE/Cy5 Streptavidin secondary antibody was then added to the mixtures and incubated for 15 minutes at room temperature. Subsequently, the cells were washed again with FACS buffer and analyzed by flow cytometry. Data were analyzed with PRISM™ (GraphPad Software, San Diego, Calif.) using non-linear regression, and $IC_{50}$ values were calculated (Table 5). The competition assays demonstrated the ability of the BABPs to efficiently inhibit CTLA4-B7-1 interactions at low concentrations (1-10 µg/ml). The binding data in Table 5 indicates that the functional activities of the exemplary PD1/CTLA-4 BABPs are similar to their corresponding sdAbs fused to an Fc and biosimilar ipilimumab.

The expression profile and dual-binding properties of the BABPs clearly demonstrate bispecificity of the BABPs, which have a first specificity provided by the antigen binding site formed by correct pairing of the $V_H$ and $V_L$ of the 4-chain antibody, and the second specificity provided by the $V_H$Hs.

In Vitro Functional Assays

Blockade of the PD-1 and CTLA-4 pathways by the BABPs can be studied using a variety of bioassays that monitor T cell proliferation, IFN-'γ release, IL-2 secretion or expression of reporter gene that is driven by signaling in the PD-1 or CTLA-4 pathway.

The BCP-73, BCP-74, BCP-75, BCP-78, BCP-79 and BCP-80 6 BABPs were selected for in vitro bioactivity evaluation. Characterization of biological activity of anti-PD-1 neutralizing antibody in PD-1/PD-L1 cell-based assay using the PD-1/NFAT Reporter-Jurkat cells is shown in Table 6. In this case, CHO-K1 cells were stably expressed with human PD-L1 and an engineered T cell receptor (TCR) activator. The affecter cells-PD-1/NFAT Reporter-Jurkat cells were pre-incubated with serial dilution of BABPs for 30 minutes prior to co-culture with engineered CHO-K1 cells. After ~6 hours of stimulation, ONE-STEP™ Luciferase reagent was added to the cells to measure NFAT activity. Data was analyzed with PRISM™ (GraphPad Software, San Diego, Calif.) using non-linear regression, and $EC_{50}$ values were calculated. The reporter assay demonstrated the ability of all BABPs to efficiently activate NFAT signal similar as pembrolizumab (e.g., KEYTRUDA®) and nivolumab (e.g., OPDIVO®).

TABLE 6

Antibody biological activity

| Construct | PD-1 $EC_{50}$ (nM) | CTLA-4 $EC_{50}$ (nM) |
| --- | --- | --- |
| BCP-73 | 1.6 | 12.1 |
| BCP-74 | 4.3 | 14.3 |
| BCP-75 | 5.5 | 12.1 |
| BCP-78 | 8.9 | 8.4 |
| BCP-79 | 6.5 | 10.9 |
| BCP-80 | 4.7 | 7.4 |
| pembrolizumab (KEYTRUDA®) | 1.5 | N/A |
| nivolumab (OPDIVO®) | 3.3 | N/A |
| sdAb-1-Fc | N/A | 12.1 |
| sdAb-2-Fc | N/A | 12.9 |
| sdAb-3-Fc | N/A | 13.1 |
| ipilimumab (YERVOY®) | N/A | 17.6 |

The bispecific antibodies are found to effectively inhibit the binding between CTLA-4 and B7-1 as shown in Table 6 using CTLA-4 cell-based blockade assay. Briefly, human $CD4^+$ T cells were purified from PBMC by the isolation kits (Miltenyl Biotec). Each well contained $10^5$ $CD4^+$ T cells and $10^4$ CHO-K1/human CD80 (CHO-K1 stably expressing human CD80) with a final working volume of 200 µl. Bispecific antibodies were added into each well at different concentrations. No antibody was used as a background control. Human IgG4 was used as a negative control, and ipilimumab (e.g., YERVOY®) was used as a positive anti-CTLA4 antibody control. CTLA-4-Fc (GenScript, Z03373-50) was added into the system to initiate the reaction. After 24-hour incubation in 37° C./5% $CO_2$ incubator, 100 µl medium was taken from each testing well for IL-2 measurement (Cisbio). Antibody concentration-dependent secretion of IL-2 by T cells in the CTLA-4 blockade bioassays was used to extract an $EC_{50}$ value for each test antibody, as well as for the positive control full-length anti-CTLA-4 antibody ipilimumab (e.g., YERVOY®).

PD-1 pathway inhibition by the BCP-74, BCP-75, BCP-79 and BCP-80 BABPs were studied by determining the IL-2 and IFN-'γ secretion level in mixed lymphocyte reactions (MLR) containing target cells expressing PD-L1 (such as dendritic cells), activated T cells, and each of the BABPs. Human $CD4^+$ T cells and allogeneic monocytes are purified from PBMC using isolation kits (Miltenyl Biotec). Monocytes were induced into dendritic cells. Each well contains $10^5$ CD4+ T cells and $10^4$ allogeneic dendritic cells with a final working volume of 200 µl. Each of the BABPs was added into each well at different concentrations. A no antibody well was used as the background control. Human IgG4 was used as the negative control and pembrolizumab (e.g., KEYTRUDA®) was used as the positive anti-PD-1 antibody control. After incubating for 72 hours at 37° C. in a 5% $CO_2$ incubator, 100 µl medium was taken from each testing well for IL-2 and IFN-'γ measurement (Cisbio). Concentration-dependent secretion of IL-2 and IFN-'γ in the MLRs is used to extract an $EC_{50}$ value for the BABPs against PD-1, which is compared with the $EC_{50}$ value of control PD-1 antibody pembrolizumab (e.g., KEYTRUDA®). As shown in Table 7, various BABPs exhibit comparable inhibition potential to pembrolizumab (e.g., KEYTRUDA®).

TABLE 7

Mixed lymphocyte reactions of PD-1/CTLA-4 BABPs

| Construct | IFN-γ EC50 (nM) | IL-2 EC50 (nM) |
|---|---|---|
| BCP-74 | 1.24 | 1.15 |
| BCP-75 | 0.51 | 2.1 |
| pembrolizumab (KEYTRUDA®) | 0.92 | 1.68 |
| BCP-79 | 0.50 | 2.33 |
| BCP-80 | 0.30 | 1.00 |
| nivolumab (OPDIVO®) | 1.77 | 1.76 |

Example 3: In Vivo Anti-Tumor Efficacy of PD-1/CTLA-4 Bispecific Antigen Binding Proteins This example describes in vivo experiments assessing the functional blockade of PD-1 and CTLA-4 by the BCP-75 and BCP-79 BABPs. Anti-tumor efficacy was evaluated in tumor models developed with human CTLA-4 and PD-1 Knock-in mice. Humanization of both CTLA-4 and PD-1 in mice enabled direct in vivo evaluation of the efficacy of PD-1/CTLA-4 BABPs in a mouse tumor xenograft model.

The mouse xenograft models can be prepared by implanting tumor cells into NSG mice. Tumor cell lines, such as MC38 (a murine colon adenocarcinoma cell line) and CT26 (a murine colon carcinoma cell line), can be used to prepare mouse models for colon cancer. B16, a murine melanoma cell line, can be used to prepare a mouse model for melanoma. Renca, a murine renal cortical adenocarcinoma cell line, can be used to prepare a mouse model for renal cancer.

6-8-week-old human PD-1 KI female C57/BL6 mice were shaved on their lower dorsum and s.c. injected with $1 \times 10^6$ colon cancer cell line MC38 in a 50 μL suspension of 75% (vol/vol) RPMI (Life Technologies) and 25% (vol/vol) medium-density MATRIGEL® (Corning). Mice whose tumors failed to engraft within 7 days by visual inspection were excluded from further study. Tumors were measured on a daily basis starting at day 7 after MC38 engraftment. Mice were individually sorted into treatment cohorts, and started to receive treatment only when tumors reached a threshold of 150 mm$^3$, about 10 days post engraftment in all cases. Digital caliper measurements and body weight measurements were taken every three days for the duration of treatment. In the experiments, mice were given treatment intravenously for 16 days with 10 mg/kg biosimilar pembrolizumab, 10 mg/kg biosimilar nivolumab, or 12.3 mg/kg BABP (BCP-75 or BCP-79). The treatment was administered every 4 days. As shown in FIG. 23, both BCP-75 and BCP-79 effectively controlled tumor growth in the MC38 syngeneic mice model, exhibiting comparable functional activities as biosimilar pembrolizumab and biosimilar nivolumab. None of the three treatment regimens affected the body weights of the MC38 engrafted mice, as compared to the mock control (data not shown).

6-8-week-old human CTLA-4 KI female C57/BL6 mice were shaved on their lower dorsum and s.c. injected with $1 \times 10^6$ colon cancer cell line MC38 in a 50 μl suspension of 75% (vol/vol) RPMI (Life Technologies) and 25% (vol/vol) medium-density MATRIGEL® (Corning). Mice whose tumors failed to engraft within 7 days by visual inspection were excluded from further study. Tumors were measured on a daily basis starting at day 7 after MC38 engraftment. Mice were individually sorted into treatment cohorts, and started to receive treatment only when tumors reached a threshold of 150 mm$^3$, about 10 days post engraftment in all cases. Digital caliper measurements and body weight measurements were taken every three days for the duration of treatment. In the experiments, mice were given treatment intravenously for 16 days with 10 mg/kg biosimilar ipilimumab, 12.3 mg/kg BABP (BCP-75 or BCP-79), or 6.7 mg/kg of sdAb-2-Fc or sdAb-3-Fc. The treatment was administered every 4 days. As shown in FIG. 24, both BCP-75 and BCP-79 effectively controlled tumor growth in the MC38 syngeneic mice model, exhibiting comparable functional activities as sdAb-2-Fc and sdAb-3-Fc. None of the three treatment regimens affected the body weights of the MC38 engrafted mice, as compared to the mock control (data not shown).

Example 4: Construction, Expression and Biophysical Characterization of PD-L1/CTLA-4 Bispecific Antigen Binding Proteins This example describes the construction and expression of exemplary PD-L1/CTLA-4 BABPs. Two constructs were designed and expressed, each comprising two polypeptide chains as follows:

BCP-84: The first polypeptide comprises from the N-terminus to the C terminus: the $V_HH$ domain of an anti-CTLA-4 sdAb-2, a peptide linker (SEQ ID NO: 13), the heavy chain variable domain $V_H$ of atezolizumab, and heavy chain constant domains of non-glycosylated IgG1. The second polypeptide comprises from the N-terminus to the C-terminus: the light chain variable domain $V_L$ of atezolizumab, and antibody kappa light chain $C_L$ domain. BCP-84 has the format of FIG. 9.

BCP-85: The first polypeptide comprises from the N-terminus to the C terminus: the $V_HH$ domain of an anti-CTLA-4 sdAb-3, a peptide linker (SEQ ID NO: 13), the heavy chain variable domain $V_H$ of atezolizumab, and heavy chain constant domain of non-glycosylated IgG1. The second polypeptide comprises from the N-terminus to the C-terminus: the light chain variable domain $V_L$ of atezolizumab, and antibody kappa light chain $C_L$ domain. BCP-85 has the format of FIG. 9.

BCP-84 and BCP-85 each consists of two copies of the first polypeptide and two copies of the second polypeptide. The IgG1 Fc region for the constructs was a non-glycosylated IgG1. Furthermore, the Fc region of the bispecific antigen binding protein may be swapped with IgG Fc of a different isotype, for example, the wild-type IgG1 isotype for the IgG4 isotype with S228P mutation. The Fc region of non-glycosylated IgG isotype has no binding affinity to FcγRs, and thus is preferable over wild-type IgG1 isotype in some embodiments for avoiding ADCC-mediated depletion of PD-L1 or CTLA-4 positive cells.

Production

The plasmids of BCP-84 and BCP-85 were prepared and transiently expressed in CHO cells. The BABPs were purified by one-step protein A chromatography and stored in PBS buffer, pH7.4. The composition and purity of the purified BABPs were analyzed by SDS-PAGE under both reduced and non-reduced conditions. The sizes of the polypeptide chains as well as the full-length protein of BABP molecules were consistent with their calculated molecular mass based on the amino acid sequences. To further study the physical properties of the 2 BABPs in solution, size exclusion chromatography was used to analyze each protein. Both BABPs exhibited a single major peak, demonstrating physical homogeneity as monomeric BABP molecules. A summary of this data is shown in the Table 8.

TABLE 8

Production of exemplary PD-L1/CTLA-4 BABPs.

| BABP | Host cell | Transient expression (mg/ml) | Monomeric molecule (HPLC) | Storage buffer |
|---|---|---|---|---|
| BCP-84 | CHO-3E7 | 74.4 | 95.34% | PBS, pH 7.2 |
| BCP-85 | CHO-3E7 | 77.4 | 96.94% | PBS, pH 7.2 |

Stability Analysis

To determine thermal stability and aggregation of the BABPs, DSC (Differential Scanning Calorimetry) and DLS (Dynamic Light Scattering) experiments were carried out as described in Example 1. As shown in Table 9, Tm and Tagg of BCP-84 and BCP-85 are comparable to those of biosimilar atezolizumab (e.g., compared to TECENTRIQ®).

TABLE 9

DSC and DLS analysis of exemplary PD-L1/CTLA-4 BABPs.

| BABP | $T_m$ (° C.) | $T_{agg}$ (° C.) |
|---|---|---|
| BCP-84 | 70.8 | 70.3 |
| BCP-85 | 70.3 | 69.6 |
| Biosimilar atezolizumab | 71.8 | 69.2 |

Example 5: In Vitro Functional Assays of PD-L1/CTLA-4 Bispecific Antigen Binding Proteins BCP-84 and BCP-85 were tested in the in vitro assays described below to assess the functional blockade of PD-L1 and CTLA-4 by the BABPs.

Target Binding Assays

The ability of the BABPs to bind PD-L1 and CTLA-4 can be determined using Surface Plasmon Resonance method (e.g., BIACORE®), an enzyme-linked immunosorbent assay, a Fluorescence-Assisted Cell Sorting method (FACS), or a combination thereof. The analyses can be performed on activated T cells.

Binding of each BABP to PD-L1 and CTLA-4 expressed on PD-L1 and CTLA-4 expression stable cell lines, was determined using a fluorescence-activated cell sorting (FACS)-based assay. BABP samples were prepared (starting at 1 µM, 3-fold serial dilution with 10 concentrations) and incubated with PD-L1 and CTLA-4 cells. Cells bound to BCP-84 and BCP-85 BABPs were detected by an Alexa Fluor 488-conjugated anti-human antibody (Jackson ImmunoResearch). The $EC_{50}$ was calculated by GraphPad PRISM™ Version 6.0.

Binding kinetics of BCP-84 and BCP-85 to PD-L1 was determined using His-tagged human PD-L1 protein captured on a CM5 sensor chip (Biacore). 6 different samples of each BABP were prepared starting at 50 nM with 3-fold serial dilution. Each BABP sample was flowed over the antigen-coated chip, and avidity was determined using Surface Plasmon Resonance.

Binding kinetics of BCP-84 and BCP-85 to CTLA-4 were determined using His-tagged human CTLA-4 coated on a CM5 sensor chip (Biacore). 6 different samples of each BABP were prepared starting at 200 nM with 2-fold serial dilution. Each BABP sample was flowed over the antigen-coated chip, and avidity was determined using Surface Plasmon Resonance.

The affinity data of BCP-84 and BCP-85 to PD-L1 and CTLA-4 are shown in Table 10.

Inhibition of Ligand Binding by FACS Analysis

Inhibition of ligand binding by BCP-84 and BCP-85 were assessed by a FACS assay.

To assess inhibition of PD-L1 by the BABPs, CHO cells expressing human PD-L1 were dissociated from adherent culture flasks and mixed with varying concentrations of each BABP (starting at 1 µM, with 3-fold serial dilution for 10 concentrations) and 0.1 µM of hPD-1-Fc fusion protein having a biotin label. The mixture was equilibrated for 30 minutes at room temperature, and washed three times with FACS buffer (PBS containing 1% BSA). PE/Cy5 Streptavidin secondary antibody was then added to the mixtures and incubated for 15 minutes at room temperature. Subsequently, the cells were washed with FACS buffer and analyzed by flow cytometry. Data was analyzed with PRISM™ (GraphPad Software, San Diego, Calif.) using non-linear regression, and IC50 values were calculated and shown in Table 10. The competition assays demonstrate the ability of BCP-84 and BCP-85 to efficiently inhibit PD-1/PD-L1 interactions similar to biosimilar atezolizumab.

To assess inhibition of B7-1 (a CTLA-4 ligand) by BCP-84 and BCP-85, CHO cells expressing human B7-1 cells were dissociated from adherent culture flasks and mixed with varying concentrations of each BABP (starting at 1 µM, with 3-fold serial dilution for 10 concentrations) and 0.1 µM of hCTLA-4-Fc fusion protein having a biotin label. The mixture was equilibrated for 30 minutes at room temperature, and washed three times with FACS buffer (PBS containing 1% BSA). PE/Cy5 Streptavidin secondary antibody was then added to the mixtures and incubated for 15 minutes at room temperature. Subsequently, the cells were washed again with FACS buffer and analyzed by flow cytometry. Data were analyzed with PRISM™ (GraphPad Software, San Diego, Calif.) using non-linear regression, and IC50 values were calculated and shown in Table 10. The competition assays demonstrate the ability of the BCP-84 and BCP-85 to efficiently inhibit CTLA-4/B7-1 interactions similar to the corresponding sdAb-Fc and ipilimumab (e.g., YERVOY®).

TABLE 10

Binding data of exemplary PD-L1/CTLA-4 BABPs.

| | PD-L1 | | | CTLA-4 | | |
|---|---|---|---|---|---|---|
| Construct | KD (nM) | $EC_{50}$ (nM) | IC50 (nM) | KD (nM) | $EC_{50}$ (nM) | IC50 (nM) |
| BCP-84 | 0.6 | 3.1 | 2.4 | 4.1 | 2 | 5.5 |
| BCP-75 | 0.4 | 3.4 | 2.0 | 3.6 | 3.7 | 5.1 |
| Biosimilar atezolizumab | 0.4 | 2.8 | 1.8 | N/A | N/A | N/A |
| sdAb-2-Fc | N/A | N/A | N/A | S4.2 | 3.2 | 4.1 |
| sdAb-3-Fc | N/A | N/A | N/A | 5.5 | 3.5 | 5.1 |
| ipilimumab (YERVOY®) | N/A | N/A | N/A | 14.8 | 13.2 | 8.5 |

In Vitro Functional Assays

Blockade of the PD-L1 and CTLA-4 pathways by BCP-84 and BCP-85 can be studied using a variety of bioassays that monitor T cell proliferation, IFN-γ release, IL-2 secretion or expression of reporter gene that is driven by signaling in the PD-1 or CTLA-4 pathway.

Table 11 shows data on biological activities of anti-PD-1 neutralizing antibody in a PD-1/PD-L1 cell-based assay using the PD-1/NFAT Reporter-Jurkat cells. Briefly, CHO- K1 cells were stably expressed with human PD-L1 and an engineered T cell receptor (TCR) activator. The affecter cells-PD-1/NFAT Reporter-Jurkat cells were pre-incubated with serial dilution of BCP-84 and BCP-85 for 30 minutes prior to co-culture with engineered CHO-K1 cells. After ~6 hours of stimulation, ONE-STEP™ Luciferase reagent was added to the cells to measure NFAT activity. Data was analyzed with PRISM™ (GraphPad Software, San Diego, Calif.) using non-linear regression, and $EC_{50}$ values were calculated and shown in Table 11. The reporter assay demonstrate the ability of BCP-84 and BCP-85 to efficiently activate NFAT signal similar to biosimilar atezolizumab.

PD-L1 pathway inhibition by BCP-84 and BCP-85 was studied by determining the IL-2 secretion level in mixed lymphocyte reactions (MLR) containing target cells expressing PD-L1 (such as dendritic cells), activated T cells, and BABP. Briefly, human $CD4^+$ T cells and allogeneic monocytes were purified from PBMC using isolation kits (Miltenyl Biotec). Monocytes were induced into dendritic cells. Each well contained $10^5$ $CD4^+$ T cells and $10^4$ allogeneic dendritic cells with a final working volume of 200 µl. Each BABP was added into each well at different concentrations. A no-antibody well was used as the background control. Human IgG1 was used as the negative control, and biosimilar atezolizumab was used as the positive anti-PD-L1 antibody control. After incubating for 72 hours at 37° C. in a 5% C02 incubator, 100 µl medium was taken from each testing well for IL-2 measurement (Cisbio). Concentration-dependent secretion of IL-2 in the MLRs was used to extract an $EC_{50}$ value for BCP-84 and BCP-85 against PD-L1, which is compared with the $EC_{50}$ value of backbone antibody atezolizumab (see, Table 12).

CTLA-4 pathway inhibition by the BABPs was studied by determining IL-2 secretion level in mixed lymphocyte reactions containing target cells expressing CD80, activated T cells, and each BABP. Human $CD4^+$ T cells were purified from PBMC using isolation kits (Miltenyl Biotec). Each well contained $10^5$ $CD4^+$ T cells and $10^4$ CHO-K1/human CD80 (CHO-K1 stably expressing human CD80) with a final working volume of 200 µl. Each BABP was added into each well at different concentrations. A no-antibody well was used as the background control. Human IgG4 was used as the negative control and ipilimumab (e.g., YERVOY®) was used as the positive anti-CTLA4 antibody control. CTLA4-Fc (GenScript, Z03373-50) was added into the system to initiate the reaction. After incubating for 24 hours at 37° C. in a 5% C02 incubator, 100 µl medium was taken from each testing well for IL-2 measurement (Cisbio). Concentration-dependent secretion of IL-2 in the CTLA-4 blockade bioassays was used to extract an $EC_{50}$ value for the BABPs against CTLA-4, which is compared with the $EC_{50}$ value of control CTLA-4 antibody ipilimumab (e.g., YERVOY®) (see, Table 11).

TABLE 11

In vitro biological assay of exemplary PD-L1/CTLA-4 BABPs.

| Construct | PD-L1 $EC_{50}$ (nM) | CTLA-4 $EC_{50}$ (nM) |
|---|---|---|
| BCP-84 | 2.1 | 12.8 |
| BCP-75 | 2.2 | 9.2 |
| Biosimilar atezolizumab | 2 | N/A |
| sdAb-2 | N/A | 17.0 |
| sdAb-3 | N/A | 13.1 |
| ipilimumab (YERVOY®) | N/A | 17.6 |

TABLE 12

Mixed lymphocyte reactions of exemplary PD-L1/CTLA-4 BABPs.

| Construct | IFN-γ $EC_{50}$ (nM) | IL-2 $EC_{50}$ (nM) |
|---|---|---|
| BCP-79 | 1.45 | 0.56 |
| BCP-80 | 1.16 | 0.58 |
| Biosimilar atezolizumab | 0.44 | 0.67 |

Example 6: In Vivo Anti-Tumor Efficacy of PD-L1/CTLA-4 Bispecific Antigen Binding Proteins This example describes in vivo experiments assessing the functional blockade of PD-L1 and CTLA-4 by BCP-84 and BCP-85. Anti-tumor efficacy was evaluated in tumor models developed with human CTLA-4 Knock-in mice. As biosimilar atezolizumab also binds to mouse PD-L1, humanization of CTLA-4 in mice enabled direct in vivo evaluation of the efficacy of BCP-84 and BCP-85 BABPs in a mouse tumor xenograft model.

The mouse xenograft models were prepared by implanting tumor cells into C57BL/6 CTLA-4 KI mice. A murine colon adenocarcinoma cell line MC38 stable expression human PD-L1 was used in this assay. MC38-h PD-L1 KI cells ($10^7$) were subcutaneously injected in 8-week-old C57BL/6 CTLA-4 KI Mice. Tumor size was measured with a caliper, and tumor volume was calculated by the modified ellipsoid formula: length×(width)$^2$/2. When tumors reached a volume of approximately 90-130 mm$^3$, mice were randomly assigned to different treatment groups, which were maintained for 2 or 6 weeks. The mice were administered vehicle control, anti-PD-L1 antibody (biosimilar atezolizumab), anti-CTLA-4 antibody (sdAb-2-Fc, or sdAb-3-Fc), combination of biosimilar atezolizumab and anti-CTLA-4 antibody (sdAb-2-Fc, or sdAb-3-Fc), or BABP (BCP-84 or BCP-85) by intraperitoneal injection. Efficacy of the BABPs was evaluated by assessing inhibition of tumor size and tumor weight.

As shown in FIG. 25, the combination of biosimilar atezolizumab and anti-CTLA-4 antibody (sdAb-2-Fc, or sdAb-3-Fc) demonstrated higher tumor inhibition efficacy over either monotherapy in the mouse tumor model. Notably, the anti-tumor efficacy of BCP-84 and BCP-85 was comparable as the combination therapy.

Example 7: Construction, Expression and Biophysical Characterization of Ang2/VEGF Bispecific Antigen Binding Proteins This example describes the construction and expression of exemplary Ang2/VEGF BABPs. Four constructs were designed and expressed, each comprising two polypeptide chains as follows:

Construct 1 (BCP-49): The first polypeptide comprises from the N-terminus to the C terminus: the $V_HH$ domain of an anti-VEGF sdAb, a peptide linker (SEQ ID NO: 13), the heavy chain variable domain $V_H$ of LC10 (anti-Ang2 antibody), and heavy chain constant domains of IgG1. The second polypeptide comprises from the N-terminus to the C-terminus: the light chain variable domain $V_L$ of LC10 (anti-Ang2 antibody), and antibody lambda light chain $C_L$ domain. BCP-49 has the format of FIG. 9.

Construct 2 (BCP-50): The first polypeptide comprises from the N-terminus to the C terminus: the heavy chain variable domain $V_H$ of LC10 (anti-Ang2 antibody), heavy chain constant domains of IgG1, a peptide linker (SEQ ID NO: 13), and the $V_HH$ domain of an anti-VEGF sdAb. The second polypeptide comprises from the N-terminus to the C-terminus: the light chain variable domain $V_L$ of LC10 (anti-Ang2 antibody), and antibody lambda light chain $C_L$ domain. BCP-50 has the format of FIG. 4.

Construct 3 (BCP-51): The first polypeptide comprises from the N-terminus to the C terminus: the heavy chain variable domain $V_H$ of LC10 (anti-Ang2 antibody), and heavy chain constant domains of IgG1. The second polypeptide comprises from the N-terminus to the C-terminus: the $V_HH$ domain of an anti-VEGF sdAb, a peptide linker (SEQ ID NO: 13), the light chain variable domain $V_L$ of LC10 (anti-Ang2 antibody), and antibody lambda light chain $C_L$ domain. BCP-51 has the format of FIG. 13.

Construct 4 (BCP-52): The first polypeptide comprises from the N-terminus to the C terminus: the heavy chain variable domain $V_H$ of LC10 (anti-Ang2 antibody), and heavy chain constant domains of IgG1. The second polypeptide comprises from the N-terminus to the C-terminus: the light chain variable domain $V_L$ of LC10 (anti-Ang2 antibody), antibody lambda light chain $C_L$ domain, a peptide linker (SEQ ID NO: 13), and the $V_HH$ domain of an anti-VEGF sdAb. BCP-52 has the format of FIG. 11.

The plasmids of the four BABPs were prepared and transiently expressed in CHO cells. The BABPs were purified by one-step protein A chromatography and store in 4% Sucrose, 50 mM Histidine, 50 mM Arginine, pH 6.0 buffer. The composition and purity of the purified BABPs were analyzed by SDS-PAGE under both reduced and non-reduced conditions. The sizes of the chains as well as the full-length protein of BABP molecules are consistent with their calculated molecular mass based on the amino acid sequences. To further study the physical properties of the four BABPs in solution, size exclusion chromatography was used to analyze each protein. All four proteins exhibited a single major peak, demonstrating physical homogeneity as monomeric BABP molecules. A summary of this data is shown in the Table 13.

TABLE 13

Production of exemplary Ang2/VEGF BABPs.

| BABP | Host cell line | Expression (mg/L) | Monomeric molecule | Buffer |
| --- | --- | --- | --- | --- |
| BCP-49 | CHO-3E7 | 90.3 | 97.92% | 4% Sucrose, 50 mM Histidine, 50 mM Arginine, pH 6.0 |
| BCP-50 | | 97.5 | 98.20% | |
| BCP-51 | | 67.5 | 98.16% | |
| BCP-52 | | 95.5 | 97.77% | |

Example 8: In Vitro Functional Assays of Ang2/VEGF Bispecific Antigen Binding Proteins The binding kinetics of BABPs to rhAng2 and rhVEGF was determined by Surface Plasmon Resonance with a BIACORE® T200 instrument using HBS-EP (10 mM HEPES, pH 7.4, 150 mM NaCl, 3 mM EDTA, and 0.05% Tween-20). Briefly, goat anti-human IgG polyclonal antibody was directly immobilized across a CM5 biosensor chip using a standard ammine coupling kit according to manufacturer's instructions. Purified FIT-Ig samples were diluted in HEPES-buffered saline for capture across goat anti-human IgG Fc specific reaction surfaces, and injected over reaction matrices at a flow rate of 5 l/min. The association and dissociation rate constants, $k_{on}$ and $k_{off}$ were determined under a continuous flow rate of 30 l/min. The kinetics data is shown in Table 14. The antibody affinities of the Ang2/VEGF BABPs are similar to the corresponding 4-chain antibody LC10, or anti-VEGF sdAbs fused to an Fc fragment.

TABLE 14

Binding data of exemplary Ang2/VEGF BABPs.

| | VEGF | | Ang2 | |
| --- | --- | --- | --- | --- |
| Construct | KD (nM) | EC50 | KD (nM) | EC50 |
| BCP-49 | 0.51 | 0.25 | 2.3 | 3.1 |
| BCP-50 | 0.48 | 0.39 | 8.8 | 3.9 |
| BCP-51 | 0.32 | 0.32 | 1.9 | 3.5 |
| BCP-52 | 1.29 | 0.36 | 1.4 | 3.8 |
| sdAbVEGF-Fc | 0.35 | 0.23 | | |
| LC10 | | | 3.4 | 2.8 |

To assess the bioactivity of Ang2/VEGF BABPs targeting VEGF, HUVEC cells were used for a mitogenic assay. HUVEC cells were seeded in 6-well plates at a density of $6 \times 10^3$ cells per well, and cultured in low glucose Dulbecco's modified Eagle's medium (DMEM) (GIBCO) supplemented with 10% calf serum, 2 mM glutamine, and antibiotics (growth medium). Anti-VEGF sdAb fused to an Fc fragment ("sdAbVEGF-Fc") was then added at concentrations ranging between 1 and 5000 ng/ml. After 2-3 hours, purified rhVEGF165 was added at a final concentration of 3 ng/ml. After five or six days, cells were dissociated by exposure to trypsin and counted in a Coulter counter. Variation from the mean number of cells did not exceed 10%. Data were analyzed by a four-parameter curve fitting program. As shown in Table 14, all four Ang2/VEGF BABPs have comparable biological activities targeting VEGF as sdAbVEGF-Fc.

To assess Ang-2 inhibition by the BABPs, Tie2 phosphorylation, which was induced by inhibition of Ang-2, was measured as follows. HEK293-Tie2 cells were stimulated with Ang-2 for 5 minutes in the presence or absence of LC10 antibody or each BABP. Then, levels of phosphorylated Tie2 ("P-Tie2") in cell lysates were quantified using a sandwich ELISA according to the manufacturer's instructions. $IC_{50}$ values were determined using GraphPad PRISM™ version 6. As shown in Table 14, all four Ang2/VEGF BABPs have comparable biological activity targeting Ang2 as LC10.

Example 9: In Vivo Efficacy of Ang2/VEGF Bispecific Antigen Binding Proteins

A375 xenografts were used to evaluate the anti-tumor efficacies of Ang2/VEGF BABPs described in Examples 7-8 as compared to anti-Ang2 sdAb and anti-VEGF antibody monotherapy or combination therapy.

$10^7$ A375 cells were subcutaneously injected to 6-week-old Balb/c nude mice. Tumor size was measured with a caliper, and tumor volume was calculated by the modified ellipsoid formula: length×(width)²⁄2. When tumors reached a volume of approximately 90-130 mm³, mice were randomly assigned to different treatment groups, which were maintained for 2 or 6 weeks. The mice were administered vehicle control, LC10, sdAbVEGF-Fc, LC10+sdAbVEGF-Fc combination, or BCP-49 intravenously twice a week.

Tumor volume was measured twice a week and data is shown in FIG. 26A. Compared to the vehicle control, significant inhibition of tumor growth was observed in the sdAbVEGF-Fc, LC10+sdAbVEGF-Fc combination therapy, and BCP-49 treatment groups. Notably, synergic activity was observed in the BCP49-treated group compared to the combination therapy group.

Tumor weight was also measured after study completion. Consistent with the tumor volume results, BCP49 was more effective than the LC10+sdAbVEGF-Fc combination therapy in reducing tumor weight, as shown in FIG. 26B.

All citations throughout the disclosure are hereby expressly incorporated by reference.

What is claimed is:

1. A multispecific antigen binding protein comprising:
   (a) a first antigen binding portion comprising a single-chain variable fragment (scFv) comprising a heavy chain variable domain (VH) and a light chain variable domain (VL), wherein the scFv specifically binds a first epitope,
   (b) a second antigen binding portion comprising a single-domain antibody (sdAb) that specifically binds a second epitope, and
   (c) Fc region,
   wherein the first antigen binding portion and the second antigen binding portion are fused to each other, and wherein the N-terminus of the sdAb is fused to the C-terminus of the scFv and the C-terminus of the sdAb is fused to the N-terminus of the Fc region.

2. The multispecific antigen binding protein of claim 1, wherein the first antigen binding portion and the second antigen binding portion are fused to each other via a peptide bond or a peptide linker.

3. The multispecific antigen binding protein of claim 2, wherein the peptide linker is no more than about 30 amino acids long.

4. The multispecific antigen binding protein of claim 3, wherein the peptide linker comprises the amino acid sequence of SEQ ID NO: 1, 8 or 13.

5. The multispecific antigen binding protein of claim 1, wherein the first epitope is from an immune checkpoint molecule.

6. The multispecific antigen binding protein of claim 5, wherein the immune checkpoint molecule is selected from the group consisting of PD-1, PD-L1, PD-L2, CTLA-4, B7-H3, TIM-3, LAG-3, VISTA, ICOS, 4-1BB, OX40, GITR, and CD40.

7. The multispecific antigen binding protein of claim 6, wherein the scFv is an anti-PD-1 scFv or anti-PD-L1 scFv.

8. The multispecific antigen binding protein of claim 7, wherein the anti-PD-1 scFv is derived from pembrolizumab or nivolumab, and wherein the anti-PD-L1 scFv is derived from durvalumab or atezolizumab.

9. The multispecific antigen binding protein of claim 5, wherein the sdAb specifically binds an immune checkpoint molecule.

10. The multispecific antigen binding protein of claim 9, wherein the immune checkpoint molecule is selected from the group consisting of PD-1, PD-L1, PD-L2, CTLA-4, B7-H3, TIM-3, LAG-3, VISTA, ICOS, 4-1BB, OX40, GITR, and CD40.

11. The multispecific antigen binding protein of claim 10, wherein the sdAb is an anti-CTLA-4 sdAb.

12. The multispecific antigen binding protein of claim 1, wherein the first epitope is from a tumor antigen.

13. The multispecific antigen binding protein of claim 1, wherein the first epitope is from a pro-inflammatory molecule.

14. A pharmaceutical composition comprising the multispecific antigen binding protein of claim 1 and a pharmaceutically acceptable carrier.

15. A method of treating a disease in an individual, comprising administering to the individual an effective amount of the pharmaceutical composition of claim 14.

16. The multispecific antigen binding protein of claim 1, wherein the multispecific antigen binding protein comprises two identical polypeptides each comprising from the N-terminus to the C-terminus: scFv-an optional peptide linker-sdAb-CH2-CH3.

17. The multispecific antigen binding protein of claim 1, wherein the Fc region is an IgG1 Fc, or an IgG4 Fc comprising an S228P mutation, and wherein the amino acid position numbering is according to Kabat numbering.

18. The multispecific antigen binding protein of claim 1, wherein the multispecific antigen binding protein is bispecific.

19. The multispecific antigen binding protein of claim 1, comprising a first polypeptide chain and a second polypeptide chain each having a structure from the N-terminus to the C-terminus as follows: scFv-$V_HH$-$C_H2$-$C_H3$, wherein:
- each scFv specifically binds the first epitope,
- each $V_HH$ specifically binds the second epitope, and
- the $C_H2$ and $C_H3$ domains of the first polypeptide chain associate with the $C_H2$ and $C_H3$ domains of the second polypeptide chain to form the Fc region.

* * * * *